United States Patent
Bossé et al.

(10) Patent No.: US 10,942,177 B2
(45) Date of Patent: Mar. 9, 2021

(54) HOLLOW POLYMER FIBER OPTIC SYSTEM FOR SINGLE ANALYTE AND MULTIPLEXED ANALYTE DETECTION

(71) Applicant: PerkinElmer Health Sciences, Inc., Waltham, MA (US)

(72) Inventors: Roger Bossé, Longueuil (CA); Wael I. Yared, Lexington, MA (US); Peter A. Harvey, Wilmington, MA (US); Kevin Groves, Arlington, MA (US); Ilias Faqir, Holliston, MA (US); Michael Meltzer, Norwood, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

(21) Appl. No.: 16/800,890

(22) Filed: Feb. 25, 2020

(65) Prior Publication Data
US 2020/0232926 A1    Jul. 23, 2020

Related U.S. Application Data

(62) Division of application No. 15/359,422, filed on Nov. 22, 2016, now Pat. No. 10,677,735.
(Continued)

(51) Int. Cl.
*G01N 33/552* (2006.01)
*G01N 33/543* (2006.01)
(Continued)

(52) U.S. Cl.
CPC ....... *G01N 33/54373* (2013.01); *G01N 21/64* (2013.01); *G01N 21/77* (2013.01);
(Continued)

(58) Field of Classification Search
None
See application file for complete search history.

(56) References Cited

U.S. PATENT DOCUMENTS

| 5,496,997 A | 3/1996 | Pope |
| 6,346,384 B1 | 2/2002 | Pollner |
| (Continued) | | |

FOREIGN PATENT DOCUMENTS

| CN | 1902476 A | 1/2007 |
| CN | 101189520 A | 5/2008 |
| (Continued) | | |

OTHER PUBLICATIONS

Beaudet, L. et al., AlphaLISA immunoassays: the no-wash alternative to ELISAs for research and drug discovery, Nature Methods, pp. an8-an9 (2008).
(Continued)

*Primary Examiner* — Christopher L Chin
(74) *Attorney, Agent, or Firm* — Choate, Hall & Stewart LLP; William R. Haulbrook; Ronen Adato

(57) ABSTRACT

Presented herein are methods, systems, and apparatus for single analyte detection or multiplexed analyte detection based on amplified luminescent proximity homogeneous assay ("alpha") technology, but using hollow polymer fiber optics doped with 'acceptor bead' dye (e.g., thioxene, anthracene, rubrene, and/or lanthanide chelates) or 'donor bead' dye (e.g., phthalocyanine) that carry a signal generated by the dopant via singlet oxygen channeling.

21 Claims, 22 Drawing Sheets

Related U.S. Application Data

(60) Provisional application No. 62/259,000, filed on Nov. 23, 2015.

(51) Int. Cl.
  *G01N 21/64* (2006.01)
  *G01N 21/77* (2006.01)

(52) U.S. Cl.
  CPC ....... *G01N 21/7703* (2013.01); *G01N 33/552* (2013.01); *G01N 2021/6441* (2013.01); *G01N 2021/773* (2013.01); *G01N 2021/7709* (2013.01); *G01N 2021/7786* (2013.01); *G01N 2201/0221* (2013.01)

(56) References Cited

U.S. PATENT DOCUMENTS

| | | |
|---|---|---|
| 7,260,297 B2 | 8/2007 | Hajto et al. |
| 10,677,735 B2 | 6/2020 | Bosse et al. |
| 2004/0240832 A1 | 12/2004 | Hoke |
| 2009/0156942 A1 | 6/2009 | Phillips et al. |
| 2009/0227043 A1 | 9/2009 | Huang |
| 2017/0167984 A1 | 6/2017 | Bosse et al. |

FOREIGN PATENT DOCUMENTS

| | | |
|---|---|---|
| CN | 101542269 A | 9/2009 |
| WO | WO-01/73129 A2 | 10/2001 |
| WO | WO-2005/054831 A1 | 6/2005 |
| WO | WO-2006/119368 A2 | 11/2006 |
| WO | WO-2008/065591 A1 | 6/2008 |

OTHER PUBLICATIONS

International Partial Search Report, PCT/US2016/063400, 4 pages, dated Mar. 2, 2016.

Perkinelmer, From Small Molecules to Live Cells the Assay That Measures It All, ELISA Alternatives, Alpha Technology Solutions, PerkinElmer, 16 pages (2013).

Written Opinion, PCT/US2019/063400 (Hollow Polymer Fiber Optic System for Single Analyte and Multiplexed Analyte Detection, filed Nov. 22, 2016), issued by European Patent Office, 18 pages, dated Jun. 7, 2018.

HOLLOW POLYMER FIBER OPTIC SYSTEM FOR SINGLE ANALYTE AND MULTIPLEXED ANALYTE DETECTION

RELATED APPLICATIONS

The present application is a divisional application of U.S. patent application Ser. No. 15/359,422, Nov. 22, 2016, which claims priority to U.S. Provisional Patent 62/259,000, entitled "Hollow Polymer Fiber Optic System for Single Analyte and Multiplexed Analyte Detection," and filed Nov. 23, 2015, the content of each of which are incorporated by reference in their entirety.

TECHNICAL FIELD

Presented herein are methods, systems, and apparatus for analyte detection. For example, methods, systems, and apparatus are described herein that use doped hollow polymer fiber optics to carry a signal generated by the dopant via singlet oxygen channeling for detection of one or more analytes in a sample.

BACKGROUND

There are a number of bead-based assay technologies used to study biomolecular interactions in a microplate format, for example, AlphaScreen® and AlphaLISA®, manufactured by PerkinElmer of Waltham, Mass. The acronym "Alpha" stands for amplified luminescent proximity homogeneous assay. These technologies are non-radioactive, homogeneous proximity assays. Binding of molecules captured on the beads leads to an energy transfer from one bead to the other, ultimately producing a detectable luminescent/fluorescent signal, which provides qualitative and quantitative information about one or more analytes in a sample.

AlphaScreen® and AlphaLISA® assays each utilize two bead types: Donor beads and Acceptor beads. Donor beads comprise a photosensitizer, for example, phthalocyanine, which converts ambient oxygen to an excited and reactive form of oxygen, singlet oxygen, upon illumination at 680 nm. Singlet oxygen is not a radical; it is molecular oxygen with a single excited electron. Like other excited molecules, singlet oxygen has a limited lifetime prior to falling back to ground state. Within its 4 μsec half-life, singlet oxygen can diffuse approximately 200 nm in solution, as compared to TR-FRET which has a maximum transfer distance of about 10 nm. If an Acceptor bead is within that proximity, energy is transferred from the singlet oxygen to thioxene derivatives within the Acceptor bead, subsequently culminating in light production within a range of wavelengths, e.g., 520-620 nm (AlphaScreen®) or at a particular wavelength, e.g., 615 nm (AlphaLISA®). In the absence of an Acceptor bead, singlet oxygen falls to ground state and no signal is produced. This proximity-dependent chemical energy transfer is the basis for AlphaScreen's homogeneous nature, such that no washing steps are required, unlike ELISA assays, electrochemiluminescence, and flow cytometry assays, thereby offering a significant advantage.

Both AlphaScreen® and AlphaLISA® rely on the same Donor beads yet use different Acceptor beads. AlphaScreen® Acceptor beads are embedded with three dyes: thioxene, anthracene, and rubrene. Rubrene, the final fluor, emits light detectable between 520-620 nm. In the AlphaLISA® Acceptor beads, anthracene, and rubrene are substituted with an Europium chelate. The Europium (Eu) chelate is directly excited by the 340 nm light resulting from the conversion of thioxene to a di-ketone derivative following its reaction with singlet oxygen. The excited Europium chelate generates an intense light detectable within a much narrower wavelength bandwidth centered around 615 nm. In contrast to the AlphaScreen®, the AlphaLISA® emission is therefore less susceptible to interference by either artificial or natural compounds (such as hemoglobin) that absorb light between 500-600 nm.

AlphaScreen® and AlphaLISA® are typically run as multi-well (e.g., 96-, 384-, or 1536-well) assays, and are used to perform both biochemical and cell-based assays. They can be used for low to high affinity binding interactions (e.g., pM to mM), and can be used for high-throughput screening (HTS). AlphaLISA® is compatible with complex matrices such as cell lysates, serum, plasma, CSF, and the like. These systems can perform immunoassays, epigenetic assays, kinase assays, antibody detection and characterization, immunogenicity, selective detection of sAPP and amyloid peptides, alpha protease assays, alpha ligand-receptor assays, cAMP assays, cGMP assays, and detection of protein-protein and protein-nucleic acid interactions.

AlphaPlex™, manufactured by PerkinElmer of Waltham, Mass., is a homogeneous multiplexing reagent technology that utilizes the above-described alpha technology. By using multiple Acceptor beads which emit different wavelengths, multiple analytes can be detected. The system offers accurate multiplex quantification of a wide range of analytes, from large proteins to small proteins and scarce biological samples such as primary cells and stem cells, and is applicable to a wide range of applications including biomarkers for PD/PK, biomarkers for stem cells, kinase (e.g., total vs. phosphorylated protein), epigenetic markers (e.g., total histone vs. specific marker), amyloid peptides, IgG profiling, and assay normalization with housekeeping proteins.

The existing systems that utilize alpha technology are not portable. Crop sciences and animal health researchers/technicians are required to procure samples in the field, then take them back to the laboratory for analysis. Many samples may need to be taken to insure that a particular analyte of interest will be present in at least some of the samples when they are taken back to the lab for analysis.

Portable aminoassay devices include lateral flow devices, e.g., an aminoassay run in a cartridge, such as a pregnancy test, where the sample reacts with an antibody and produces a visible color when the analyte is present in the sample. Other portable systems involve dipsticks, e.g., paper or plastic embedded with reagents, which are dipped into a solution for determination of the presence of an analyte in the sample. These systems are typically not very accurate, and are usually limited to qualitative analyses.

There is a need for robust, easy-to-use, portable assay systems and devices that are more accurate and more sensitive than existing portable systems.

SUMMARY OF THE INVENTION

Presented herein are methods, systems, and apparatus for single analyte detection or multiplexed analyte detection based on the above-mentioned alpha technology, but which utilize hollow polymer fiber optics doped with 'acceptor bead' dye and/or 'donor bead' dye. For example, an acceptor bead dye may comprise thioxene, anthracene, rubrene, and/or or lanthanide chelates, e.g., europium chelate, terbium chelate, dysprosium chelate, samarium chelate, ytterbium chelate, erbium chelate and/or thulium chelate, and/or variations thereof. A 'donor bead' dye may comprise, for example, phthalocyanine, naphthalocyanine, a chlorin, a phorphin, a phorphyrin, stellacyanin, chlorophyll, rose bengal, and/or variations thereof. The polymer fiber optics carry a signal generated by the dopant via singlet oxygen channeling, which is detected and used to identify the presence and/or quantity of an analyte or multiple analytes of interest in a given sample.

In certain embodiments, the system is portable, easy to use, and provides robust measurement (qualitative and/or quantitative) of one or more analytes of interest. In particular, for crop sciences and animal health applications, samples traditionally need to be procured in the field and brought back to the lab for analysis. The hollow polymer fiber optic system described herein provides a robust, easy-to-use, dependable system for making such measurements in the field rather than in the lab. Moreover, very small volumes of sample are sufficient for testing, given the small internal volume of the hollow fiber optic tubes. The hollow tubes also simplify sample procurement, handling, and transport.

For example, it is possible to procure samples in the field and take measurements of those samples in the field to detect the presence and/or quantity (e.g., concentration) of one or more analytes. It is also possible to take measurements of samples in the field to identify the presence of an analyte of interest, then, if further analysis is necessary, transport just those samples containing the analyte of interest back to the lab for further testing, rather than procuring and transporting a large number of samples which may or may not contain the analyte of interest. For example, a portable hand-held device with excitation light source and detector can be used in the field, then desired samples can be taken back to the lab for a more precise measurement.

Multiplexed sample analysis is made possible by the use of different acceptor and/or donor compounds to produce light having different, distinguishable wavelengths when corresponding analytes are present in the sample.

For example, fiber bundles comprising a plurality of hollow polymer optic fibers that are doped with different acceptor dye compositions provide for multiplexed detection of a plurality of analytes. Different fibers in a bundle capture different analytes present in a sample solution introduced into the fibers via different binding partners (e.g. antibodies) conjugated to their interior surfaces. Donor beads doped with donor dye compositions are coated with corresponding binding partners and are introduced into the fibers (e.g. along with the sample, e.g. in a second step, after the sample is introduced into the fibers), and bind to corresponding analytes within the fibers. Upon illumination with excitation light, the donor dyes within the donor beads are excited, resulting in the emission of light from the acceptor dye doped fibers. Different fibers doped with different acceptor dye compositions produce emission light at different, distinguishable wavelengths (e.g., at 545 nm, e.g., at 575 nm, e.g., at 615 nm, e.g. at 645 nm).

In certain embodiments, the system comprises multiple detector and optical filter combinations that distinguishably detect emission light at different particular wavelengths, each corresponding to a particular fiber in the bundle, and, therefore, a particular analyte captured by the fiber.

The multiplexing capacity of the system (e.g. the number of different analytes that can be distinguishably detected using a single fiber and/or fiber bundle) can be further increased through the use of different types of donor beads, doped with different donor dye compositions, in combination with multiple fibers doped with different acceptor dye compositions. In particular, in certain embodiments the system illuminates a fiber and/or fiber bundle with multiple excitation wavelengths (e.g. at 680 nm, e.g. at 775 nm), thereby selectively exciting different types of donor beads depending on the excitation wavelength of the donor dye compositions with which they are doped. Emission light produced in response to illumination with a particular excitation wavelength can thereby be associated with a particular type of donor bead that is coated with a particular binding partner that binds to a particular analyte.

Accordingly, each analyte of a plurality of analytes can be associated with a particular combination of excitation and emission wavelengths, by virtue of the type of donor beads and particular fiber (e.g. doped with a particular acceptor dye) that are conjugated with binding partners that bind to the analyte. The same approach can be also followed with the roles of the beads and fibers reversed, wherein different types of acceptor beads are doped with different acceptor dye compositions, and different fibers are doped with different donor dye compositions. The systems and methods described herein thus provide for a number of flexible and effective approaches for multiplexed detection of multiple analytes in a sample.

Moreover, in certain embodiments, fiber bundles used for multiplexed detection of analytes are arranged in a cartridge comprising multiple fiber bundles. In certain embodiments, multiple fiber bundles, each capable of detecting multiple analytes by virtue of the different doping and binding partner configurations described above, are used in the cartridge to detect multiple analytes in multiples samples. For example, within a given cartridge, each fiber bundle can be contacted with a different sample, thereby providing for multiplexed analyte detection in multiple samples.

In certain embodiments, the arrangement of fiber bundles in a cartridge can be used to simplify the doping and binding partner configurations that are used for multiplexed detection. For example, each fiber bundle of the cartridge can be used for detection of a different analyte. The multiple bundles of a cartridge are contacted with a sample solution comprising a sample to be analyzed, and the bundles are read by illuminating each bundle with excitation light and detecting resultant emission light. The bundles of a cartridge may be read sequentially, or in parallel. Thus, in certain embodiments, using each bundle of a cartridge for detection of a different, corresponding analyte, and distinguishably detecting signal from each bundle (e.g. by sequentially reading signal from each bundle) obviates the need for complex acceptor and/or donor dye doping configurations of the different fibers within a bundle, thereby simplifying the detection process.

Cartridges of fiber bundles thus provide a simple and convenient approach for detecting multiple analytes in multiple samples, for example, in the field.

Aliquots of sample can be drawn up into one or more hollow fibers (e.g., a small bundle) via capillary action. The small required sample size, low cost, ease of transport, portability, adaptability, and accuracy of measurement provide this approach with synergistic advantages over the traditional microplate format, as well as existing lateral flow devices and dipsticks.

In one aspect, the invention is directed to a polymer optic fiber doped with an acceptor dye composition and/or a donor dye composition, the optic fiber capable of transmitting light generated by singlet oxygen channeling for the detection and/or quantification of an analyte of interest in a sample.

In certain embodiments, the polymer optic fiber is doped with an acceptor dye composition. In certain embodiments, the acceptor dye composition comprises a chemiluminescent singlet oxygen acceptor and a fluorescent compound. In certain embodiments, the chemiluminescent singlet oxygen acceptor is selected from the group consisting of thioxene, dioxene, and dithiene. In certain embodiments, the fluorescent compound is a lanthanide chelate. In certain embodiments, the lanthanide chelate comprises a lanthanide selected from the group consisting of europium, terbium, dysprosium, samarium, ytterbium, erbium, and thulium. In certain embodiments, the fluorescent compound comprises an organic dye (e.g. anthracene, rubrene). In certain embodiments, the polymer optic fiber is doped with quantum dots.

In certain embodiments, the polymer optic fiber is doped with a donor dye composition. In certain embodiments, the donor dye composition comprises a photosensitizer that releases singlet oxygen when illuminated with excitation light. In certain embodiments, the photosensitizer is a compound selected from the group consisting of phthalocyanine, naphthalocyanine, a chlorin, a phorphin, a phorphyrin, stellacyanin, chlorophyll, and rose bengal.

In certain embodiments, the polymer optic fiber has an interior diameter that is from 0.1 mm to 2 mm, and an outer diameter that is from 1 mm to 3 mm. In certain embodiments, the polymer optic fiber has an interior diameter that is from 0.5 mm to 1.5 mm. In certain embodiments, the polymer optic fiber has an interior diameter that is sufficiently small to draw liquid into the interior of the polymer optic fiber by capillary action. In certain embodiments, the polymer optic fiber has an interior diameter that preserves capillarity such that liquid (e.g., a solution comprising a sample) is drawn into the interior of the polymer optic fiber by capillary action (e.g., wherein a distance the liquid is drawn into the fiber by capillary action is at least a sufficient distance to enable detection of the transmitted light generated by singlet oxygen channeling (e.g., at least one millimeter)).

In certain embodiments, the polymer optic fiber comprises a first binding partner (e.g., a first antibody, e.g. streptavidin) bound on an interior surface of the polymer optic fiber. In certain embodiments, the polymer optic fiber comprises multiple discrete portions along its length, each of which portions has a different concentration of the first binding partner conjugated to its interior surface for achieving a variety of levels of sensitivity of measurement of an analyte of interest to which the first binding partner binds. In certain embodiments, the polymer optic fiber comprises multiple discrete portions along its length, each of which has a different binding partner conjugated to its interior surface. In certain embodiments, the different binding partners are different antibodies. In certain embodiments, each binding partner is capable of binding to a different variant of a specific antigen. In certain embodiments, each binding partner is capable of binding to a different analyte.

In certain embodiments, the polymer optic fiber comprises multiple hollow cores (e.g. the polymer optic fiber comprises from 5 to 20 hollow cores).

In certain embodiments, the polymer optic fiber comprises polystyrene and/or poly(methyl methacrylate).

In another aspect, the invention is directed to a bundle of polymer optic fibers, each fiber of the bundle doped with a corresponding acceptor dye composition and/or donor dye composition. In certain embodiments, the bundle comprises from 2 to 20 polymer optic fibers.

In certain embodiments, each of a plurality of polymer optic fibers of the bundle is doped with a distinct acceptor dye composition. In certain embodiments, the acceptor dye composition comprises a chemiluminescent singlet oxygen acceptor and a fluorescent compound. In certain embodiments, the chemiluminescent singlet oxygen acceptor is selected from the group consisting of thioxene, dioxene, and dithiene. In certain embodiments, the fluorescent compound is a lanthanide chelate. In certain embodiments, the lanthanide chelate comprises a lanthanide selected from the group consisting of europium, terbium, dysprosium, samarium, ytterbium, erbium, and thulium. In certain embodiments, the fluorescent compound comprises an organic dye (e.g. anthracene, rubrene). In certain embodiments, one or more polymer optic fibers is doped with quantum dots.

In certain embodiments, each of a plurality of polymer optic fibers of the bundle is doped with a distinct donor dye composition. In certain embodiments, the donor dye composition comprises a photosensitizer that releases singlet oxygen when illuminated with excitation light. In certain embodiments, the photosensitizer is a compound selected from the group consisting of phthalocyanine, naphthalocyanine, a chlorin, a phorphin, a phorphyrin, stellacyanin, chlorophyll, and rose bengal.

In certain embodiments, each of a plurality of polymer optic fibers of the bundle has a distinct binding partner conjugated to its interior surface.

In another aspect, the invention is directed to a cartridge comprising a plurality of bundles of polymer optic fibers, wherein each polymer optic fiber of each bundle is doped with a corresponding acceptor dye composition and/or a corresponding donor dye composition. In certain embodiments, the acceptor dye composition comprises a chemiluminescent singlet oxygen acceptor and a fluorescent compound. In certain embodiments, the chemiluminescent singlet oxygen acceptor is selected from the group consisting of thioxene, dioxene, and dithiene. In certain embodiments, the fluorescent compound is a lanthanide chelate. In certain embodiments, the lanthanide chelate comprises a lanthanide selected from the group consisting of europium, terbium, dysprosium, samarium, ytterbium, erbium, and thulium. In certain embodiments, the fluorescent compound comprises an organic dye (e.g. anthracene, rubrene). In certain embodiments, one or more polymer optic fibers is doped with quantum dots.

In certain embodiments, for each bundle of the cartridge, each of a plurality of the polymer optic fibers of the bundle has a distinct binding partner conjugated to its interior surface.

In another aspect, the invention is directed to a system for single analyte and/or multiple analyte detection, the system comprising: a polymer optic fiber doped with an acceptor dye composition and/or a donor dye composition; an excitation light source; and a detector for detecting emission light traveling through the polymer optic fiber resulting from singlet oxygen channeling.

In certain embodiments, the detector is aligned to detect light exiting an end facet of the polymer optic fiber. In certain embodiments, the detector is aligned such that its active area is substantially concentric with an axis of the polymer optic fiber. In certain embodiments, the excitation light source is aligned to illuminate the polymer optic fiber along a length of the polymer optic fiber. In certain embodiments, the excitation light source is aligned to illuminate the polymer optic fiber in a direction perpendicular to the polymer optic fiber. In certain embodiments, the excitation light source is a laser operating at substantially a single wavelength.

In certain embodiments, the system further comprises a housing wherein: the housing surrounds the detector and polymer optic fiber, the housing comprises an excitation light port through which excitation light from the excitation light source can be directed, and the housing is substantially opaque to ambient light.

In certain embodiments, the system further comprises a housing wherein: the housing surrounds the detector, polymer optic fiber, and excitation light source, and the housing is substantially opaque to ambient light.

In certain embodiments, the system comprises a self-contained portable power supply for delivering power to the detector and excitation light source, such that no external power supply is required and the system is portable. In certain embodiments, the power supply comprises a battery.

In certain embodiments, the system is contained within a housing, the housing defining a volume no greater than 750 cm$^3$ (e.g. the system having dimensions no greater than 150 mm by 100 mm by 50 mm, e.g., and/or the system having a weight no greater than 2 lbs., e.g. a weight from 1 to 2 lbs.). In certain embodiments, the housing defines a volume no greater than 750 cm$^3$ (e.g. the system having dimensions no greater than 150 mm by 100 mm by 50 mm, e.g., and/or the system having a weight no greater than 2 lbs., e.g., a weight from 1 to 2 lbs.). In certain embodiments, a total weight of the system is no greater than 2 lbs. (e.g. a total weight of the system is from 1 to 2 lbs.).

In certain embodiments, the polymer optic fiber is doped with an acceptor dye composition, and the excitation light source is operable to illuminate the polymer optic fiber at an excitation wavelength of a donor dye composition that a donor particle to be introduced into the interior of the polymer optic fiber comprises.

In certain embodiments, the detector is responsive to light at an emission wavelength of the acceptor dye composition with which the polymer optic fiber is doped.

In certain embodiments, the system comprises a filter positioned in between the polymer optic fiber and the detector, wherein the filter is substantially opaque to light having a wavelength corresponding to the excitation wavelength of the donor dye composition and the filter is substantially transmissive to light having a wavelength corresponding to the an emission wavelength of the acceptor dye composition with which the polymer optic fiber is doped.

In certain embodiments, the polymer optic fiber is doped with a donor dye composition, and the excitation light source is operable to illuminate the polymer optic fiber at an excitation wavelength of the donor dye composition.

In certain embodiments, the detector is responsive to light at an emission wavelength of an acceptor dye composition that an acceptor particle to be introduced into the interior of the polymer optic fiber comprises.

In certain embodiments, the system comprises a filter positioned in between the polymer optic fiber and the detector, wherein the filter is substantially opaque to light having a wavelength corresponding to the excitation wavelength of the donor dye composition with which the polymer optic fiber is doped and the filter is substantially transmissive to light having a wavelength corresponding to the an emission wavelength of the acceptor dye composition.

In certain embodiments, the system comprises a bundle of polymer optic fibers, each polymer optic fiber of the bundle doped with a corresponding acceptor dye composition and/or donor dye composition. In certain embodiments, each of a plurality of polymer optic fibers of the bundle has a different binding partner (e.g., different antibody) conjugated to its interior surface.

In certain embodiments, a first polymer optic fiber of the bundle is doped with a first acceptor dye composition having a first emission wavelength, a second polymer optic fiber of the bundle is doped with a second acceptor dye composition having a second emission wavelength that is different from the first emission wavelength, the first polymer optic fiber of the bundle has a first binding partner conjugated to its interior surface, and the second polymer optic fiber of the bundle has a second binding partner conjugated to its interior surface, the second binding partner different from the first binding partner. In certain embodiments, the system comprises a first detector and a second detector, the first detector responsive to the first emission wavelength and the second detector responsive to the second emission wavelength. In certain embodiments, the system comprises a first filter and a second filter (e.g. switchable filters), wherein the first filter is substantially transmissive to the first emission wavelength and substantially opaque to the second emission wavelength, and the second filter is substantially transmissive to the second emission wavelength and substantially opaque to the first emission wavelength.

In certain embodiments, a first polymer optic fiber of the bundle is doped with a first donor dye composition having a first excitation wavelength, a second polymer optic fiber of the bundle is doped with a second donor dye composition having a second excitation wavelength that is different from the first excitation wavelength, the first polymer optic fiber of the bundle has a first binding partner conjugated to its interior surface, and the second polymer optic fiber of the bundle has a second binding partner conjugated to its interior surface, the second binding partner different from the first binding partner. In certain embodiments, the system comprises a first excitation source and a second excitation source, the first excitation source operable to illuminate the fiber bundle at the first excitation wavelength and the second excitation source operable to illuminate the fiber bundle at the second emission wavelength.

In certain embodiments, the detector is a focal plane array comprising a plurality of pixels (e.g. a CCD, a CMOS camera), and emission light from within each polymer optic fiber of the bundle of polymer optic fibers illuminates a different group of pixels of the focal plane array.

In another aspect, the invention is directed to a portable system (e.g. a hand-held system) for detecting a signal from a hollow core polymer optic fiber for single analyte and/or multiple analyte detection, the system comprising: a detector (e.g. a detector responsive to an emission wavelength of an acceptor dye composition with which a polymer optic fiber to be inserted into the system is doped, e.g. a detector responsive to an emission wavelength of an acceptor dye composition with which an acceptor particle to be introduced into a polymer optic fiber is doped); a fiber mount for holding and aligning a polymer optic fiber and/or a bundle of polymer optic fibers in-line with the detector (e.g. such that the fiber and/or bundle is held sufficiently straight, and an axis directed along the fiber and/or bundle is directed to the detector); an excitation source for illuminating the polymer optic fiber and/or bundle of polymer optic fibers with excitation light (e.g. wherein the excitation light comprises light having a wavelength corresponding to an excitation wavelength of a donor dye composition with which a polymer optic fiber to be inserted into the system is doped, e.g. wherein the excitation light comprises light having a wavelength corresponding to an excitation wavelength of a donor dye composition that a donor particle to be introduced into an interior of a polymer optic fiber comprises); and a housing, wherein: the housing surrounds the detector, the fiber mount, and the excitation source, and the housing is substantially opaque to ambient light.

In certain embodiments, the detector is aligned to detect light exiting an end facet of the polymer optic fiber. In certain embodiments, the detector is aligned such that its active area is substantially concentric with an axis of the polymer optic fiber. In certain embodiments, the excitation light source is aligned to illuminate the polymer optic fiber along a length of the polymer optic fiber. In certain embodiments, the excitation light source is aligned to illuminate the polymer optic fiber in a direction perpendicular to the polymer optic fiber. In certain embodiments, the excitation light source is a laser operating at substantially a single wavelength.

In certain embodiments, the housing defines a volume no greater than 750 $cm^3$ (e.g. the system having dimensions no greater than 150 mm by 100 mm by 50 mm). In certain embodiments, a total weight of the system is no greater than 2 lbs. (e.g. a total weight of the system is from 1 to 2 lbs.).

In certain embodiments, the detector is responsive to an emission wavelength of an acceptor dye composition such that the detector detects emission light from a polymer optic fiber and/or an acceptor particle doped with the acceptor dye composition. In certain embodiments, the system comprises a filter positioned in front of the detector, wherein the filter is substantially opaque to light having a wavelength of the excitation light and the filter is substantially transmissive to light having a wavelength corresponding to the an emission wavelength of an acceptor dye composition such that the filter transmits emission light from a polymer optic fiber and/or an acceptor particle doped with the acceptor dye composition.

In certain embodiments, the system comprises a first detector and a second detector, the first detector responsive to a first emission wavelength of a first acceptor dye composition (e.g. with which a first polymer optic fiber and/or first acceptor particle is doped), and the second detector responsive to a second emission wavelength of a second acceptor dye composition (e.g. with which a second polymer optic fiber and/or second acceptor particle is doped), wherein the second emission wavelength is different from the first emission wavelength.

In certain embodiments, the system comprises a first filter and a second filter (e.g. switchable filters), wherein the first filter is substantially transmissive to a first emission wavelength of a first acceptor dye composition (e.g. with which a first polymer optic fiber and/or first acceptor particle is doped) and substantially opaque to a second emission wavelength of a second acceptor dye composition (e.g. with which a second polymer optic fiber and/or second acceptor particle is doped), wherein the second emission wavelength is different from the first emission wavelength, and the second filter is substantially transmissive to the second emission wavelength and substantially opaque to the first emission wavelength.

In certain embodiments, the system comprises a first excitation source and a second excitation source, the first excitation source operable to produce excitation light having a first excitation wavelength corresponding to an excitation wavelength of a donor dye composition (e.g. with which a first polymer optic fiber and/or first donor particle is doped), and the second excitation source operable to produce excitation light having a second excitation wavelength corresponding to an excitation wavelength of a second donor dye composition (e.g. with which a first polymer optic fiber and/or first donor particle is doped), wherein the second excitation wavelength is different from the first excitation wavelength.

In another aspect, the invention is directed to a method for detecting and/or quantifying one or more analytes of interest in a sample, the method comprising: introducing a sample solution into the interior of a polymer optic fiber, the solution comprising the one or more analytes of interest and donor particles, the donor particles comprising a donor dye composition, and a particle binding partner (e.g., a first antibody, e.g. streptavidin), wherein the polymer optic fiber comprises an acceptor dye composition and a fiber binding partner; conducting excitation light through the polymer optic fiber; and detecting emission light traveling through the polymer optic fiber, the emission light produced via singlet oxygen channeling, thereby detecting and/or quantifying the analyte of interest in the sample.

In certain embodiments, the method comprises introducing a sample solution into the interiors of a plurality of polymer optic fibers of a bundle of polymer optic fibers, wherein each polymer optic fiber is doped with a corresponding acceptor dye composition and comprises a corresponding fiber binding partner.

In certain embodiments, each of a plurality of polymer optic fibers of the bundle has a different fiber binding partner (e.g. a different antibody) conjugated to its interior surface (e.g. to allow for detection of different analytes of interest).

In certain embodiments, a first polymer optic fiber of the bundle is doped with a first acceptor dye composition having a first emission wavelength, a second polymer optic fiber of the bundle is doped with a second acceptor dye composition having a second emission wavelength that is different from the first emission wavelength, the first polymer optic fiber of the bundle has a first fiber binding partner conjugated to its interior surface, and the second polymer optic fiber of the bundle has a second fiber binding partner conjugated to its interior surface, the second fiber binding partner different from the first fiber binding partner.

In certain embodiments, the method comprises distinguishably detecting light having a wavelength corresponding to the first emission wavelength and light having a wavelength corresponding the second emission wavelength.

In certain embodiments, the method comprises: introducing into the sample solution a first donor particle comprising a donor dye composition and a first particle binding partner, wherein the first particle binding partner binds to a first analyte to which the first fiber binding partner also binds; introducing into the sample solution a second donor particle comprising a donor dye composition and a second particle binding partner, wherein the second particle binding partner binds to (e.g. is capable of binding to/designed to bind to) a second analyte to which the second fiber binding partner also binds; introducing the sample solution comprising the first donor particle and second donor particle into interiors of the polymer optic fibers of the bundle of polymer optic fibers.

In certain embodiments, the method comprises: (a) introducing into the sample solution a first donor particle comprising a first donor dye composition and a first particle binding partner, wherein the first particle binding partner binds to a first analyte; (b) introducing into the sample solution a second donor particle comprising a second donor dye composition and a second particle binding partner, wherein the second particle binding partner binds to (e.g. is capable of binding to/designed to bind to) a second analyte; (c) introducing the sample solution comprising the first donor particle and second donor particle into interiors of the polymer optic fibers of the bundle, wherein: a first polymer optic fiber of the bundle has a first fiber binding partner conjugated to its interior surface, a second polymer optic fiber of the bundle has a second fiber binding partner conjugated to its interior surface, the second binding partner different from the first binding partner, the first fiber binding partner binds to the first analyte, and the second fiber binding partner binds to the second analyte; (d) illuminating the fiber bundle with excitation light having a first wavelength corresponding to an excitation wavelength of the first donor dye composition and detecting resultant emission light; and (e) illuminating the fiber bundle with excitation light having a second wavelength corresponding to an excitation wavelength of the second donor dye composition and detecting resultant emission light.

In another aspect, the invention is directed to a method for detecting and/or quantifying one or more analytes of interest in a sample, the method comprising: introducing a sample solution into the interior of a polymer optic fiber, the solution comprising one or more analytes of interest and acceptor particles, the acceptor particles comprising an acceptor dye composition and a particle binding partner (e.g., a first antibody), wherein the polymer optic fiber comprises a donor dye composition and a fiber binding partner (e.g., a second antibody); conducting excitation light through the polymer optic fiber; and detecting emission light traveling through the polymer optic fiber, the emission light produced via singlet oxygen channeling, thereby detecting and/or quantifying the analyte of interest in the sample.

In certain embodiments, the method comprises introducing a sample solution into the interiors of a plurality of polymer optic fibers of a bundle of polymer optic fibers, wherein each polymer optic fiber is doped with a corresponding donor dye composition and comprises a corresponding fiber binding partner.

In certain embodiments, each of a plurality of polymer optic fibers of the bundle of polymer optic fibers has a different fiber binding partner (e.g. a different antibody) conjugated to its interior surface (e.g. to allow for detection of different analytes of interest).

In certain embodiments, the method comprises: introducing into the sample solution a first acceptor particle comprising a first acceptor dye composition and a first particle binding partner, wherein the first acceptor dye composition has a first emission wavelength; introducing into the sample solution a second acceptor particle comprising a second acceptor dye composition and a second particle binding partner, wherein the second acceptor dye composition has a second emission wavelength that is different from the first emission wavelength, and the second particle binding partner is different from the first particle binding; introducing the sample solution comprising the first acceptor particle and second acceptor particle into interiors of the polymer optic fibers of the bundle, wherein: one or more polymer optic fibers of the bundle have a first fiber binding partner conjugated to an interior surface, wherein the first fiber binding partner binds to a first analyte to which the first particle binding partner also binds, and one or more polymer optic fibers of the bundle have a second fiber binding partner conjugated to an interior surface, wherein the second fiber binding partner binds to a second analyte to which the second particle binding partner also binds.

In certain embodiments, the method comprises distinguishably detecting light having a wavelength corresponding to the first emission wavelength and light having a wavelength corresponding to the second emission wavelength.

In certain embodiments, the method comprises: (a) introducing into the sample solution a first acceptor particle comprising a first particle binding partner, wherein the first particle binding partner binds to a first analyte; (b) introducing into the sample solution a second acceptor particle comprising a second particle binding partner, wherein the second particle binding partner binds to (e.g. is capable of binding to/designed to bind to) a second analyte; (c) introducing the sample solution comprising the first acceptor particle and second acceptor particle into interiors of the polymer optic fibers of the bundle, wherein: a first polymer optic fiber of the bundle is doped with a first donor dye composition and has a first fiber binding partner conjugated to its interior surface, a second polymer optic fiber of the bundle is doped with a second donor dye composition and has a second fiber binding partner conjugated to its interior surface, the second binding partner different from the first binding partner, the first fiber binding partner binds to the first analyte, the second fiber binding partner binds to the second analyte, (d) illuminating the fiber bundle with excitation light having a first wavelength corresponding to an excitation wavelength of the first donor dye composition and detecting resultant emission light; and (e) illuminating the fiber bundle with excitation light having a second wavelength corresponding to an excitation wavelength of the second donor dye composition and detecting resultant emission light.

In certain embodiments, introducing the sample solution into the interior of the polymer optic fiber comprises immersing the polymer optic fiber into the sample solution such that the sample solution is drawn into the interior of the polymer optic fiber via capillary action.

In certain embodiments, the particle binding partner binds to at least a first analyte of the one or more analytes of interest and the fiber binding partner also binds to the first analyte.

In certain embodiments, the polymer optic fiber comprises multiple discrete portions along its length, each of which portions has a different concentration of the first or second binding partner conjugated to its interior surface for achieving a variety of levels of sensitivity of measurement of the analyte of interest. In certain embodiments, the polymer optic fiber comprises multiple discrete portions along its length, each of which portions has a different binding partner (e.g., different antibody) conjugated to its interior surface.

In another aspect, the invention is directed to a kit comprising: a polymer optic fiber as described herein; and one or more reagents for preparation of a sample for detection of one or more analytes of interest, the one or more reagents comprising acceptor particles (e.g., acceptor beads) and/or donor particles (e.g., donor beads).

In another aspect, the invention is directed to a kit comprising: a bundle of polymer optic fibers as described herein; and one or more reagents for preparation of a sample for detection of one or more analytes of interest, the one or more reagents comprising acceptor particles (e.g., acceptor beads) and/or donor particles (e.g., donor beads).

In another aspect, the invention is directed to a kit comprising: a cartridge as described herein; and one or more reagents for preparation of a sample for detection of one or more analytes of interest, the one or more reagents comprising acceptor particles (e.g., acceptor beads) and/or donor particles (e.g., donor beads).

In another aspect, the invention is directed to a method of manufacturing a polymer optic fiber doped with an acceptor dye composition, the method comprising: contacting an interior surface of the polymer optic fiber with a chemiluminescent singlet oxygen acceptor (e.g. thioxene) and at least one of: (i) a fluorescent compound (e.g. a lanthanide chelate, e.g. an organic dye) and (ii) quantum dots.

In another aspect, the invention is directed to a method of manufacturing a polymer optic fiber doped with a donor dye composition, the method comprising: contacting an interior surface of the polymer optic fiber with a photosensitizer.

The description of elements of one aspect of the invention (e.g., features of a system) can be applied as elements of another aspect of the invention (e.g., features of an apparatus or a method) as well.

BRIEF DESCRIPTION OF THE DRAWINGS

The objects and features of the invention can be better understood with reference to the drawings described below, and the claims.

DETAILED DESCRIPTION

Figure 1:
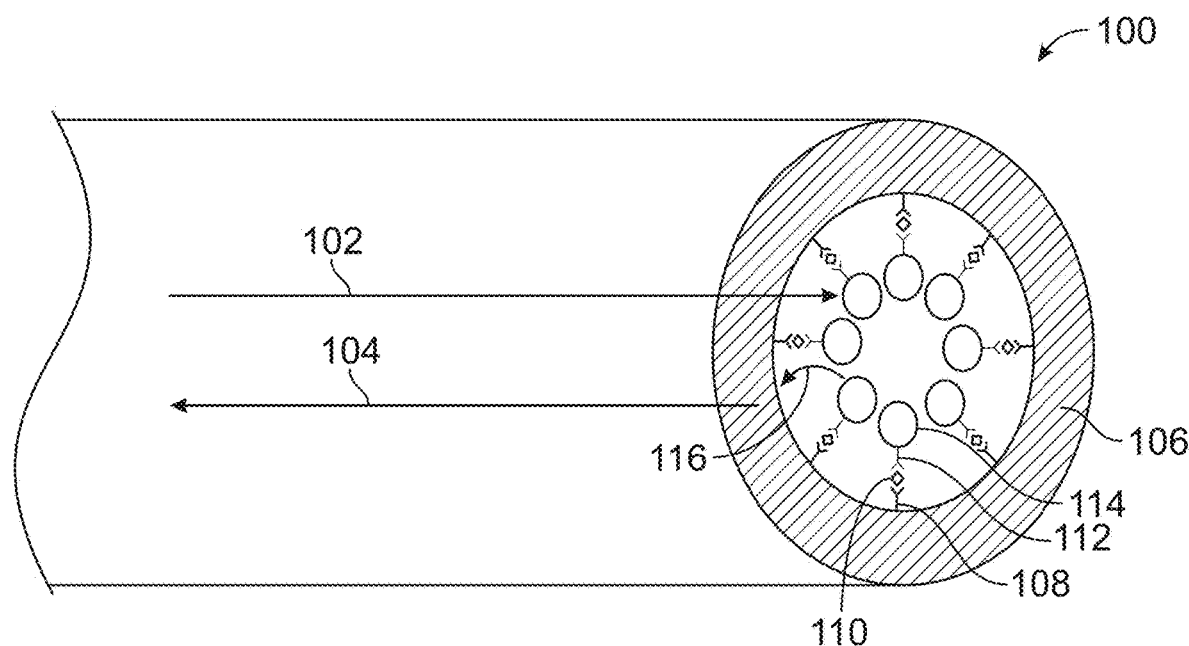
FIG. 1 is a schematic depicting a hollow polymer optic fiber doped with acceptor dye, for use in the analyte detection systems described herein, according to an illustrative embodiment.

It is contemplated that apparatus, systems, methods, and processes of the present disclosure encompass variations and adaptations developed using information from the embodiments described herein. Adaptation and/or modification of the apparatus, systems, methods, and processes described herein may be performed by those of ordinary skill in the relevant art.

Throughout the description, where systems are described as having, including, or comprising specific components, or where processes and methods are described as having, including, or comprising specific steps, it is contemplated that, additionally, there are systems of the present disclosure that consist essentially of, or consist of, the recited components, and that there are processes and methods according to the present disclosure that consist essentially of, or consist of, the recited processing steps.

It should be understood that the order of steps or order for performing certain actions is immaterial so long as the process remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Subject headers are provided herein for convenience only. They are not intended to limit the scope of embodiments described herein.

Where a specific chemical species is referenced herein, it is understood to include a suitably substituted or unsubstituted version of the species, as well as suitably metalated versions comprising, e.g. zinc, copper, aluminum, silicon, titanium, iron manganese, cobalt, and nickel.

The present disclosure relates to methods, systems, and apparatus for single analyte detection or multiplexed analyte detection based on existing amplified luminescent proximity homogeneous assay ("alpha") technology, but which utilize hollow polymer fiber optics doped with compounds that are presently used for "acceptor beads" (e.g., thioxene, anthracene, rubrene, and/or lanthanide chelates) or "donor beads" (e.g., phthalocyanine) in existing alpha systems. The polymer fiber optics carry a signal generated by the dopant via singlet oxygen channeling, which is detected and used to identify the presence and/or quantity of an analyte or multiple analytes of interest in a given sample.

I. Hollow Core Polymer Optic Fibers

The polymer fiber optics are embedded with known chemicals that allow luminescent oxygen channeling to occur in the proximity of complementary nanoparticles. The polymer fibers can be made of polystyrene and/or poly (methyl methacrylate) (PMMA), for example, as used in the telecommunications industry. In certain embodiments, the fibers are short (e.g., less than 5 cm, less than 3 cm, less than 2 cm, or between 1 and 3 cm). In certain embodiments, the fibers are very narrow, e.g., the fibers each have interior diameter (ID) of from 0.1 to 2 mm, e.g. from 0.5 to 2 mm, e.g., from 1 to 1.5 mm, and/or an outer diameter (OD) of from 1 to 3 mm, e.g., from 1.5 to 2 mm.

In certain embodiments, the dimensions of a fiber are such that the fiber is capable of drawing liquid (e.g. a sample solution comprising a sample to be tested) into its interior via capillary action. In certain embodiments, the fibers each have an interior diameter that preserves capillarity such that liquid (e.g., a solution comprising a sample) is drawn into the interior of the polymer optic fiber by capillary action.

In certain embodiments, the fibers have multiple hollow cores (e.g. 5 to 20 hollow cores). In certain embodiments, each hollow core of a fiber having multiple hollow cores has an interior diameter (ID) of from 0.1 to 2 mm, e.g. from 0.5 to 2 mm, e.g., from 1 to 1.5 mm. In certain embodiments, the dimensions of each hollow core are such that the fiber is capable of drawing liquid (e.g. a sample solution comprising a sample to be tested) into its interior (e.g. into each hollow core) via capillary action. In certain embodiments, each hollow core of a fiber has an interior diameter that preserves capillarity such that liquid (e.g., a solution comprising a sample) is drawn into the interior of the polymer optic fiber by capillary action.

The polymer fibers can be doped using known techniques, e.g., polymer swelling in solution of dye, following by rapid cooling to contract polymer and trap dye in the polymer matrix. Furthermore, in certain embodiments, the dopant can be introduced during manufacture of the polymer fiber, rather than afterwards.

Depending on the embodiment, a given polymer fiber can be doped with an alpha technology "acceptor" dye—e.g., thioxene, anthracene, rubrene, and/or lanthanide chelate, e.g., europium chelate, terbium chelate, dysprosium chelate, samarium chelate, ytterbium chelate, erbium chelate, and/or thulium chelate, and/or variations thereof—or an alpha technology "donor" dye—e.g., phthalocyanine, naphthalocyanine, a chlorin, a phorphin, a phorphyrin, stellacyanin, chlorophyll, rose bengal, and/or variations thereof.

In certain embodiments, a polymer optic fiber is doped with an acceptor dye composition comprising a chemiluminescent singlet oxygen acceptor (e.g. thioxene) and a fluorescent compound (e.g. an organic dye (e.g. anthracene, rubrene), a lanthanide chelate (e.g. comprising a lanthanide such as europium, terbium, dysprosium, samarium, ytterbium, erbium, and thulium).

Without wishing to be bound to a particular theory, in certain embodiments, the chemiluminescent singlet oxygen acceptor (e.g. thioxene) reacts with singlet oxygen, and produces ultraviolet light (e.g. light having a wavelength of 340 nm). The fluorescent compound is excited by the ultraviolet light produced by the chemiluminescent singlet oxygen acceptor via its reaction with singlet oxygen, and emits fluorescent light. In certain embodiments, energy is transferred from the chemiluminescent singlet oxygen acceptor to the fluorescent compound directly, via a Förster resonance energy transfer (FRET) mechanism. The transfer of energy from the chemiluminescent singlet oxygen acceptor to the fluorescent compound excites the fluorescent compound, resulting in the emission of fluorescent light.

In certain embodiments, the fiber is doped with quantum dots (e.g. fluorescent quantum dots). In certain embodiments, the fiber is doped with quantum dots and an acceptor dye composition comprising a chemiluminescent singlet oxygen acceptor. In certain embodiments the quantum dots emit fluorescent light following excitation by ultraviolet light emission produced by a reaction of the chemiluminescent singlet oxygen acceptor with singlet oxygen. In certain embodiments the fiber is doped with quantum dots and an acceptor dye composition comprising a chemiluminescent singlet oxygen acceptor and a fluorescent compound (e.g. a lanthanide chelate).

In certain embodiments, the interior of the hollow fiber is coated and functionalized, as would be a donor bead or acceptor bead in existing alpha technology systems. For example, the hollow fiber may comprise a core of polystyrene, surrounded by dextran (e.g., two or more layers of dextran), the outermost layer of dextran participating in the bioconjugation. The coating can be functionalized with —NH$_2$, —SH, —COH, —COOH, and/or —CO—OR groups. The coating keeps dyes from leaching out of the polymer.

In certain embodiments, groups of thusly doped/coated polymer fibers are assembled into modules or cassettes, e.g., for use in multiplexed analyte detection systems.

In certain embodiments, the systems require an excitation light source and a detector. The excitation light source in a hand-held or lab/bench detector can include, for example, a laser, light-emitting diode (LED), or lamp. The detector for a hand-held or lab/bench detector can include, for example, a charge-coupled device (CCD), photomultiplier tube (PMT), and/or avalanche photodiode (APD). Existing detector systems can be used or adapted for use in reading signals from the hollow fibers described herein, e.g., monochromator-based absorbance, fluorescence, and/or luminescence detectors/readers.

I.A Analyte Detection with Acceptor Dye Doped Fibers

FIG. 1 is a schematic depicting an embodiment of system 100 comprising a hollow polymer optic fiber 106 doped with acceptor dye. A first binding partner 108 (e.g., antibody, depicted as the "Y" shapes with thick lines in FIG. 1) is conjugated on the interior surface of the fiber. In the depicted embodiment, a solution of the sample containing the analyte of interest 110 (depicted as the small diamonds in FIG. 1) is prepared, and donor beads 114 (depicted as circular shapes), e.g., streptavidin-coated donor beads embedded with 'donor dye' such as phthalocyanine, are added to the solution. A second binding partner 112 (e.g., a second antibody, depicted as the "Y" shapes with thin lines in FIG. 1), e.g., which is biotinylated, is coupled to the donor beads. The solution is drawn into the optic fiber (e.g., via capillary force). The analyte 110 is captured by the antibody pair to create a sandwich assay. In certain embodiments, the biotinylated antibody (second antibody) binds to an epitope on the analyte, and the first antibody binds to a different epitope. The streptavidin and biotin pulls the complex together, bringing the donor beads into proximity.

The hollow fiber 106 is placed into a reader and is exposed to excitation light 102 (e.g., from a laser), e.g., laser light at 680 nm wavelength is sent through the fiber. Excitation causes release of singlet oxygen 116 by the donor beads 114, which travels up to about 200 nm, allowing analysis of large complex molecules. When the donor particles are brought into proximity to the 'acceptor' hollow fibers by a molecular interaction of interest (e.g., antigen-IgG interaction), then, upon exposure to excitation light, lanthanide fluorescence 104 (or other acceptor dye fluorescence) is produced in the cladding. Light emission 104 of the acceptor dye in the polymer fiber 106 results when the analyte 110 is present; the intensity of the light emission is a function of (e.g., proportional to) the analyte concentration.

Figure 13:
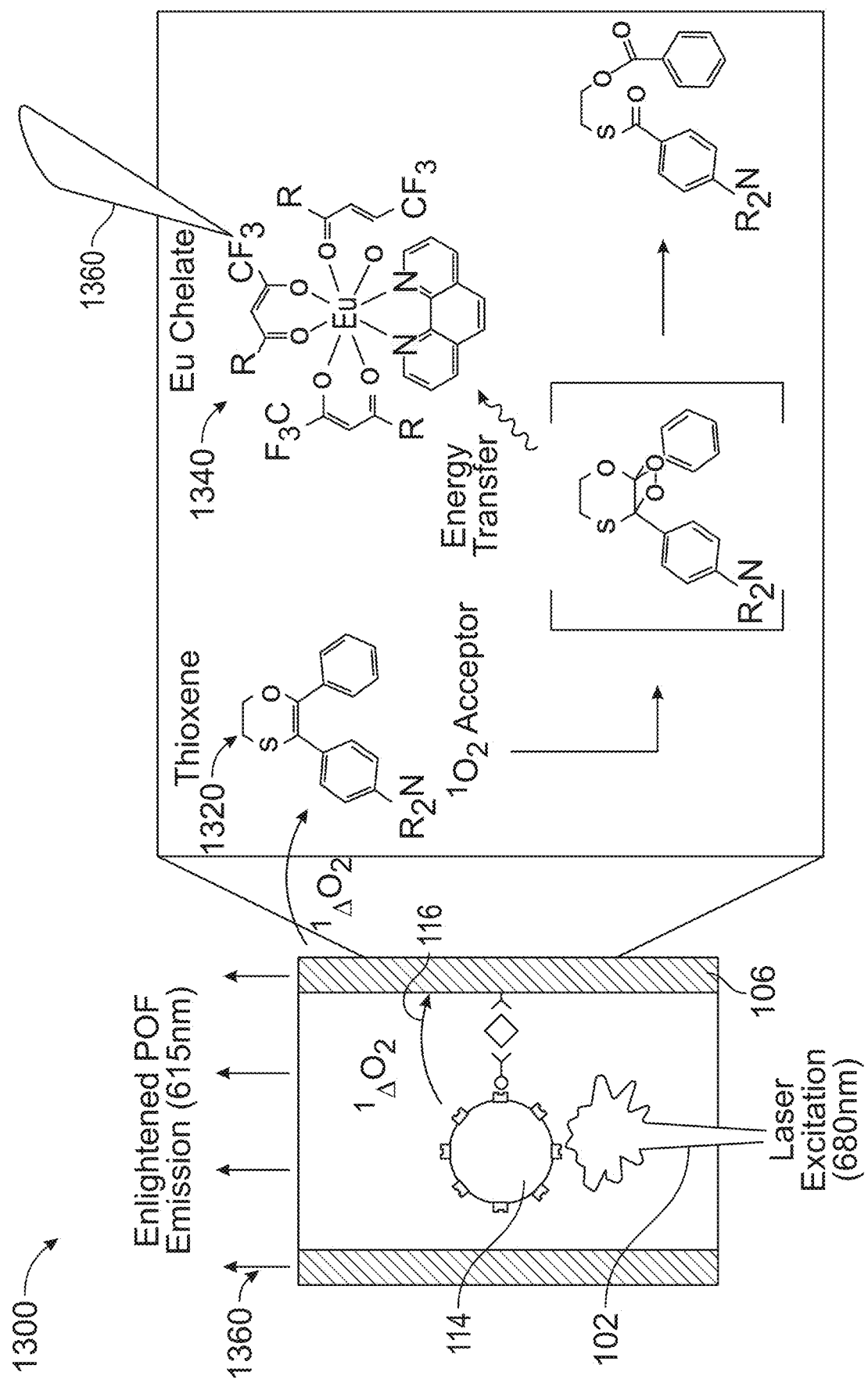
FIG. 13 is a schematic depicting the excitation of a donor dye doped bead and the emission of light from an acceptor dye, according to an illustrative embodiment.

FIG. 13 is another schematic depicting an example system 1300 comprising a hollow polymer optic fiber 106 doped with an acceptor dye composition. FIG. 13 shows, similar to FIG. 1, a donor bead 114 within the hollow polymer optic fiber. The donor bead 114 is brought into proximity with the interior of an acceptor dye doped hollow polymer optic fiber 106 by virtue of a molecular interaction of interest between a first binding partner, bound to the interior surface of the fiber 106, an analyte of interest, and a second binding partner that is coupled to the donor bead 114. Upon exposure to excitation light 102 (e.g. laser excitation at a wavelength of 680 nm), the donor bead releases singlet oxygen 116, which causes the emission of light 1360 from the acceptor dye doped fiber 106. In particular, in the example shown in FIG. 13, the fiber is doped with an acceptor dye composition comprising thioxene 1320 and a europium chelate 1340. The europium (Eu) chelate 1340 is directly excited by the 340 nm light resulting from the conversion of thioxene 1320 to a di-ketone derivative following its reaction with singlet oxygen. The excited europium chelate 1340 generates an intense light 1360 detectable within a narrow wavelength bandwidth centered around 615 nm.

FIG. 1 depicts emitted light 102 at a wavelength (e.g., between 520 nm and 620 nm, e.g., 615 nm) that is different (and distinguishable) from the wavelength of the excitation light 104. The emitted light is detected and the presence of the analyte is determined, and/or the amount of the analyte in the sample is quantified based on the detected light signal.

The beads described herein can be made with organic or inorganic materials, for example, glass, metal, latex, synthetic or naturally occurring polymer, such as polystyrene, polycarbonate, silicon, nylon, cellulose, agarose, dextran, and polyacrylamide. Particles may be latex beads. In certain embodiments, the beads are millimeter scale, micro-scale, or nano-scale. In certain embodiments, particles other than bead shapes are used.

The particles used in bead analysis may include functional groups for binding to amplicons. For example, in certain embodiments, particles can include carboxyl, amine, amino, carboxylate, halide, ester, alcohol, carbamide, aldehyde, chloromethyl, sulfur oxide, nitrogen oxide, epoxy and/or tosyl functional groups. Binding amplicons to the particles results in encoded particles.

In certain embodiments, the system sends a laser pulse at 680 nm (or other excitation wavelength) to excite phthalocyanine-embedded cladding (or embedded polystyrene nanoparticles) and generates singlet oxygen. The hollow fiber carries a signal generated by embedded nanoparticles or cladding that contain lanthanide chelates excited through singlet oxygen channeling. In certain embodiments, the wavelength of the excitation light is 775 nm, corresponding to an excitation wavelength of napthalocyanine (another example of a photosensitizer).

In certain embodiments, the emission wavelength depends on the choice of an acceptor dye composition. For example, europium emits at a wavelength of 615 nm, dysprosium emits at a wavelength of 575 nm, samarium emits at a wavelength of 645 nm, and terbium emits at a wavelength of 545 nm.

I.B Analyte Detection with Donor Dye Doped Fibers

Figure 2:
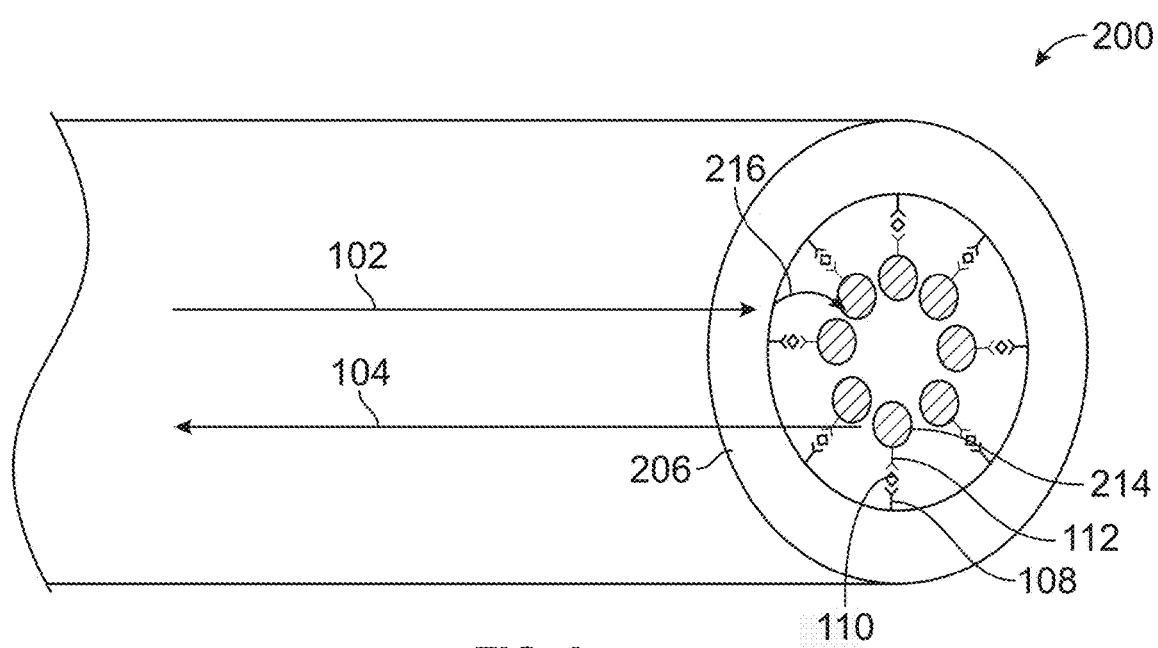
FIG. 2 is a schematic depicting a hollow polymer optic fiber doped with donor dye, for use in the analyte detection systems described herein, according to an illustrative embodiment.

FIG. 2 is a schematic depicting a system 200 comprising a hollow polymer optic fiber 206 doped with donor dye, and is a variation on the embodiments shown in FIG. 1. In certain embodiments, the fiber is doped with a donor dye composition comprising a photosensitizer (e.g. phthalocyanine, naphthalocyanine, a chlorin, a phorphin, a phorphyrin, stellacyanin, chlorophyll, and/or rose bengal) that releases singlet oxygen when illuminated with excitation light (e.g. light having a wavelength in the visible spectrum, e.g. light having a wavelength in the near-infrared spectrum, e.g. light having a wavelength of 680 nm, e.g. light having a wavelength of 775 nm).

In FIG. 2, a hollow polymer 'donor' optic fiber 206 doped with donor dye (e.g., phthalocyanine) is coated with a binding partner 108 (e.g., antibody, shown as Y shapes in FIG. 2). 'Acceptor' nanoparticles 214 (e.g., polystyrene beads, shown as circular shapes in FIG. 2) embedded with acceptor dye (e.g., thioxene and/or lanthanide chelate(s)) are coated with a different binding partner 112 (e.g., different antibody). When the acceptor nanoparticles are brought into proximity to the 'donor' hollow fiber by a molecular interaction of interest (e.g., antigen-IgG interaction), fluorescence produced by the acceptor nanoparticles (e.g., lanthanide fluorescence) results from excitation of the donor optic fiber by excitation light (e.g., at an excitation wavelength, e.g., 680 nm, e.g. 775 nm). Excitation of the donor optic fiber triggers the release of singlet oxygen 216 by the donor fiber. When the acceptor particles 214 are brought into proximity to the donor hollow fibers 216 by a molecular interaction of interest (e.g., antigen-IgG interaction), then, upon exposure to excitation light, lanthanide fluorescence 104 (or other acceptor dye fluorescence) is produced by the acceptor particles. Light emission 104 of the acceptor dye in the acceptor particles 214 results when the analyte 110 is present; the intensity of the light emission is a function of (e.g., proportional to) the analyte concentration. The emitted light is detected and the presence and/or concentration of analyte is determined.

I.C Multiplexing Via Polymer Optic Fiber Bundles

Figure 3:
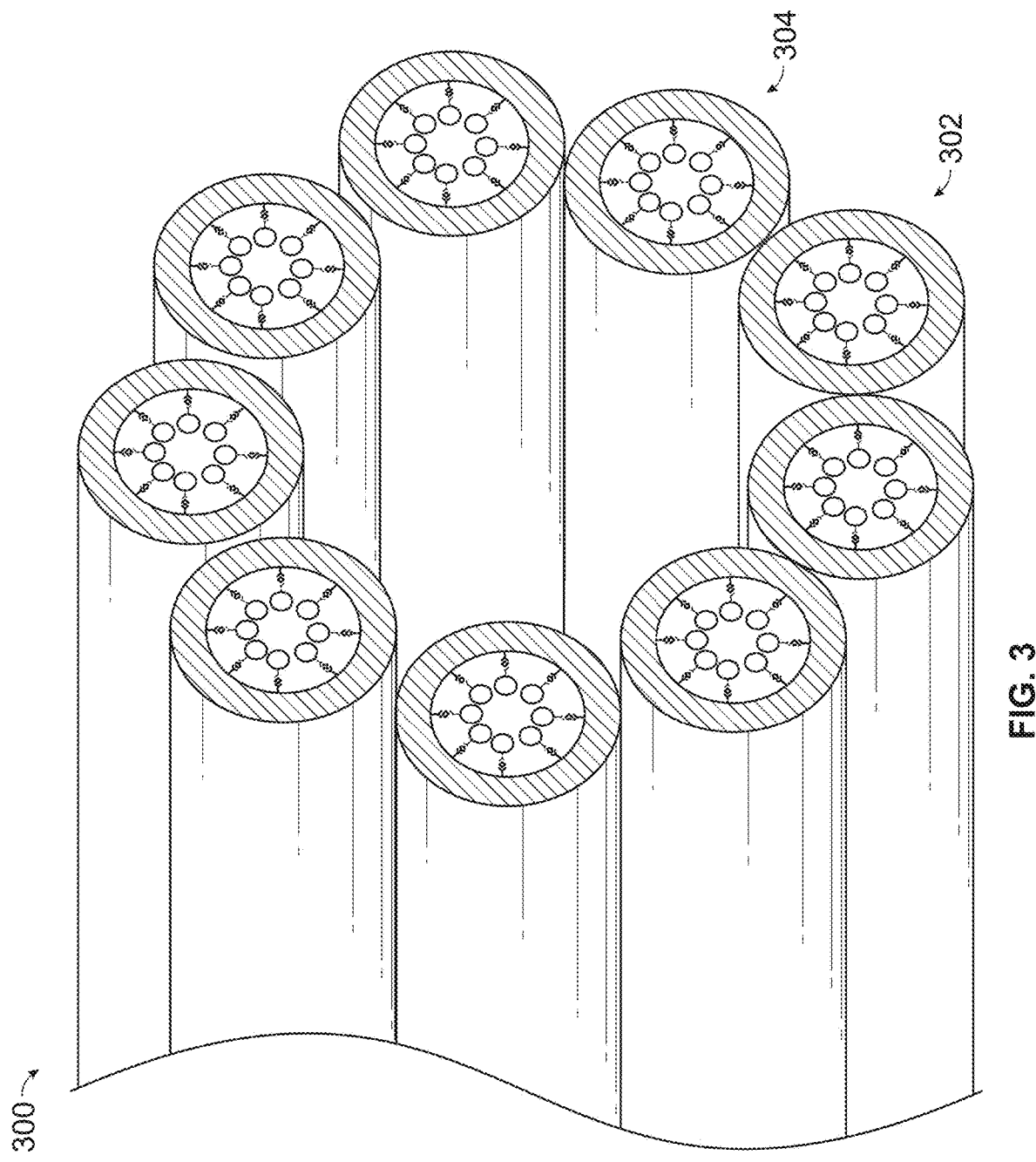
FIG. 3 is a schematic depicting a bundle of optic fibers, such as the fiber shown in FIG. 1, where each fiber is doped with acceptor dye, according to an illustrative embodiment.

FIG. 3 is a schematic depicting a bundle 300 of optic fibers (e.g. comprising from 1 to 20 fibers), such as the fiber shown in FIG. 1, where each fiber is doped with "acceptor" dye. Multiple acceptor dyes can be used (e.g., different dyes in different fibers) such that emitted light produced as described above with respect to FIG. 1 can be distinguished and, thus, the presence and/or concentration of multiple analytes can be determined. In certain embodiments, the binding partners may be different from fiber to fiber, and there may be other composition differences from fiber to fiber, allowing for more optimized multiplexing analyte detection.

Figure 4:
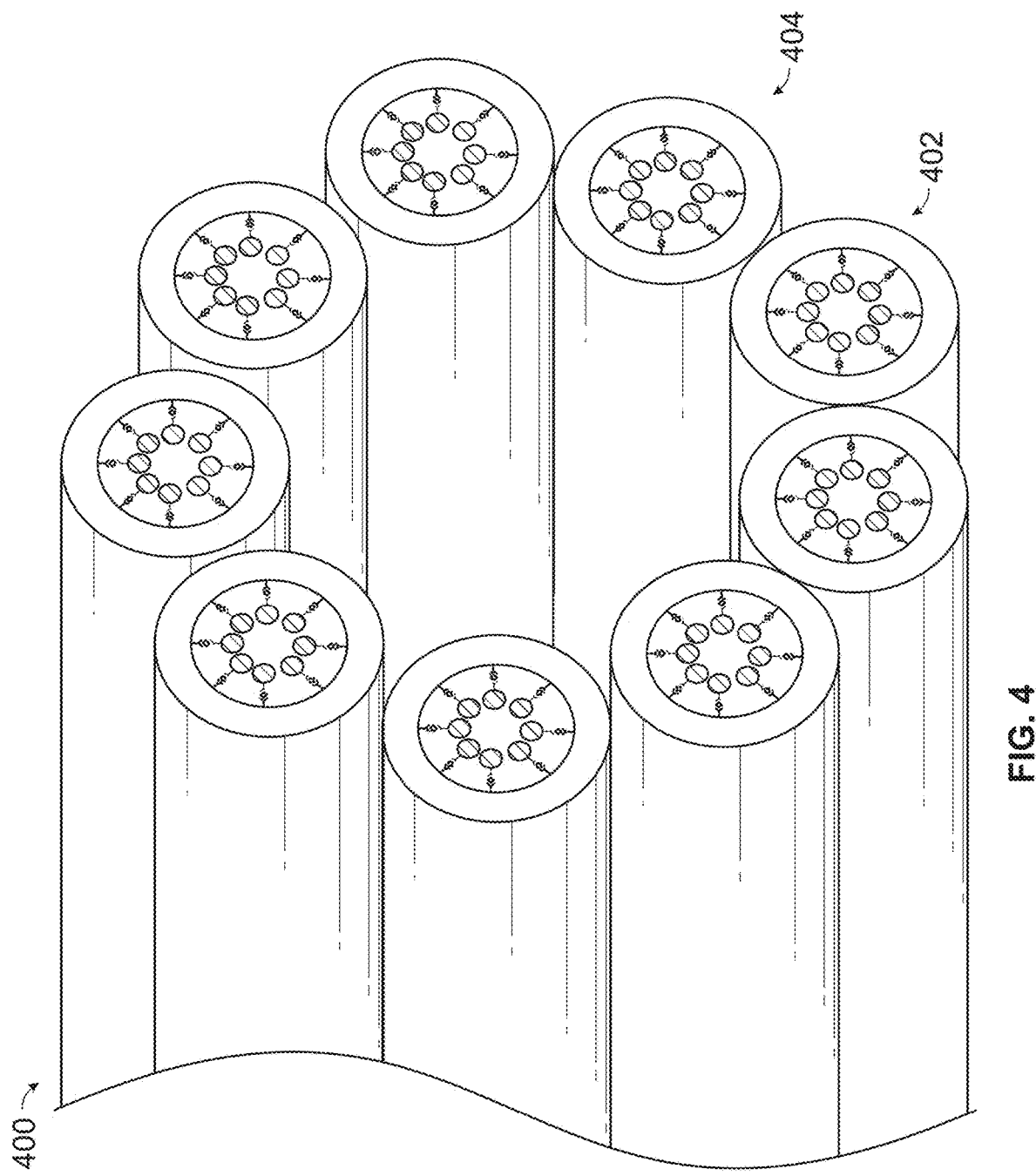
FIG. 4 is a schematic depicting a bundle of optic fibers, such as the fiber shown in FIG. 2, where each fiber is doped with donor dye, according to an illustrative embodiment.

FIG. 4 is a schematic depicting a bundle 400 of optic fibers, such as the fiber shown in FIG. 2, where each fiber is doped with "donor" dye. The donor dyes, binding partners in the fiber, as well as different acceptor beads and compositions can be varied to produce distinguishable signals, allowing for multiplexed analyte detection.

I.D Multiplexing Via a Single Polymer Optic Fiber

Figure 5:
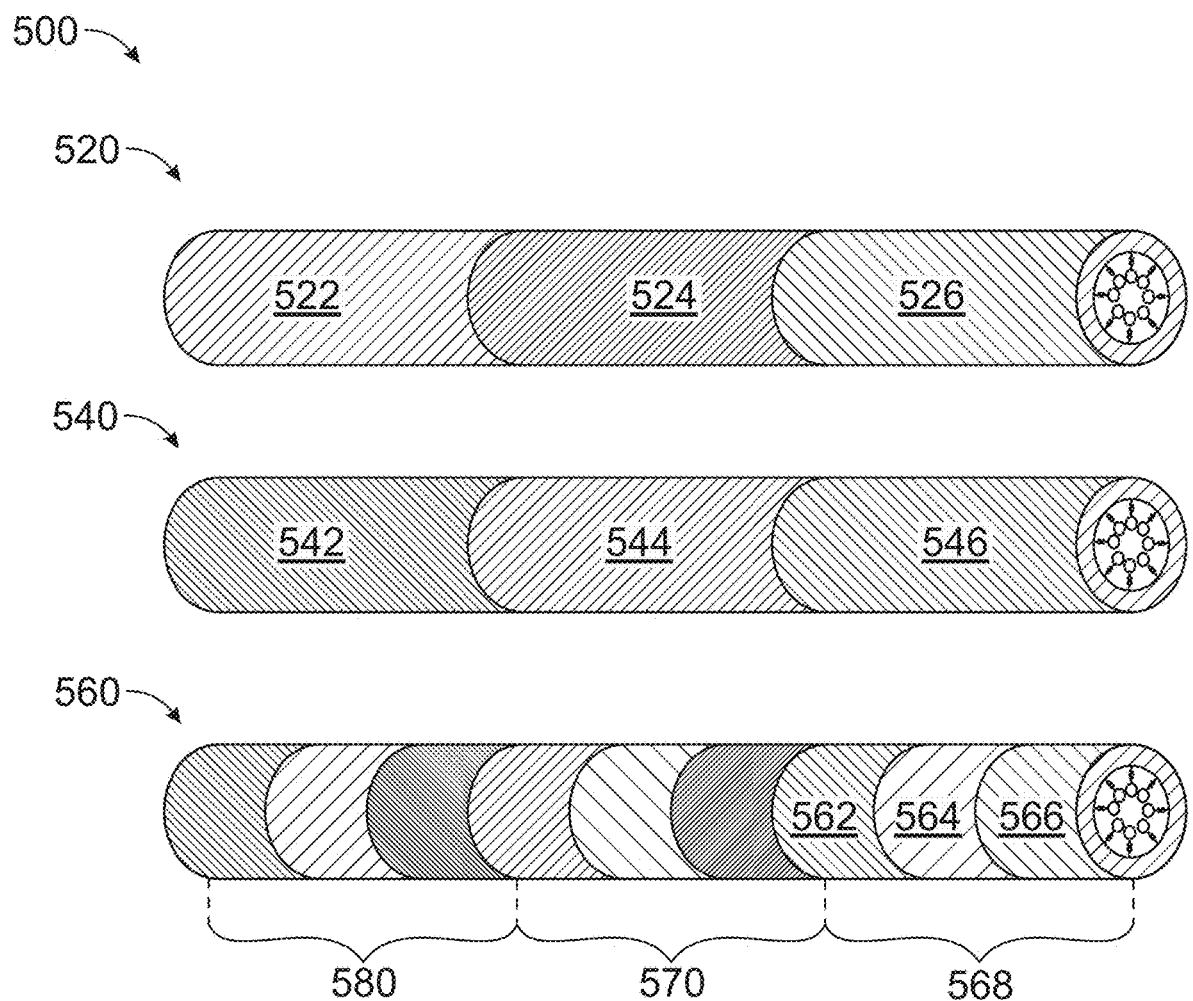
FIG. 5 is a schematic depicting how doping of the hollow fiber can be varied to achieve various levels of sensitivity and to allow for multiplexing between different variants of specific antigens, according to an illustrative embodiment.

FIG. 5 is a schematic depicting different examples of hollow polymer optic fibers (collectively 500). The different examples illustrate how different configurations of multiple binding partners and/or different concentrations of binding partners conjugated to an interior surface of a hollow fiber can be varied to achieve various levels of sensitivity and to allow for multiplexing between different variants of specific antigens. For example, in certain embodiments, different segments (e.g. a first segment 522, a second segment 524, and a third segment 526) of a fiber 520 are coated with various concentrations (e.g. surface concentrations) of binding partners (e.g., IgG) to achieve various levels of sensitivity, e.g., down to picogram per mL. In certain embodiments, different binding partners can be used in different sections of a given fiber 540 to allow for detection of different variants of specific antigens. For example, a first section 542 of a fiber 540 is coated with a first binding partner that binds to a first variant, a second section 544 of the fiber 540 is coated with a second binding partner that binds to a second variant, and a third section 546 of the fiber 540 is coated with a third binding partner that binds to a third variant.

Furthermore, in certain embodiments, both variation in binding partner type and ratio is used in a given fiber 560 to allow multiplexed analyte detection over a wide range of concentrations. For example, a first section 568 of a fiber 560 comprises three subsections 562, 564, 566, each coated with a different binding partner that binds to a different variant of an analyte of interest. In the first section 562 of the fiber, each of the three subsections comprise a first ratio (e.g. a high ratio) of the respective binding partner. Other sections of the fiber 570, 580, also each comprise three subsections, each coated with the same binding partners as the subsections of the first section 568, but at different ratios.

I.E Fiber Bundle Cartridges

Figure 6:
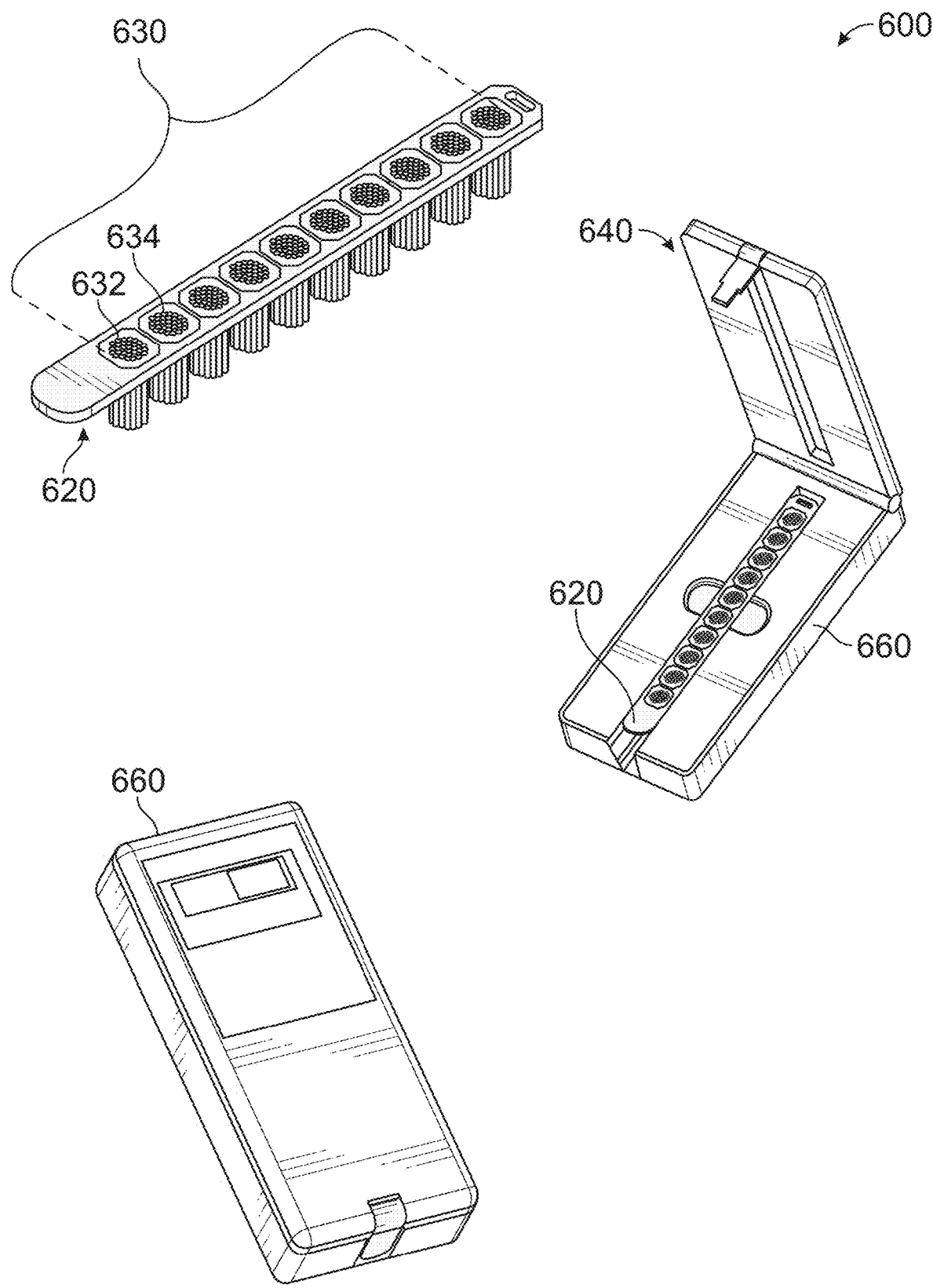
FIG. 6 is a schematic depicting a cartridge comprising an array of bundles of polymer optic fibers, according to an illustrative embodiment.

FIG. 6 is a schematic depicting an example system 600 comprising a cartridge 620 comprising a plurality (e.g. 8 to 10) of fiber bundles (collectively 630). In certain embodiments, the cartridge of fiber bundles is used for multiplexed detection of analytes in multiple samples. For example, for a given bundle, e.g. 632 or 634, of fibers, different fibers in the bundle can be doped with different acceptor dye compositions, and conjugated with different binding partners in order to detect the presence and/or concentration of multiple analytes in the manner described above with respect to FIG. 3. Similarly, in another example, each fiber in a bundle of fiber can be doped with a donor dye composition, and different acceptor beads can be used in order to detect the presence and/or concentration of multiple analytes in the manner described above with respect to FIG. 4.

In certain embodiments, each bundle of fibers in a cartridge can be used for multiplexed analyte detection in a different sample. Accordingly, a single cartridge 620 can be used to detect multiple analytes in multiple samples. In certain embodiments, each fiber bundle in the cartridge has the same kinds of fibers (same set of fibers) as the other bundles—e.g. for each fiber bundle of the cartridge, the particular configuration of dyes (e.g. acceptor dyes or donor dyes) with which the fibers of the bundle are doped and the particular configuration of binding partners conjugated to the interior surfaces of the fibers of the bundle, are the same as for the other fiber bundles in the cartridge.

In certain embodiments, two or more fiber bundles in the cartridge are of different types (e.g. having different configurations of dyes and binding partners for the fibers of each bundle). Accordingly, a single cartridge, comprising multiple bundles of different types, can be used for multiplexed detection of multiple analytes in a sample. In certain embodiments, each bundle of a cartridge is contacted with a portion of the same sample for multiplexed detection of multiple analytes in the sample.

In certain embodiments the cartridge 620 can be placed (640) into a cartridge reader 660 of the system that provides for switching between the fiber bundles, allowing signal from each bundle to be detected in a convenient fashion.

II. Detection Systems for Polymer Optic Fibers

II.A Detection System Components

Figure 7:
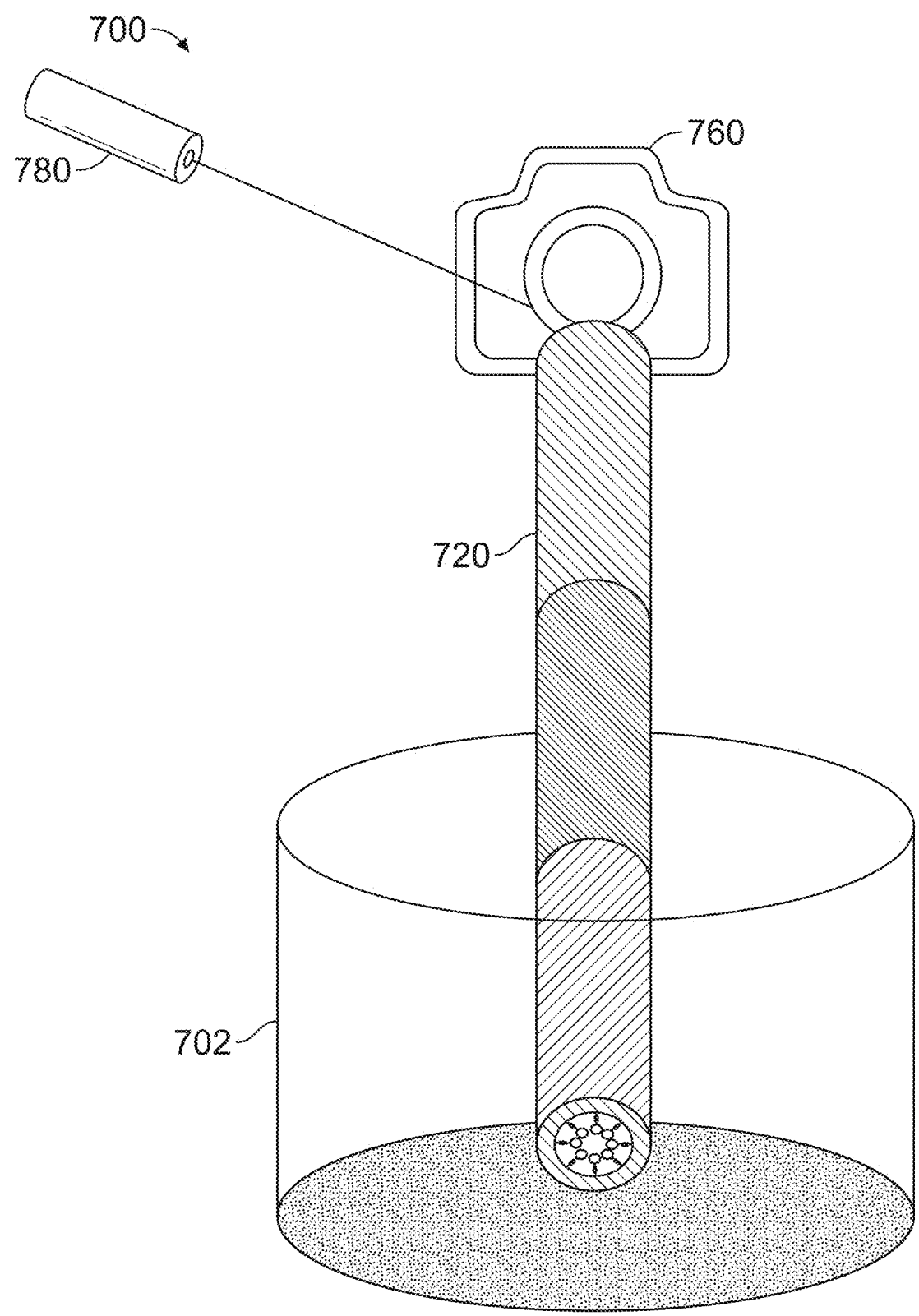
FIG. 7 is a schematic diagram of an example system 700 for single analyte and/or multiple analyte detection using the hollow polymer optic fibers described herein, according to an illustrative embodiment.

FIG. 7 is a schematic diagram of an example system 700 for single analyte and/or multiple analyte detection using the hollow polymer optic fibers described herein. The sample, beads, and reagents (e.g., from a microplate well, a vial, or other container) 702 are introduced to the interior of the hollow fiber 720—e.g., the solution is drawn up the hollow fiber through capillary force. A laser diode 780 (or other light source) provides excitation light, and a detector 760 (e.g., including a CCD, PMT, and/or APD) measures the emitted light traveling through/along the optic fiber, thereby identifying the presence and/or concentration of each of one or more analytes in the sample.

Figure 8A:
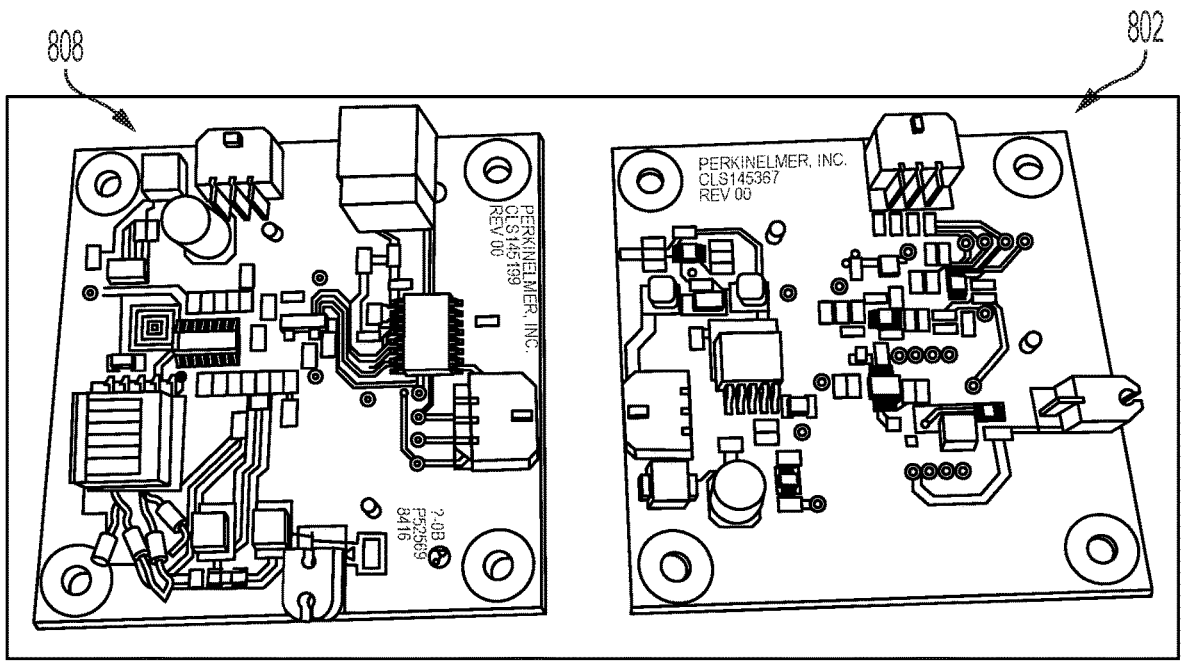
FIG. 8A is an image of a power supply and an electronics board comprising a photodetector system for detecting and analyzing signal from the hollow polymer optic fiber system, according to an illustrative embodiment.
Figure 8B:
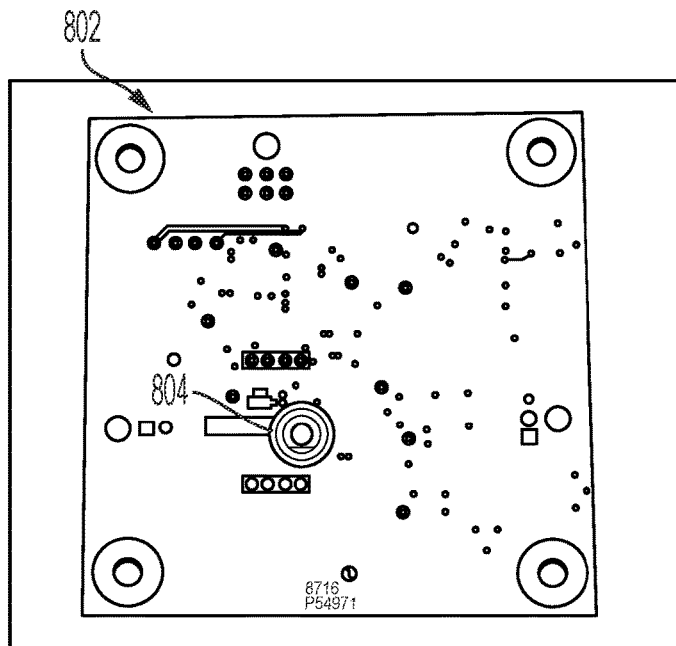
FIG. 8B is an image of an electronics board comprising a photodetector for detecting and analyzing signal from the hollow polymer optic fiber system, according to an illustrative embodiment

FIG. 8A is an image of a set of components for detecting and analyzing signals from the hollow fiber system described herein. The components include an detection electronics board 802 comprising a detector and a power supply 808. FIG. 8B is an image of the reverse side of the detection electronics board 802 that shows the detector 804. In the example of FIG. 8A and FIG. 8B, the detector is an avalanche photodiode (APD). In certain embodiments, other photodetectors, such as photodiodes (PDs), photomultiplier tubes (PMT), photoconductive detectors, are used. In certain embodiments, multi-element detectors, such as focal plane arrays (FPAs) (e.g. CCDs, CMOS detectors) are used.

The detector (e.g. an APD, PD, PMT) measures emitted light traveling through/along the optic fiber that is incident upon the active area of the detector. In response to light incident upon its active area, the detector (e.g. APD, PD, PMT) outputs an electrical signal (e.g. a current). The magnitude of the electrical signal output by the detector is a function of the power of the light incident on the active area of the detector, the wavelength of the incident light, and the responsivity (photo sensitivity) of the detector. Other factors, such as temperature, a gain setting of the detector (e.g. a gain setting can be controlled by virtue of a bias voltage applied across the detector) can also influence the magnitude of the electrical signal output by the detector.

Typically, the magnitude of the electrical signal produced by the detector is substantially proportional to the power of the light incident upon its active area. The responsivity (photo sensitivity) of the detector determines the magnitude of the electrical signal (e.g. a current) that the detector will produce per unit power incident upon its active area for light having a given wavelength.

Figure 8C:
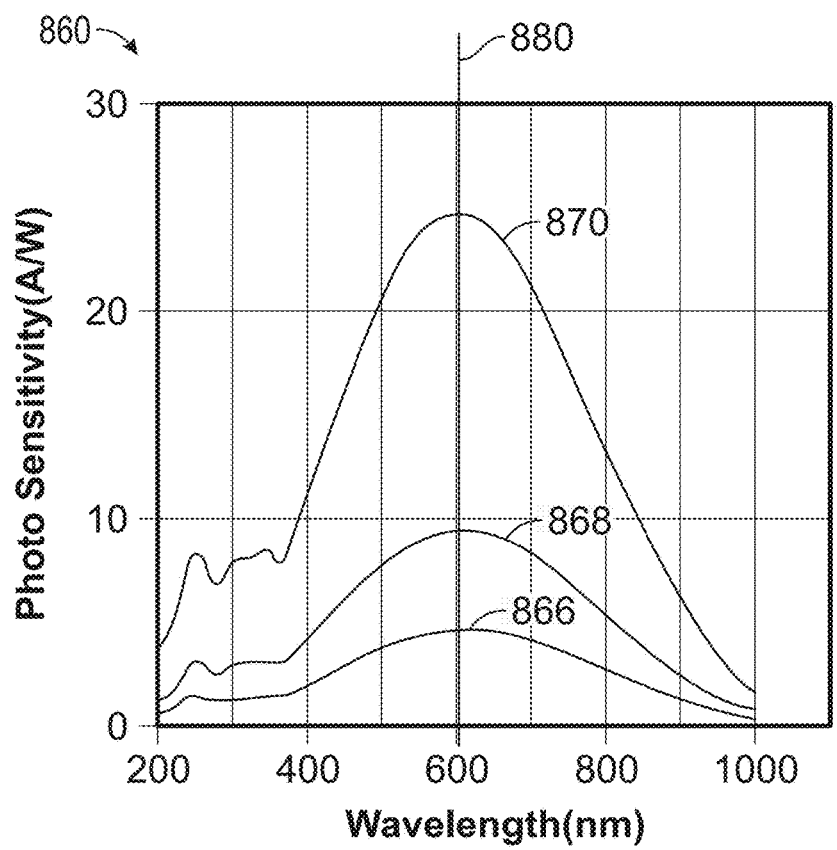
FIG. 8C is a graph showing an example set of responsivity curves for an avalanche photodiode (APD), according to an illustrative embodiment.

FIG. 8C shows an example of a graph 860 showing a set of responsivity curves for an APD. The different curves 866, 868, and 870 correspond to different gain settings of the APD. The curves 866, 868, and 870 show the current produced per unit power incident on the APD (e.g. measured in Amps per Watt). The peak responsivity (photo sensitivity) wavelength 880 of the APD occurs at approximately 620 nm. That is, light having a wavelength of approximately 620 nm will result in the larger electrical signal (e.g. current) per unit power than light having a different wavelength. Illuminating the detector (e.g. the APD) with light having a wavelength far from the peak responsivity wavelength will result in a negligible electrical signal produced by the detector (e.g. the APD).

In order to maximize the sensitivity of the detection system to light emitted from a given acceptor dye composition, an detector (e.g. an APD) having a peak responsivity wavelength that coincides with the emission wavelength of the acceptor dye composition may be selected. In the example of FIG. 8C, the peak sensitivity wavelength of 620 nm is near the emission wavelength of a Europium, which is 615 nm. Different detectors (e.g. different APDs) may be selected to optimize sensitivity to emission from different acceptor dye compositions.

The power supply supplies power to electronic components (e.g. the detector) of the detection system. In certain embodiments, the power supply is self-contained, and comprises a battery. In certain embodiments, the power supply board is used to control a bias voltage applied across the detector. In certain embodiments the bias voltage determines a gain setting of the detector, thereby facilitating detection of low intensities of incident light.

In certain embodiments, the system comprises additional electronics that receive a signal (e.g. a current) from the detector, and output a digitized signal that is representative of (e.g. substantially proportional to) a relative intensity of light incident on the detector.

Figure 8D:
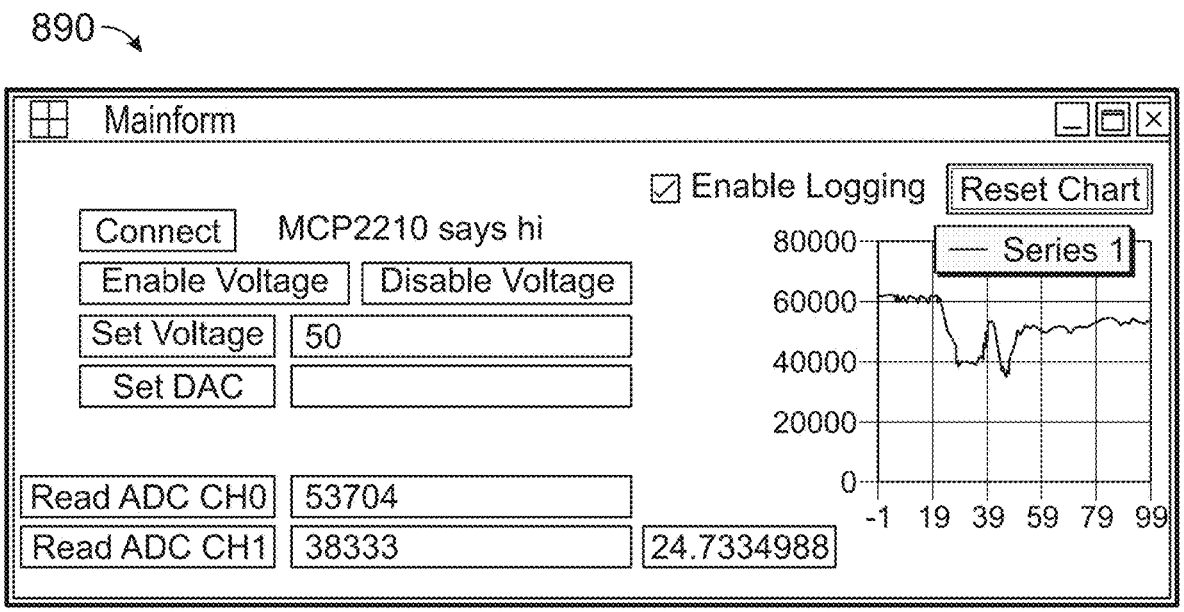
FIG. 8D is a screenshot of an example a graphical user interface of custom diagnostic software, according to an illustrative embodiment.

In certain embodiments, the system comprises custom diagnostic software. The diagnostic software receives a data corresponding to a signal from the detector that is representative of the detected emission light. In certain embodiments the data corresponding to a signal from the detector is a digitized signal that is representative of (e.g. substantially proportional to) a relative intensity of light incident on the detector (e.g. as produced by additional electronics of the system). Based on the received signal data, the custom diagnostic software provides for detection and/or quantification of one or more analytes based on the received signal. FIG. 8D is an example of a screenshot of a graphical user interface 890 of the custom diagnostic software.

Figure 9:
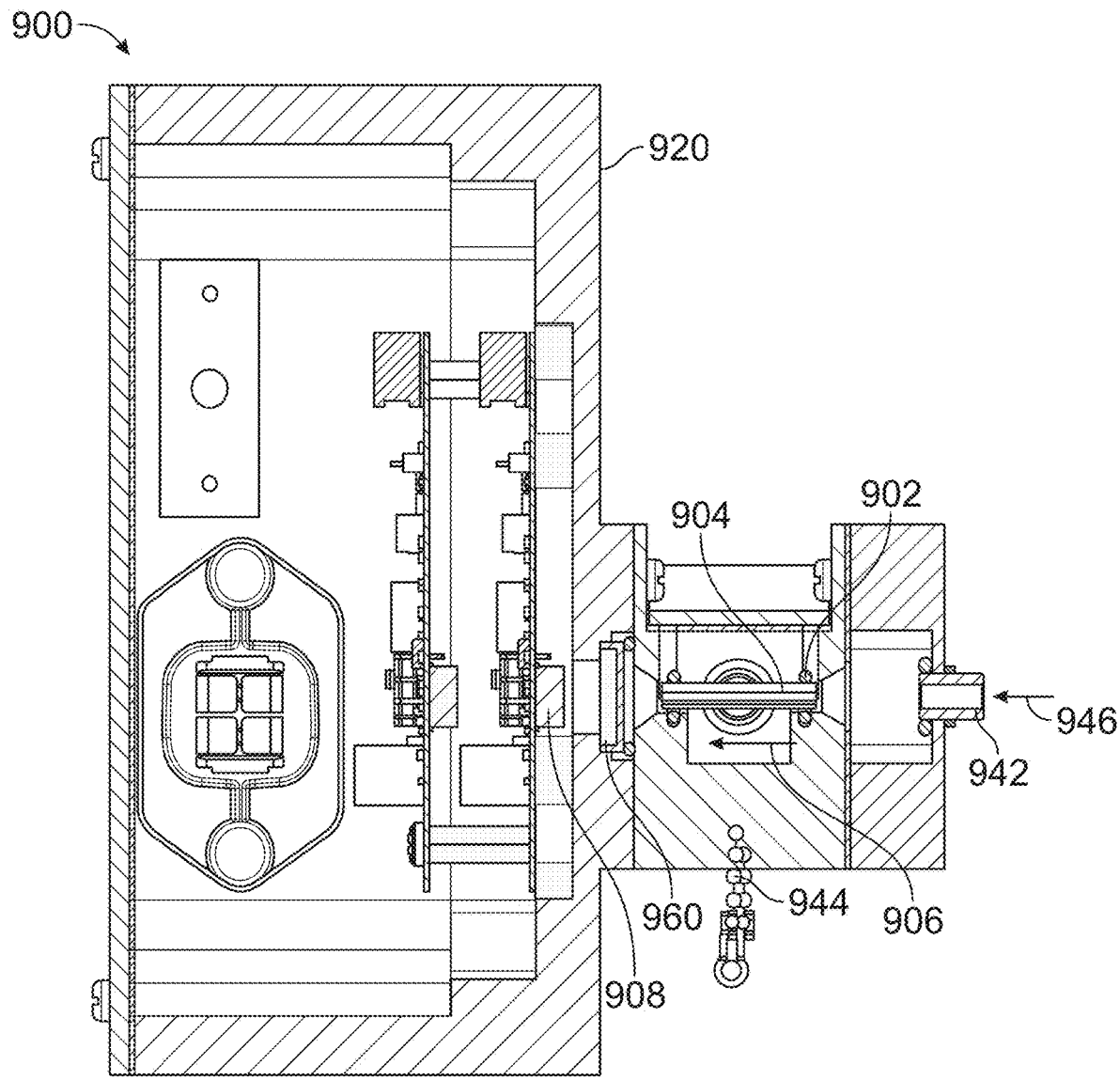
FIG. 9 is a schematic of an example system for single analyte and/or multiple analyte detection using the hollow polymer optic fibers described herein, according to an illustrative embodiment.
Figure 10:
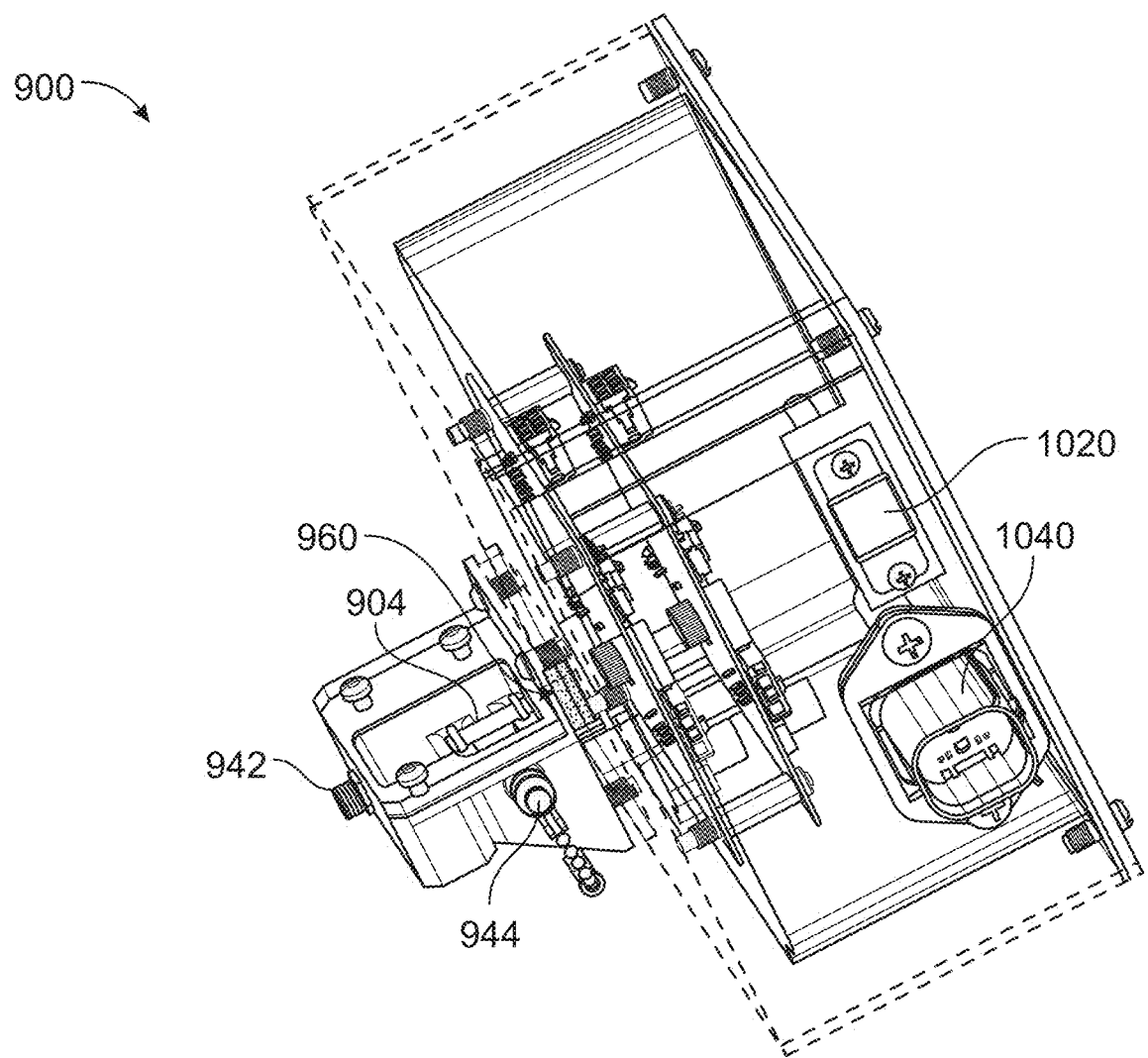
FIG. 10 is a schematic of an example system for single analyte and/or multiple analyte detection using the hollow polymer optic fibers described herein, according to an illustrative embodiment.

FIG. 9 and FIG. 10 are schematics of an example system 900 for single analyte and/or multiple analyte detection using the hollow core polymer optic fibers described herein. In certain embodiments, the system comprises a detector (e.g. an APD, a CCD, a PMT), and a power supply as described above with respect to FIG. 8A.

II.B Fiber Mount

In certain embodiments, the system comprises a fiber mount 902 for holding and aligning a polymer optic fiber and/or a bundle 904 of polymer optic fibers in-line with a detector. For example, when a fiber is placed in the fiber mount, the fiber mount holds the fiber such that the axis of the fiber is sufficiently straight and concentric with the detector (e.g. the axis of the fiber is aligned with the center of the active area of the detector). Similarly, a bundle of fibers 904 placed in the mount is held such that the fiber bundle axis is sufficiently straight and concentric with the detector (e.g. the axis of the fiber bundle is aligned with the center of the active area of the detector). In this manner, emission light 906 (e.g. from a fiber doped with an acceptor dye, e.g. from acceptor beads within a fiber) traveling along a fiber, exits the fiber at an end of the fiber, travels towards the detector, and is incident upon the active area of the detector. In certain embodiments, detecting emission light exiting the end of the fiber provides for the highest intensity of emission light incident on the detector, thereby maximizing the signal produced by the detector. As described above with respect to FIG. 1 and FIG. 2, the emission light may be produced by a fiber doped with an acceptor dye composition and/or acceptor beads within a fiber.

II.C Housing

In certain embodiments, the system comprises a housing 920 that surrounds the detector, fiber mount, and a fiber and/or fiber bundle placed in the mount. The housing 920 provides an enclosure that is substantially opaque to ambient light, thereby preventing ambient light from illuminating the detector 908 and/or fiber and/or fiber bundle 904.

II.D Excitation Ports

In certain embodiments the housing comprises one or more excitation ports through which excitation light from an excitation source can be directed (e.g. SMA ports to which a fiber coupled excitation source can connected). In certain embodiments, one of the excitation ports is an axial excitation port 942. The axial excitation port 942 is concentric with the detector 908 and the axis of a fiber and/or fiber bundle 904 placed in the fiber mount 902. When a fiber is placed in the fiber mount 902, excitation light 946 directed through the axial excitation port 942 travels along the fiber, in the direction of the detector 908, thereby illuminating the fiber. Similarly, when a fiber bundle 904 is placed in the fiber mount 902, excitation light 946 directed through the axial excitation port 942 travels along one or more fibers in the fiber bundle, in the direction of the detector 908.

In certain embodiments, one of the excitation ports is an orthogonal excitation port 944. The orthogonal excitation port 944 is aligned orthogonal to the axis of a fiber and/or fiber bundle 904 placed in the fiber mount 902. Excitation light directed through the orthogonal excitation port 944 travels towards a fiber and/or fiber bundle 904 placed in the fiber mount 902, in a direction orthogonal to the axis of the fiber and/or fiber bundle 904. Excitation light directed through the orthogonal excitation port 944 thus passes through a fiber placed in the fiber mount 902, thereby illuminating the fiber. Similarly, when a fiber bundle 904 is placed in the fiber mount 902, excitation light directed through the orthogonal excitation port 942 passes through one or more fibers of the fiber bundle 904, thereby illuminating one or more fibers of the fiber bundle.

In certain embodiments, the housing 920 comprises an axial excitation port. In certain embodiments the housing 920 comprises an orthogonal excitation port. In certain embodiments the housing 920 comprises two or more orthogonal excitation ports. In certain embodiments, the housing 920 comprises two orthogonal excitation ports and an axial excitation port.

In certain embodiments, the excitation ports are configured to connect to optical fibers (different from the hollow polymer optic fibers described herein) in order to accept excitation light from a fiber-coupled excitation source. For example, the excitation ports may be SMA ports. In certain embodiments, the excitation ports are sealed when not in use (e.g. via caps), in order to prevent ambient light from entering the housing 920.

In certain embodiments, the excitation source is external to the housing 920. For example, an external laser diode may be used as an excitation source. In certain embodiments, the housing 920 surrounds the excitation source as well as the detector, fiber mount, and a fiber and/or fiber bundle placed within the mount, such that the system is a self-contained system (e.g. a portable system, e.g. a handheld system).

II.E Optical Filters

In certain embodiments, the system comprises an optical filter 960 that is substantially opaque to light having a wavelength of the excitation light and transparent to light having a wavelength of an emission wavelength of an acceptor dye. The optical filter 960 is placed in front of the detector 908, thereby preventing excitation light (e.g. 946) from the excitation source from illuminating the detector, while allowing emission light 906 to pass and illuminate the detector 908. The transmittance of an optical filter corresponds to the fraction of light incident upon the optical filter that is transmitted through the optical filter, and is a function of the light's wavelength. Different optical filters having different transmittances are transparent and opaque to different wavelengths of light and may be used depending on the particular excitation sources that are used to illuminate a fiber and/or fiber bundle, as well as the different particular acceptor dye compositions with which either the fibers and/or acceptor beads are doped. The optical filters can be mounted in a switchable fashion, such that filters can be switched, e.g. in order to detect emission from a particular acceptor dye composition and/or block excitation light from a given excitation source.

II.E Miscellaneous Elements

In certain embodiments, the system comprises electronics components associated with the detector and power supply, and the housing enclosure 920 is sized to accommodate additional electronic components and wires.

In certain embodiments, the system comprises a power connector 1040 for connecting to an external power supply. In certain embodiments the system comprises an interface 1020 (e.g. a USB port) for connecting to an external computing device (e.g. a desktop computer). The various interfaces, ports, and power connectors are sealed with gaskets in order to prevent ambient light from entering the housing 920.

II.F Cartridge Reader

In certain embodiments, the system comprises a cartridge reader for sequentially reading signal from a plurality bundles of a cartridge of fiber bundles. The cartridge reader holds a particular bundle of a cartridge in an active position for illumination with excitation light and detection of emission light from the fibers of the bundle. The particular bundle in the active position is held such that the fiber bundle axis is sufficiently straight and concentric with the detector (e.g. the axis of the fiber bundle is aligned with the center of the active area of the detector). In this manner, emission light (e.g. from a fiber doped with an acceptor dye composition, e.g. from acceptor beads within a fiber) traveling along a fiber, exits the fiber at an end of the fiber, travels towards the detector, and is incident upon the active area of the detector.

The cartridge reader provides for mechanical switching between bundles held in an active position. In certain embodiments a first bundle in the cartridge is held in the active position, and is illuminated with excitation light. Emission light from the bundle is detected by the detector. Following detection of emission light from the first bundle, the cartridge reader switches the first bundle out of the active position, and switches a second bundle into the active position. The second bundle is then illuminated with excitation light, and emission light from the second bundle is detected by the detector.

II.G Modular Configuration

Figure 11:
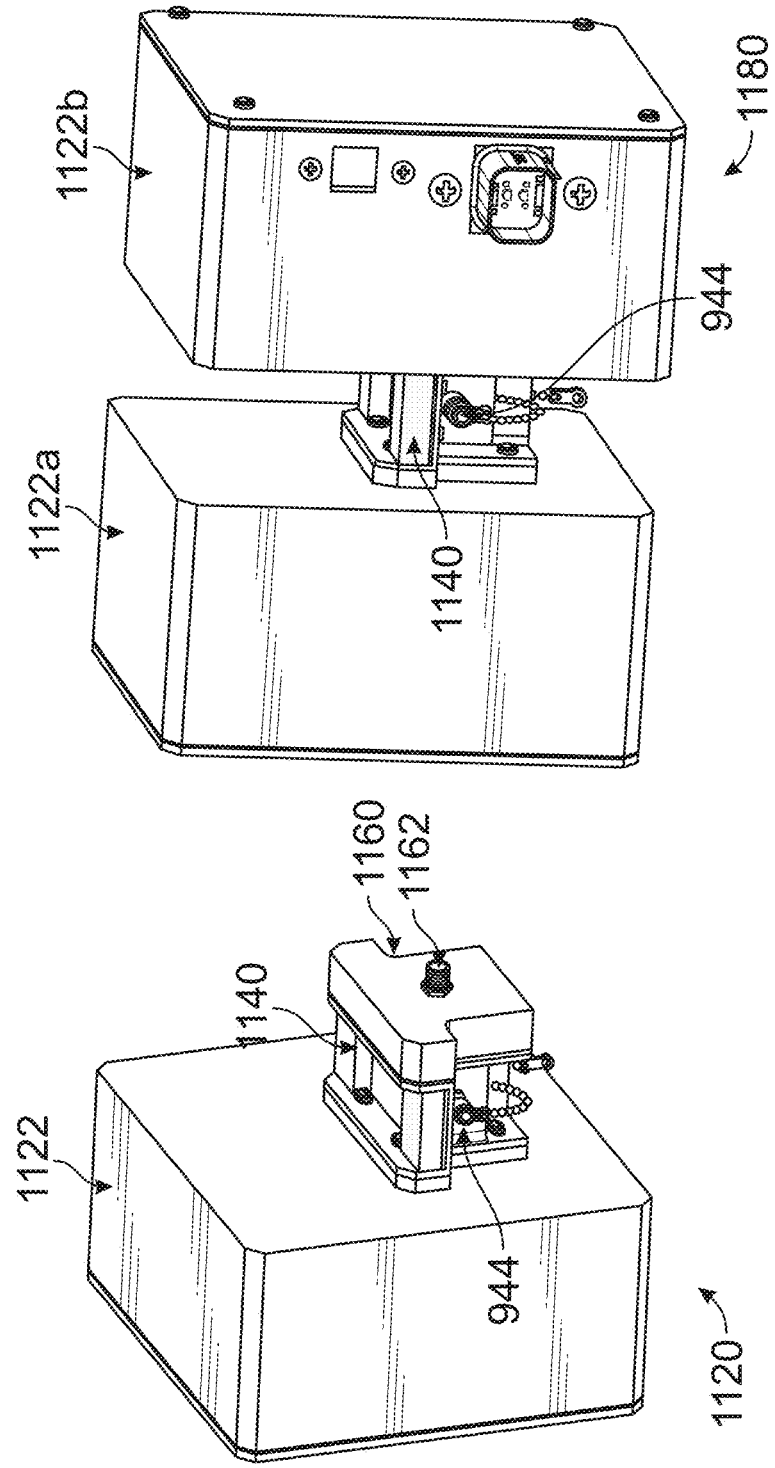
FIG. 11 is a schematic showing a system comprising a fiber enclosure module attached to a single detection unit module, and a system comprising a fiber enclosure module attached to two detection unit modules, according to an illustrative embodiment.

Turning to FIG. 11, in certain embodiments, the system comprises multiple modular units that are attached to each other and combined. In certain embodiments, the system comprises a fiber enclosure module 1140 and one or more detection unit modules 1122. The fiber enclosure module 1140 comprises the fiber mount 902 into which a fiber and/or fiber bundles are placed. The fiber enclosure module 1140 comprises a housing that surrounds the fiber mount and a fiber and/or fiber bundle placed therein. The fiber enclosure 1140 also comprises one or more excitation ports 942, 944. Each detection unit module 1122 comprises a detector, and associated electronics (e.g. a power supply, e.g. an interface board), as well as a housing that surrounds the detector and associated electronics. In certain embodiments each detection unit module 1122 comprises an optical filter.

The fiber enclosure module 1140 attaches to one or more detection unit modules 1122. The fiber enclosure module 1140 comprises a port that, when the fiber enclosure module is attached to a detection unit module 1122, aligns with a corresponding port of the detection unit module 1122 in order to allow emission light from a fiber within the fiber enclosure module 1140 to pass into the detection unit module and illuminate a detector of the detection unit module 1122.

In certain embodiments, the fiber enclosure module 1140 comprises two ports at opposite ends of the fiber enclosure module, such that two detection unit modules can be attached to a single fiber enclosure module.

FIG. 11 is a schematic showing a system comprising fiber enclosure module 1140 attached to a single detection unit module 1122 (1120), and a system comprising a fiber enclosure module 1140 attached to two detection unit modules 1122a and 1122b (1180). In certain embodiments, the fiber enclosure module 1140 comprising two ports is attached to a single detection unit module 1122, and an add-on module 1160 covers the unused port in order to prevent ambient light from entering the system via the fiber enclosure module. In certain embodiments the add-on module 1160 comprises an axial excitation port 1162.

In certain embodiments, the fiber enclosure module 1140 comprising two ports is attached to a first detection unit module 1122a and a second detection unit module 1122b, each comprising a detector and associated electronics. In certain embodiments a first detector of the first detection unit module 1122a is of the same type as a second detector of the second detection unit module 1122b (e.g. the responsivities of the first and second detectors have the same dependence the wavelength of light that illuminates the detectors). In certain embodiments a first detector of the first detection unit module 1122a is of a different type than a second detector of the second detection unit module 1122b (e.g. the first and second detectors have different responsivities that are different functions of the wavelength of light that illuminates the detectors). In certain embodiments the first detection unit module 1122a comprises a first optical filter and the second detection unit module 1122b comprises a second optical filter. In certain embodiments the first optical filter is of the same type as the second optical filter (e.g. the transmittances as a function of wavelength of incident light of the first and second optical filters are the same). In certain embodiments the first optical filter is of a different type from the second optical filter (e.g. the transmittances of the first and second optical filters are different functions of the wavelength of light).

II.H System Prototype

Figure 12A:
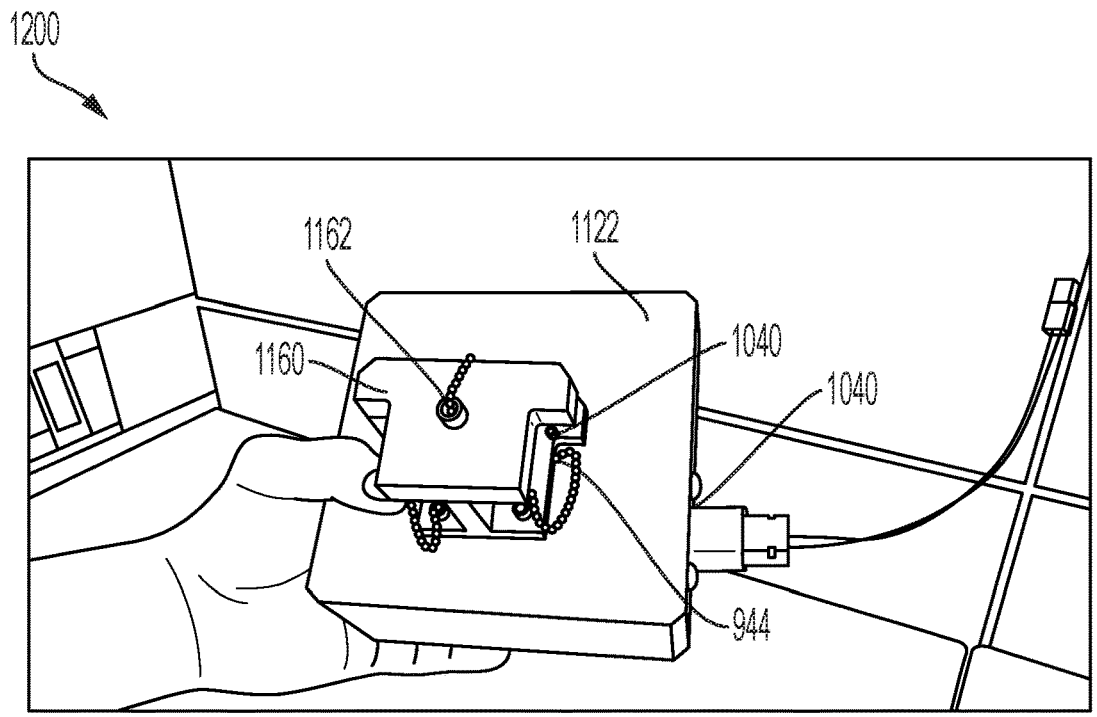
FIG. 12A is an image of an example system for detecting signal from a hollow polymer optic fiber for single and/or multiple analyte detection, according to an illustrative embodiment.
Figure 12B:
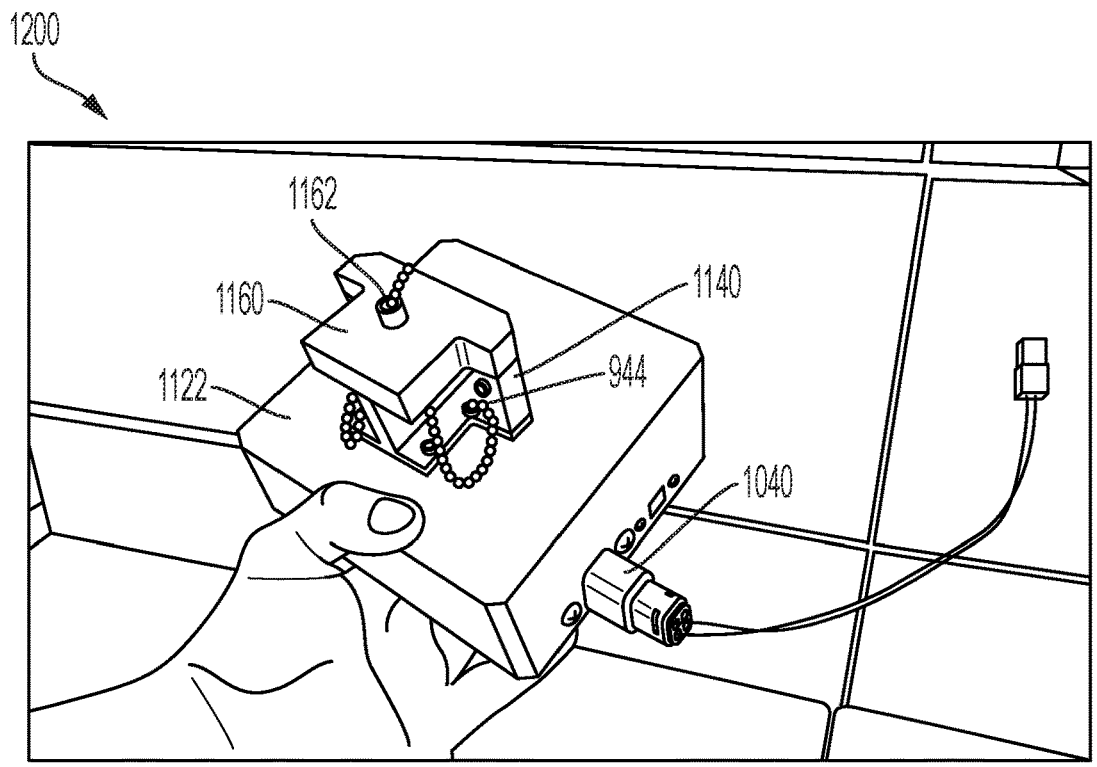
FIG. 12B is an image of an example system for detecting signal from a hollow polymer optic fiber for single and/or multiple analyte detection, according to an illustrative embodiment.

FIG. 12A and FIG. 12B are two images of an example system 1200 for detecting signal from a hollow core polymer optic fiber for single and/or multiple analyte detection. The images show the system 1200 comprising a fiber enclosure module 1140 connected to a single detection unit module 1122, and an add-on module 1162 covering the unused port of the fiber enclosure unit 1140. The system comprises an external power supply, and three excitation ports for connecting to external excitation sources.

In certain embodiments, the system is a self-contained system comprising a self-contained power supply (e.g. a battery) and one or more excitation sources (e.g. one or more laser diodes). In certain embodiments, all system components (e.g. power supply, detector, excitation source, fiber mount and a fiber and/or fiber bundle under test) are enclosed within a housing. In certain embodiments the system is a hand-held self-contained system. In certain embodiments the hand-held system weighs no greater than from 1 to 2 lbs. In certain embodiments the system occupies a total volume no greater than 750 cm$^3$. In certain embodiments the system is no greater than 150 mm long. In certain embodiments the system is no greater than 100 mm in width. In certain embodiments the system is no greater than 50 mm thick.

III Detection Modalities for Multiplexed Detection of Analytes

Several system configurations that provide for multiplexed detection and/or quantification of analytes are possible. Different approaches for multiplexing can be provided for by taking advantage of (i) the different emission wavelengths of different acceptor dye compositions; (ii) different excitation wavelengths of different donor dye compositions; and (iii) the different spatial positioning of different fibers within a bundle of fibers.

III.A Multiplexed Detection Using Different Acceptor Dye Emission Wavelengths

In certain embodiments, multiplexed detection of different analytes can be achieved by distinguishably detecting emission light from different acceptor dye compositions. A bundle of hollow polymer optic fibers doped with different acceptor dye compositions, and or acceptor beads doped with different acceptor dye compositions can be used. As described with respect to FIG. 3 above, the different fibers in the bundle can be doped with different acceptor dye compositions and the binding partners that are conjugated to the interior surfaces of the fibers may be varied from fiber to fiber.

Acceptor Dye Doped Fibers

In certain embodiments, multiplexed detection of different analytes can be achieved by distinguishably detecting emission light from different acceptor dye compositions and using a bundle of hollow polymer optic fibers 300 doped with acceptor dyes. As described with respect to FIG. 3 above, the different fibers in the bundle 300 can be doped with different acceptor dye compositions and the binding partners that are conjugated to the interior surfaces of the fibers may be varied from fiber to fiber.

In one example, a first fiber 302 of the bundle is doped with a first acceptor dye composition having a first emission wavelength, and a second fiber 304 of the bundle is doped with a second acceptor dye composition having a second emission wavelength that is distinct from the first emission wavelength. In particular, different acceptor dye compositions produce emitted light having different wavelengths. For example, the an acceptor dye composition comprising europium emits at a wavelength of 615 nm; an acceptor dye composition comprising dysprosium emits at a wavelength of 575 nm; an acceptor dye composition comprising samarium emits at a wavelength of 645 nm; and an acceptor dye composition comprising terbium emits at a wavelength of 545 nm. By selectively detecting light emitted at a particular wavelength, corresponding to the emission wavelength of a particular acceptor dye composition, the emitted light from a particular fiber doped with a particular acceptor dye composition can be identified. Accordingly, emitted light from different fibers doped with different acceptor dye compositions can be distinguished on the basis of the wavelength of the emitted light.

In order to detect the presence and/or concentrations of different analytes, different binding partners that undergo different molecular interactions with different analytes are also conjugated to the interiors of the different fibers. In particular, a first fiber binding partner conjugated to the interior surface of the first fiber 302, which is doped with the first acceptor dye composition, binds to a first analyte. As described with respect to FIG. 1 above, a sandwich assay is created when a first particle binding partner, which is coupled to donor beads, also binds to the first analyte. As a result, the donor beads are brought in proximity to the interior surface of the first fiber by virtue of the sandwich assay created by the interaction between the first fiber binding partner, first analyte, and first particle binding partner. Upon illumination by excitation light, the proximity of the donor beads to the first acceptor dye composition with which the first fiber 302 is doped results in the emission of light at the first emission wavelength. Detecting emission light at the first emission wavelength thereby allows detection of the presence and/or concentration of the first analyte.

Similarly, a second fiber binding partner that binds to a second analyte can be conjugated to the interior of the second fiber 304, which is doped with the second acceptor dye composition. Donor beads coupled to a second particle binding partner, which also binds to the second analyte are brought into proximity with the interior surface of the second fiber 304 via the interaction between the second fiber binding partner, second analyte and second particle binding partner. Illumination by excitation light thus results the emission of light, at the second emission wavelength, which is indicative of the presence and/or concentration of the second analyte.

By distinguishably detecting emission light at the first and second emission wavelengths, the first and second analytes can thus be detected. This approach can be extended to provide for detection of a plurality of different analytes, where each analyte is captured by a corresponding fiber binding partner conjugated to the interior surface of a corresponding fiber in a bundle of fibers. Each corresponding fiber is doped with a distinct acceptor dye composition that emits light at a distinct emission wavelength. Distinguishably detecting light at the distinct emission wavelengths, each indicative of the presence and/or concentration of a different analyte, thereby provides for multiplexed detection of the presence and/or concentration of a plurality of different analytes.

Donor Dye Doped Fibers

In certain embodiments, different types of acceptor beads doped with different acceptor dye compositions are used in combination with fibers doped with donor dye compositions for multiplexed detection. This approach is similar to the previously described approach in which different fibers in a bundle of fibers can each be doped with different acceptor dye compositions in order to provide for multiplexed detection of multiple distinct analytes, In particular, in certain embodiments, a first type of acceptor bead doped with a first acceptor dye composition (having a first emission wavelength) has a first particle binding partner conjugated to its surface, and a second type of acceptor bead doped with a second acceptor dye composition (having a second emission wavelength that is distinct from the first emission wavelength) has a second particle binding partner conjugated to its surface. The first particle binding partner binds to a first analyte, and the second particle binding partner binds to a second analyte. As described above with respect to FIG. 2, when the acceptor beads are brought into proximity to 'donor' optic fibers doped with donor dye compositions via a molecular interaction of interest (e.g. antigen-IgG interaction), emitted light (e.g. fluorescence, e.g. lanthanide fluorescence) is produced by the acceptor nanoparticles via excitation of the donor optic fiber by excitation light.

In particular, a donor optic fiber is coated with a first fiber binding partner that captures the first analyte. When the first particle binding partner, which is coupled to the first type of acceptor bead, also binds to the first analyte, the acceptor beads of the first type are thus brought into proximity to the donor fiber by virtue of the presence of the first analyte. Accordingly, excitation of the donor fiber results in the emission of light, having the first emission wavelength, by the acceptor beads of the first type. Similarly, a donor optic fiber coated with a second fiber binding partner that captures the second analyte results in the creation of a sandwich assay when the second particle binding partner, which is coupled to acceptor beads of the second type, also binds to the second analyte. Excitation of the donor fiber results in the emission of light having the second emission wavelength by the second acceptor dye composition with which the type of second acceptors bead are doped. Thus, as with the previously discussed acceptor dye doped fibers, light emission at the first emission wavelength is indicative of the presence and/or concentration of the first analyte, and light emission at the second emission wavelength is indicative of the presence and/or concentration of the second analyte. By distinguishably detecting emission light at the first and second emission wavelengths, the presence and/or concentrations of first and second analytes can thus be detected.

Similar to the acceptor doped fibers, this approach can be extended to provide for detection of a plurality of different analytes. In the case of acceptor beads and donor fibers, each analyte binds to a corresponding particle binding partner conjugated to the surfaces of a corresponding type of acceptor bead. Each corresponding type of acceptor bead is doped with a distinct acceptor dye composition that emits light at a distinct emission wavelength. Distinguishably detecting light at a plurality of distinct emission wavelengths, each indicative of the presence and/or concentration of a different analyte, thereby provides for multiplexed detection of the presence and/or concentration of a plurality of different analytes.

In certain embodiments, a single donor fiber has multiple different fiber binding partners conjugated to its interior surface, each of which captures a different analyte. Different types of acceptor beads, each of which is doped with a distinct acceptor dye composition having a distinct emission wavelength, are coated with a different particle binding partners, each of which binds to a different analyte. In certain embodiments, a bundle of donor fibers 400 is used, with each donor fiber having a different fiber binding partner, that captures a different analyte, conjugated to its interior surface.

System Components

In certain embodiments, differentiating between the first and second emission wavelengths can be accomplished through the use of multiple detectors and/or optical filters. For example, as described above, the presence and/or concentration of a first and second analyte can be determined by distinguishably detecting emission light having a first and second wavelength, respectively. Accordingly, a first detector having a peak responsivity near a first emission wavelength can be used to selectively detect emission light at the first emission wavelength, and, accordingly, the presence of a first analyte. A second detector having a peak responsivity near a second emission wavelength can be used to selectively detect emission light at the second emission wavelength, and, accordingly, the presence of a second analyte.

Similarly, a detector that is sensitive to light at both the first and second emission wavelengths can be used in combination with two optical filters. In particular, a first optical filter that is transparent to the first emission wavelength and opaque to the second emission wavelength can be placed in front of the detector in order to selectively pass light having the first emission wavelength. Similarly, a second optical filter that is transparent to the second emission wavelength and opaque to the first emission wavelength placed in front of the detector will selectively pass light having the second emission wavelength. Accordingly, signal produced by the detector with the first filter in place will be indicative of the presence and/or concentration of the first analyte, while signal produced by the detector with the second filter in place will be indicative of the presence and/or concentration of the second analyte.

Multiple detectors can be used in combination with multiple filters in order to optimally distinguish between light of the first and second emission wavelengths, as well as improve convenience and/or measurement speed (e.g. by avoiding the need to switch between different filters and/or detectors).

For example, in certain embodiments the system comprises a first and second detector of the same type (e.g. having the same responsivities to light of different wavelengths), but with different optical filters placed in front of them. A first optical filter placed in front of the first detector is transparent to light having the first emission wavelength, and opaque to light having the second emission wavelength. A second optical filter placed in front of the second detector is transparent to light having the second emission wavelength, and opaque to light having the first emission wavelength. The first and second detectors can thus be used to distinguishably detect light of the first and second emission wavelengths in parallel (e.g. at the same time).

In certain embodiments, a plurality of distinct emission wavelengths from corresponding acceptor dye compositions can be distinguishably detected via multiple detectors and/or optical filters. In certain embodiments, a corresponding detector is used to detect light at each emission wavelength. In certain embodiments, each corresponding detector is of a different type. In certain embodiments, each corresponding detector is of the same type, but has a distinct corresponding optical filter placed in front of it. In certain embodiments, the system comprises a single detector and a plurality of optical filters, wherein each filter corresponds to a respective emission wavelength and is transparent to that emission wavelength and opaque to light of the other emission wavelengths.

In certain embodiments, a single detector with a plurality of pixels is used, and a dispersive optical element (e.g. a prism, e.g. a grating) is placed in front of the detector. The dispersive optical element refracts light at different angles depending on the wavelength of the light, and thereby causes light of different wavelengths to be incident on different positions of the detector. Accordingly, through the use of a dispersive optical element, light of each emission wavelength illuminates a different corresponding set of pixels of the detector, and the signal from each corresponding set of pixels is indicative of the presence and/or concentration of a different analyte.

III.B Multiplexed Detection Using Different Donor Dye Excitation Wavelengths

In certain embodiments, multiplexed detection of the presence and/or concentration of analytes can also be achieved through the use of different donor dyes. Different donor dye compositions having distinct excitation wavelengths can be selectively excited by illumination with light having different corresponding wavelengths, thereby providing for multiplexed detection of the presence and/or concentration of different analytes.

Donor Dye Doped Fibers

In particular, in certain embodiments, different fibers in a bundle of fibers are doped with different donor dye compositions having distinct excitation wavelengths. In one example, a first fiber 402 in the bundle 400 is doped with a first donor dye composition having a first excitation wavelength, and a second fiber 404 in the bundle 400 is doped with a second donor dye composition having a second excitation wavelength that is distinct from the first excitation wavelength. Illumination of the fiber bundle with excitation light having the first excitation wavelength excites the first donor dye composition with which the first fiber 402 is doped, but not the second donor dye composition with which the second fiber 404 is doped. Accordingly, upon illumination with excitation light having the first excitation wavelength, emission light will be produced by acceptor beads within the first fiber 402, but not the second fiber 404. Similarly, illumination of the fiber bundle at the second excitation wavelength excites the second donor dye with which the second fiber 404 is doped, but not the first donor dye with which the first fiber 402 is doped. Accordingly, upon illumination with excitation light having the second excitation wavelength, emission light will be produced by acceptor beads within the second fiber 404, but not the first fiber 402.

The interior surface of the first fiber 404 is conjugated with a first fiber binding partner that captures a first analyte, and the interior surface of the second fiber 402 is conjugated with a second fiber binding partner that captures a second analyte. Acceptor beads coated with a first particle binding partner that binds to the first analyte. Thus, in the presence of the first analyte, acceptor beads coated with the first particle binding partner are brought into proximity to the interior surface of the first fiber 402 by virtue of the interaction between the first fiber binding partner, first analyte, and first particle binding partner. Similarly in the presence of a second analyte, acceptor beads coated with a second particle binding partner, that binds to the second analyte, are brought into proximity to the interior surface of the second fiber 404 by virtue of the interaction between the second fiber binding partner, second analyte, and second particle binding partner.

Accordingly, emission light produced by acceptor beads within the first fiber 402, in response to excitation light having the first excitation wavelength is indicative of the presence and/or concentration of the first analyte. Emission light produced by acceptor beads within the second fiber 404, in response to excitation light having the second excitation wavelength is indicative of the presence and/or concentration of the second analyte.

Acceptor Dye Doped Fibers

In certain embodiments, different donor beads, doped with different donor dye compositions having different excitation wavelengths, are used to provide for multiplexed detection of analytes. In particular, donor beads of a first type, doped with a first donor dye composition having a first excitation wavelength, have a first particle binding partner conjugated to their surface. Donor beads of a second type, doped with a second donor dye composition (having a second excitation wavelength that is distinct from the first excitation wavelength), have a second particle binding partner conjugated to their surface. The first particle binding partner binds to a first analyte, and the second particle binding partner binds to a second analyte.

An acceptor dye doped fiber having a first fiber binding partner conjugated to its interior surface captures the first analyte, and thereby brings the donor beads of the first type into proximity with the interior surface of the fiber. Similarly, an acceptor dye doped fiber having a second fiber binding partner conjugated to its interior surface captures the second analyte, and thereby brings the donor beads of the second type into proximity with the interior surface of the fiber.

In certain embodiments, a first fiber in a bundle of fibers has the first fiber binding partner conjugated to its interior surface and a second fiber in the bundle of fibers has the second fiber binding partner conjugated to its interior surface. The first fiber in the bundle thus captures the first analyte, thereby causing the donor beads of the first type to be in proximity with its interior surface, and the second fiber in the bundle thus captures the second analyte, thereby causing the donor beads of the second type to be in proximity with its interior surface.

Illumination of the bundle with excitation light having the first excitation wavelength excites of the first donor dye composition with which the first type of donor beads are doped, thereby causing emission from the acceptor dye doped first fiber. The second donor dye composition with which the second type of donor beads are doped is not excited by excitation light having the first excitation wavelength, and, thus, emission light is not produced from the second fiber in response to illumination with excitation light having the first excitation wavelength. Emission light detected from the first fiber, in response to illumination with excitation light having the first excitation wavelength is thus indicative of the presence and/or concentration of the first analyte. Analogously, illumination of the bundle with excitation light having the second excitation wavelength excites of the second donor dye composition with which the second type of donor beads are doped, thereby causing emission from the acceptor dye doped second fiber. The first donor dye composition with which the first type of donor beads are doped is not excited by excitation light having the second excitation wavelength, and, thus, emission light is not produced from the first fiber in response to illumination with excitation light having the second excitation wavelength. Emission light detected from the second fiber, in response to illumination with excitation light having the second excitation wavelength is thus indicative of the presence and/or concentration of the second analyte.

In certain embodiments, the same fiber has both the first and second fiber binding partner conjugated to its interior surface, and both the first and second donor beads may be present within the fiber. Illumination of the fiber with excitation light having the first excitation wavelength excites of the first donor dye composition with which the first donor beads are doped, but not the second donor dye composition with which the second donor beads are doped. Illumination of the fiber with excitation light having the second excitation wavelength excites of the second donor dye composition with which the second donor beads are doped, but not the first donor dye composition with which the first donor beads are doped. Accordingly, emission light detected in response to illumination with the first excitation wavelength is indicative of the presence and/or concentration of the first analyte, and emission light detected in response to illumination with the second excitation wavelength is indicative of the presence and/or concentration of the second analyte.

System Components

In certain embodiments, in order to provide excitation light having different excitation wavelengths corresponding to different donor dye compositions, the system comprises two or more different excitation sources (e.g. different laser diodes, e.g. different LEDs) each of which produces light having a different wavelength. In certain embodiments, each different excitation source is directed through a different excitation port of the system.

In certain embodiments a single excitation source is used to provide excitation light at different excitation wavelengths. In certain embodiments the single excitation source is a tunable laser. In certain embodiments the single excitation source is a broadband source that produces light at a range of wavelengths, and optical filters are used to selectively transmit light at particular wavelengths corresponding to the excitation wavelengths of different donor dye compositions.

III.C Multiplexed Detection Using Spatial Positioning

Detection of Emission from Different Fibers of a Bundle

In certain embodiments, multiplexed detection of multiple analytes can also be achieved by mapping light emission from each fiber in a bundle of fibers to a different set of one or more pixels of a focal plane array (e.g. a CCD, e.g. a CMOS camera) based on the different spatial locations of the fibers in the bundle. Light emission from each fiber in the bundle is thus distinguishably detected by a corresponding set of one or more pixels of the focal plane array.

Different fibers in the bundle can have different fiber binding partners that bind to different analytes conjugated to their interior surfaces. Light emission from the different fibers in the bundle is thus indicative of the presence and/or concentration of different analytes. Light detected by a first set of one or more pixels corresponding to a first fiber (e.g. the first set of pixels distinguishably detects light from the first fiber) is thus indicative of the presence and/or concentration of a first analyte that a first fiber binding partner, conjugated to the interior surface of the first fiber, captures. Light detected by a second set of one or more pixels corresponding to a second fiber (e.g. the second set of pixels distinguishably detects light from the second fiber) is thus indicative of the presence and/or concentration of a second analyte that a second fiber binding partner, conjugated to the interior surface of the second fiber, captures.

Detection of Emission from Different Sections of a Fiber

In certain embodiments, a fiber comprising multiple (e.g. discrete) different portions along its length, such as any of the fibers described above with respect to FIG. 5, is used for multiplexed detection. Multiple detectors can be aligned along the length of the fiber to distinguishably detect emission light from each different portion of the fiber.

III.D Combined Multiplexed Detection

In certain embodiments, multiplexing approaches based on (i) the different emission wavelengths of different acceptor dye compositions; (ii) different excitation wavelengths of different donor dye compositions; and (iii) the different spatial positioning of different fibers within a bundle of fibers, are combined.

For example, combinations of different acceptor dye compositions and donor dye compositions can be used to provide for multiplexed detection of a plurality of analytes. In particular, in certain embodiments, multiple (e.g. two) fibers in a bundle of fibers are doped with the same acceptor dye composition, but used to detect the presence and/or concentration of different analytes by virtue of each fiber having a different fiber binding partner conjugated to its interior surface. While the fibers doped with the same acceptor dye composition will produce emission light having the same emission wavelength, different donor beads, doped with different donor dye compositions can be used to distinguish between the different fibers, and, accordingly, different analytes, on the basis of the different excitation wavelengths of the different donor dye compositions.

In particular, in certain embodiments, a first fiber and second fiber in a bundle of fibers are doped with an common acceptor dye composition that is different from the acceptor dye compositions with which all the other fibers in the bundle are doped. The first fiber has a first fiber binding partner, which captures a first analyte, conjugated to its interior surface, and the second fiber has a second fiber binding partner, which captures a second analyte, conjugated to its interior surface. Donor beads of a first type are doped with a first donor dye composition, having a first excitation wavelength, and coated with a first particle binding partner that binds to the first analyte. Donor beads of a second type are doped with a second donor dye composition, having a second excitation wavelength, and coated with a second particle binding partner that binds to the second analyte. Accordingly, in the presence of the first analyte, donor beads of the first type are brought into proximity with the interior surface of the first fiber, and in the presence of the second analyte, donor beads of the second type are brought into proximity with the interior surface of the second fiber.

Illumination with excitation light having the first excitation wavelength excites the donor beads of the first type, and results in the emission of light, from the first fiber, that is indicative of the presence and/or concentration of the first analyte. Illumination with excitation light having the second excitation wavelength excites the donor beads of the second type, and results in the emission of light, from the second fiber, that is indicative of the presence and/or concentration of the second analyte. Thus, emission from the first and second fibers is distinguishable on the basis of the excitation wavelength that it is produced in response to. Since the first and second fibers are doped with an acceptor dye composition that is different from the acceptor dye composition(s) with which the other fibers in the bundle are doped, emission from the first and second fibers can be distinguished from emission from the other fibers in the bundle via its wavelength, as described above.

In this manner, in certain embodiments, a combination N acceptor dye compositions, having N distinct emission wavelengths, and M donor dye compositions having M distinct excitation wavelengths can be used to detect N×M analytes via a bundle of fibers comprising N×M fibers. In certain embodiments, the same approach can be applied, but with donor dye doped fibers and acceptor dye doped beads.

IV. Sampling Method

In certain embodiments, in order to detect the presence and/or concentration of analytes in a sample a fiber and/or fiber bundle is contacted with (e.g., dipped into) a sample solution comprising the sample to be detected and a detection mixture. The detection mixture is a solution comprising donor beads and/or acceptor beads. In certain embodiments, the detection mixture comprises one or more types of donor beads and or acceptor beads. Each donor bead type and/or acceptor bead type has a corresponding particle binding partner conjugated to its surface that binds with a particular corresponding analyte of interest. If a particular analyte of interest is present in the sample, the beads (e.g. acceptor beads, e.g. donor beads) of the corresponding type bind to the particular analyte via the corresponding particle binding partner. When a fiber (e.g. a single fiber or a fiber of a bundle of fibers that is dipped into the sample solution) is dipped into the sample solution, the beads bound to the analytes of interest are drawn into the interior of the fiber (e.g. by capillary forces). If the fiber has a corresponding fiber binding partner that binds to the analyte of interest conjugated to its interior surface, the beads bound to the analyte of interest are brought into proximity with the interior surface of the fiber.

If the beads are donor beads, doped with a donor dye composition, and the fiber is doped with an acceptor dye composition, upon illumination with excitation light, the donor dye composition with which the donor beads are doped is excited, and emission light is emitted from the acceptor dye composition with which the fiber is doped. If the beads are acceptor beads, doped with a acceptor dye composition and the fiber is doped with an donor dye composition, upon illumination with excitation light, the donor dye composition with which the fiber is doped is excited, and emission light is emitted from the acceptor dye composition with which the beads are doped.

In certain embodiments the sample is a liquid sample that is mixed with the detection mixture. In certain embodiments, the sample is a solid sample that is crushed and/or dissolved in a solution, and the solution comprising the crushed and/or dissolved sample is mixed with the detection mixture.

Figure 14:
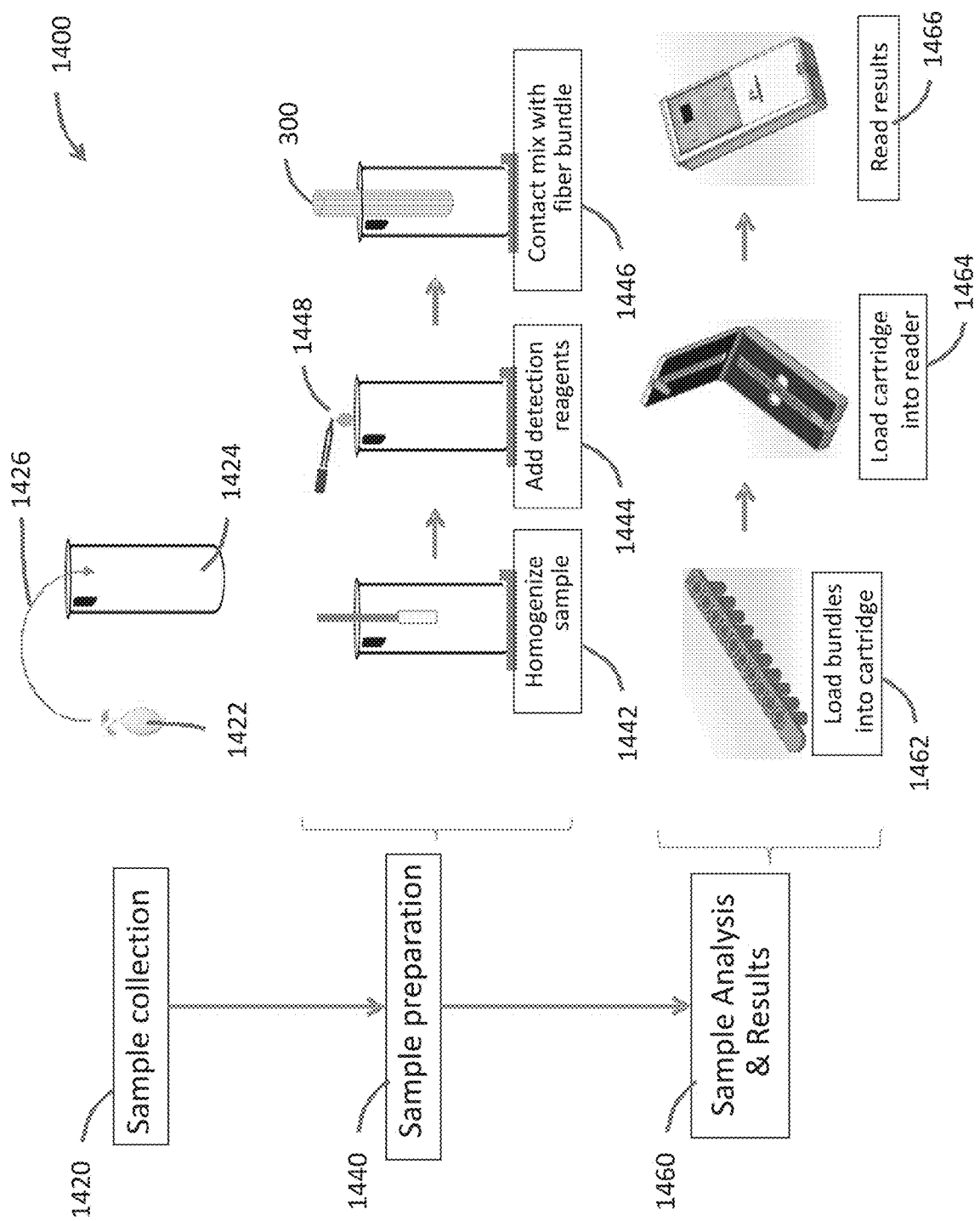
FIG. 14 is a diagram of a process for obtaining and analyzing a sample via the hollow polymer optic fiber system, according to an illustrative embodiment.

FIG. 14 is a diagram depicting an example process 1400 for collecting a sample 1420, preparing and introducing a sample solution into a bundle of polymer optic fibers, and reading signal from the polymer optic fibers for detection and/or quantification of one or more analytes of interest. In certain embodiments, at the sample collection step 1420, the sample 1422 is introduced (1426) into a reaction vessel 1424 (e.g. a test tube). At the sample preparation step 1440, the sample is homogenized 1442. For example, a solid sample (e.g. a seed) is crushed and mixed in a solution. In another step, a detection mixture 1448 comprising acceptor and/or donor beads is added to the solution (1444), such that the sample solution comprises the sample to be analyzed and the detection mixture. In another step, the sample solution is contacted 1446 with a bundle of polymer optic fibers (e.g. a bundle of polymer optic fibers doped with acceptor dye compositions 300, e.g. a bundle of polymer optic fibers doped with donor dye compositions 400) in order to introduce the sample solution into the interior of the polymer optic fibers of the bundle (e.g. via capillary action). In certain embodiments, the sample solution is, similarly, contacted with a single polymer optic fiber in order to introduce the sample solution into the interior of the polymer optic fiber.

Finally, in a sample analysis step 1460, a bundle of polymer optic fibers is illuminated with excitation light, and the resulting emission is detected in order to detect the presence of and/or quantify one or more analytes of interest. As described herein, for example in Section III, multiplexing approaches that take advantage of (i) the different emission wavelengths of different acceptor dye compositions; (ii) different excitation wavelengths of different donor dye compositions; and (iii) the different spatial positioning of different fibers within a bundle of fibers can be used for detection and/or quantification of multiple analytes of interest.

In the example of FIG. 14, the bundle is loaded into a cartridge 1462 comprising a plurality of bundles. The cartridge 1462 is loaded (1464) into a reader 1462 for detecting signal form one or more bundles of the cartridge. Each bundle can be read 1466 by illuminating the bundle with excitation light and detecting resultant emission light via the systems and methods described herein. In certain embodiments, each of a plurality of bundles of the cartridge is contacted with the sample solution, and used for detection and/or quantification of a different corresponding analytes of interest. In certain embodiments, each of a plurality of the bundles of the cartridge is contacted with a different sample solution, comprising a different sample, thereby providing for multiplexed detection of multiple analytes form multiple samples.

V. Examples

Example 1—Preparation of Europium Chelate Eu(NTA)$_3$BINAPO

Example 1 is an example of a process for preparing a fluorescent compound used in an acceptor dye composition. In the example, the compound is a europium chelate, specifically Eu(NTA)$_3$BINAPO. Other types of europium chelates can also be used as acceptor dyes. In the example process, NTA (4,4,4,-trifluoro-1-(2-naphthyl)-1,3-butadione), (800 mg, 3.0 mmol) and Europium (III)chloride hexahydrate (366 mg, 1.0 mmol) were dissolved together in 10 mL of absolute ethanol along with triethylamine (700 μL, 5 mmol) in a 50 mL round bottom flask to produce a europium-NTA solution. The europium-NTA solution was warmed to 75° C. in an oil bath while stirring for five minutes. BINAPO ([1,1'-binaphthalene]-2,2'-diylbis(diphenylphosphine oxide), (655 mg, 1.0 mmol) was dissolved in 10 mL of absolute ethanol by heating to 75° C. The heated BINAPO-in-ethanol solution was then added, prior to cooling (e.g. while still at a temperature substantially close to 75° C.) to the europium-NTA solution. The combined solution, comprising the europium, NTA, and BINAPO, refluxed for 1 hour then allowed to cool to room temperature. The resulting precipitate was collected on a paper filter (Whatman 3), washed with ethanol, and dried under vacuum to yield 1.28 g (80%) of an a powder (off-white in color) comprising $Eu(NTA)_3BINAPO$.

Example 2—Preparation of $Eu(NTA)_3BINAPO/C28$ Thioxene Solution for Dyeing of Hollow Polymer Optical Fibers Example 2 is an example of a process for preparing a solution of acceptor dye comprising a chemiluminescent singlet oxygen acceptor and a fluorescent compound. The acceptor dye solution is used for doping a hollow core polymer optic fiber with an acceptor dye composition (e.g. an acceptor dye composition comprising a chemiluminescent singlet oxygen acceptor and a fluorescent compound). In the example, the acceptor dye solution comprises a europium chelate, $Eu(NTA)_3BINAPO$, and C28 thioxene. The C28 thioxene is a chemiluminescent singlet oxygen acceptor and the europium chelate is a fluorescent compound. In the example, $Eu(NTA)_3BINAPO$ (160 mg, 0.10 mmol) was dissolved in 3.2 mL of 2-ethoxyethanol to a final concentration of 50 mg/mL with the aid of heating to 70° C. Separately, C28 thioxene (4-(2-phenyl-5,6-dihydro-1,4-oxathiin-3-yl)-N,N-ditetradecylaniline), (80 mg, 0.12 mmol) was dissolved in 3.2 mL of 2-ethoxyethanol to a final concentration of 25 mg/mL with the aid of heating to 70° C. The two solutions were combined, allowed to cool to room temperature (20° C.), then filtered through a 0.7μ glass microfiber syringe filter (Whatman). The final, filtered, solution was stored in the dark and used (e.g. for doping of a polymer optic fiber) within twenty four hours.

Figure 15A:
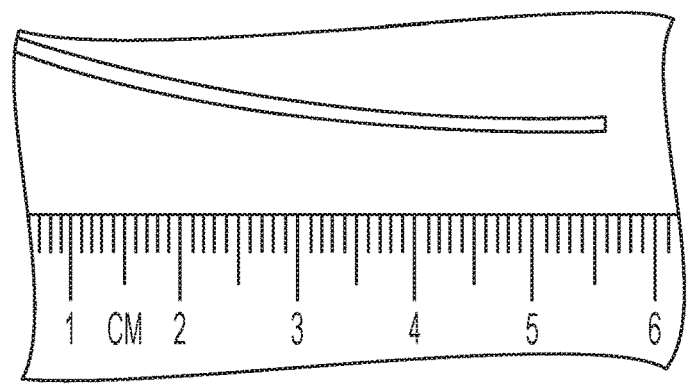
FIG. 15A is an image of a polymer optic fiber comprising multiple hollow cores, according to an illustrative embodiment.
Figure 15B:
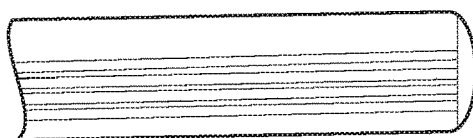
FIG. 15B is an image of a polymer optic fiber comprising multiple hollow cores, according to an illustrative embodiment.
Figure 15C:
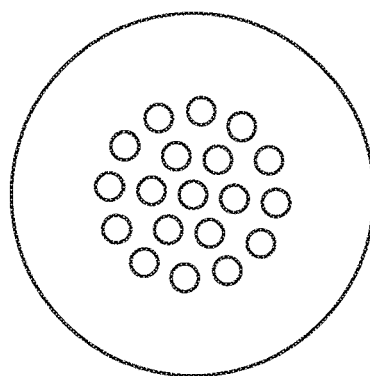
FIG. 15C is an image of an end facet of a polymer optic fiber comprising multiple hollow cores, according to an illustrative embodiment.

Example 3—Multi-Hole Hollow Polymer Optical Fiber for Increasing Binding Surface Area Example 3 is an example of a multi-core hollow polymer optical fiber, comprising multiple hollow cores (e.g. hollow channels within the fiber). The multi-core hollow polymer optical fiber provides for increased available surface area for analyte binding, and as well as decreased distance that an analyte or assay reagent needs to diffuse in order to reach the surface of the hollow polymer optical fiber. FIG. 15 is an image of a multi-core hollow polymer optical fiber. FIG. 15B is another image of the multi-core hollow polymer optic fiber. FIG. 15C is an image of an end facet of the multi-core hollow polymer optic fiber showing the multiple hollow cores of the fiber.

The multi-core hollow polymer optical fiber in this example is made of polystyrene, has an outer diameter of 1.3 mm and comprises 19 hollow channels of inner diameter of 105 μm, each of which was dyed with acceptor dye composition (e.g. comprising a chemiluminescent compound, e.g. comprising a chemiluminescent singlet oxygen acceptor and a fluorescent compound) simultaneously.

Figure 16:
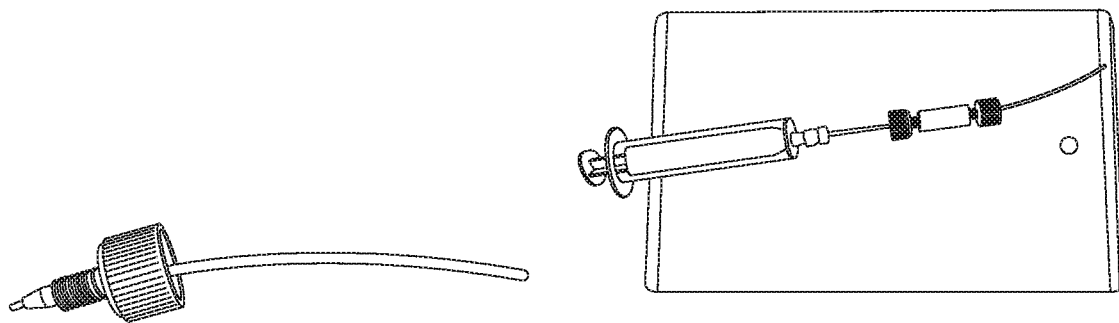
FIG. 16 is a set of images of a hollow polymer optic fiber connected to a fitting and a syringe, according to an illustrative embodiment.

Example 4—Preparation of a Hollow Polymer Optical Fiber for Dyeing of its Interior Surfaces with Acceptor Dye Compositions Example 4 is an example of a process and system components for preparing a hollow polymer optical fiber in order to dope the fiber with acceptor and/or donor dye compositions. In the example process, in order to dope the fiber with acceptor and/or donor dye compositions, polymer optical fibers were connected to a syringe. The syringe is used to pump solutions comprising acceptor dye and/or donor dye compositions, as well as solutions (e.g. water, ethanol) for rinsing the interior of a fiber, into the fibers. The polymer optical fibers were connected to the syringe via an appropriate sized threaded tube fitting nut and ferrule. For a 1.3 mm polymer optical fiber, a 1/16th inch high-performance (pressure) liquid chromatography (HPLC) fitting can be used. The fitting nut was attached to a coupler that was then also attached to a syringe or syringe pump. FIG. 16 shows two images of a length of hollow polymer optical fiber attached to a fitting (left image) and a syringe (right image).

Example 5—Doping the Interior of a Hollow Polymer Optic Fiber with an Acceptor Dye Composition Example 5 is an example of a process for doping the interior of a length of hollow polymer optical fiber with an acceptor dye composition (e.g. comprising a chemiluminescent singlet oxygen acceptor and a fluorescent compound). In the example process, the acceptor dye composition comprises C28 thioxene and a europium chelate ($Eu(NTA)_3BINAPO$).

A portion (600 μL) of an acceptor dye solution of $Eu(NTA)_3BINAPO$ and C28 thioxene in 2-ethoxyethanol, prepared as described in Example 2 above, was placed in a test tube and heated to 70° C. in an oil bath. In order to dope the interior of a hollow polymer optic fiber, 15 cm lengths of hollow polymer optical fiber, for example the 19-hole polymer optical fiber described in Example 3 above, were attached to a syringe as described in Example 4 above. The syringe was filled with 200 proof ethanol. The ethanol was pushed through the attached hollow polymer optical fiber, thereby contacting and wetting the interior surfaces of the holes of the fiber. The fiber was then flushed with air using a dry syringe. The heated dye solution of $Eu(NTA)_3BINAPO$ and C28 thioxene in 2-ethoxyethanol was then drawn quickly and completely into the fiber (e.g. into the multiple holes of the multi-hole hollow polymer optic fiber).

The entire length of the fiber was visibly fluorescent under long UV excitation (~366 nm, handheld lamp) confirming presence of the acceptor dye solution within the fiber. Additional lengths of fiber were attached to the syringe and dyed in the same manner. A fiber can also be partially doped via the example process. In particular, dye solution can be drawn into a selected portion of a fiber within a specific distance (e.g. a small distance, e.g. 1-2 cm) from the end of the fiber. By contacting a selected portion of the fiber within a specific distance of from the end of the fiber with acceptor dye, the selected portion of the fiber can be doped, while the remaining portion of the fiber can be left undoped.

The fibers filled with dye solution were placed an oven at 80° C. for about 5 minutes, then removed and allowed to cool to room temperature and rested at room temperature for 20 minutes. The fibers were re-attached to the syringe and cleared of dye solution by forcing air through, then rinsed with 200 proof ethanol followed by air, then water also followed by air to dry the interior of the fiber capillaries.

Example 6—Characterization of Emission from an Acceptor Dye Doped Hollow Polymer Optical Fiber and Light Transmission Along an Acceptor Dye Doped Hollow Polymer Optic Fiber Example 6 is an example showing characterization of light emission from hollow polymer optic fibers doped with a fluorescent compound used in an acceptor dye composition (e.g. an europium chelate). The example also shows characterization of light transmission along the fibers. In the example, fibers doped with a europium chelate were prepared as described in Example 5 above. As described in Example 5 above, after the fibers were filled with acceptor dye solution, heated, and allowed to cool, the fibers were re-attached to a syringe and cleared of dye solution by forcing air through the fibers. The fibers were then rinsed with 200 proof ethanol, after which air was again forced through the fibers. Finally, the fibers were rinsed with water, and again air was forced through the fibers dry the interior of the fiber capillaries.

Figure 17A:
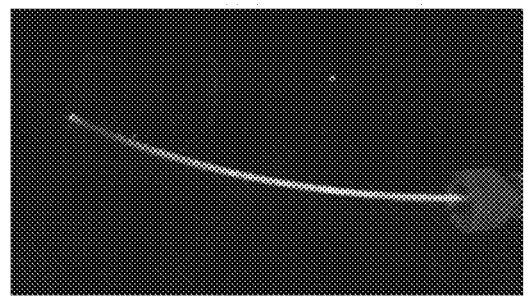
FIG. 17A is an image showing light emission from an acceptor dye doped hollow polymer optic fiber, according to an illustrative embodiment.

The fibers were illuminated with UV light having a wavelength of 366 nm via a handheld laboratory UV lamp. Fluorescence emission of the europium chelate with which the fibers were doped was observable and confirmed the presence of the europium chelate dye within the fibers. FIG. 17A is an image of a fiber 1702 doped with europium chelate that shows fluorescence emission from the fiber resulting from illumination with UV light.

Figure 17B:
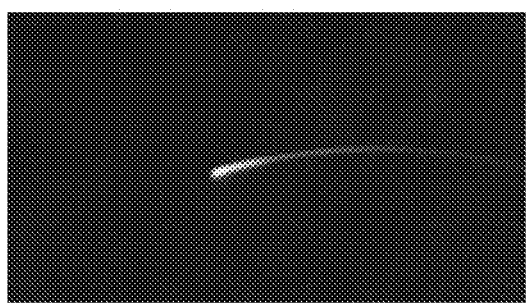
FIG. 17B is an image showing light emission a hollow polymer optic fiber, wherein a portion of the fiber within a short (from 1 to 2 cm) distance from an end of the fiber is doped with an acceptor dye composition, according to an illustrative embodiment.
Figure 17C:
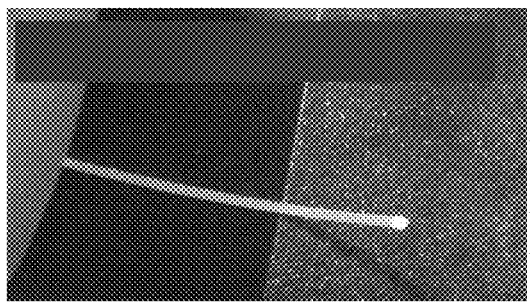
FIG. 17C is an image showing emission light transmitted along a hollow polymer optic fiber, and exiting from an undoped end of the fiber, according to an illustrative embodiment.

FIG. 17B and FIG. 17C are images of a different fiber. Only a portion of the fiber within 1-2 cm from an end of the fiber shown in FIG. 17B and FIG. 17C was doped with the europium chelate dye, and no dye was incorporated into the other portion of the fiber (leaving the remainder of the fiber undoped). FIG. 17B is an image of the end of the fiber that was doped, showing emission from the europium chelate of the doped end of the fiber. FIG. 17C is an image of the other, undoped, end of the fiber. FIG. 17C shows light exiting the undoped end of the fiber, resulting from the excitation of the doped end of the fiber by UV light (the undoped end shown in FIG. 17C was not illuminated with UV light). The light transmission from the undoped end of the fiber shows the transmission of the europium chelate emission from the doped end, along the polymer optical fiber, and out of the other end of the fiber.

Example 7—Characterization of a Doped Polymer Optical Fiber in Response to Singlet Oxygen Example 7 is an example showing characterization of emission of light produced from a polymer optic fiber doped with an acceptor dye composition comprising a chemiluminescent singlet oxygen acceptor (e.g. thioxene, e.g. C28 thioxene) and a fluorescent compound (e.g. an europium chelate) in response to singlet oxygen. A test polymer optic fiber was doped with an acceptor dye composition comprising a europium chelate and C28-thioxene.

In order to test the emission from the test fiber (doped with the europium chelate and thioxene), small sections, approximately 2.5 mm in length, of the test fiber were placed into a well of a 384-well plate. An undoped polymer optic fiber was used as a first control fiber. Portions of the first control fiber (the undoped fiber) were placed into another well of the 384-well plate. A fiber dyed only with the europium chelate (and not thioxene) was used as a second control fiber. Portions of the second control fiber (doped only with europium chelate and not thioxene) were placed into a third well of the 384-well plate.

Figure 18A:
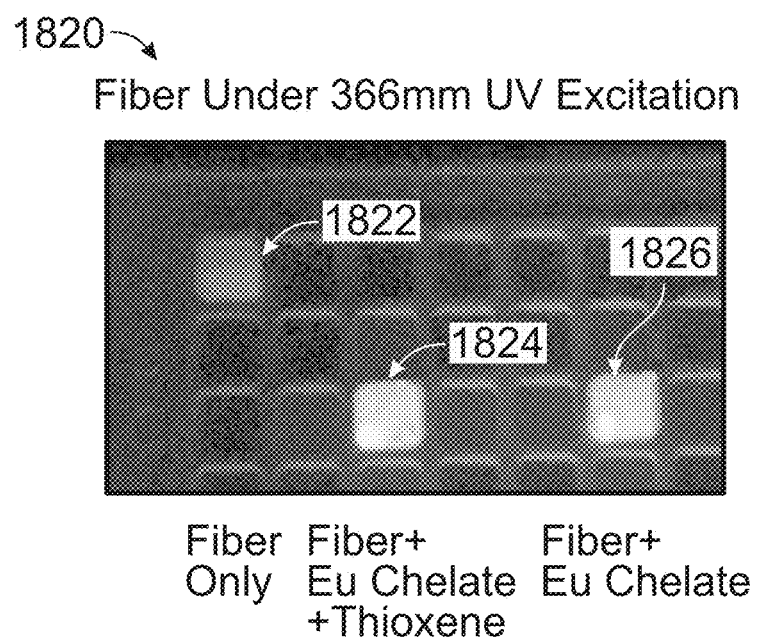
FIG. 18A is an image of light emission from sections of an undoped fiber, a fiber doped with a europium chelate, and a fiber doped with a europium chelate and thioxene, according to an illustrative embodiment.

FIG. 18A is an image showing emission from the sections of the three different fibers (the test fiber, first control fiber, and second control fiber) in the well plate under UV illumination having a wavelength of 366 nm (1820). The undoped, first control fiber 1822 emits blue fluorescence. The blue fluorescence emitted by the first control fiber is intrinsic fluorescence from the polystyrene of which the fibers (the test fiber, first control, and second control) are made. Both the test fiber 1824 (doped with europium chelate and C-28 thioxene) and the second control fiber 1826 (doped only with the europium chelate and not thioxene) emit red fluorescent light, produced via fluorescence of the europium chelate with which both fibers 1824 and 1826 are doped.

Next, the 384-well plate in which the fibers were placed was placed in an EnVision Multilabel Reader (PerkinElmer, Waltham, Mass.) and read in luminescence mode with a narrow band europium filter (e.g. an optical filter substantially transparent to light having a wavelength corresponding to a wavelength of emission light from europium and substantially opaque to light having other wavelengths). Luminescence was not observed from any of the test fiber, first control and second control fibers in the absence of an excitation source.

The different fibers were then stimulated with singlet oxygen by immersing them in a solution comprising sodium molybdate and hydrogen peroxide in deuterium oxide ($D_2O$). Without being bound to a particular theory, the sodium molybdate and hydrogen peroxide in $D_2O$ solution (hereafter "$MoO_4^{-2}/H_2O_2$ solution") generates a steady state concentration of singlet oxygen over a period of time as the hydrogen peroxide is catalytically converted to molecular oxygen. $D_2O$ is used to extend the lifetime of the thus produced singlet oxygen. The singlet oxygen intensity produced by the $MoO_4^{-2}/H_2O_2$ solution is comparable to that expected from excitation of a photosensitizer. The singlet oxygen intensity produced by the $MoO_4^{-2}/H_2O_2$ solution is sufficient to generate measurable light output from singlet oxygen responsive reagents such as AlphaLISA Acceptor beads.

The $MoO_4^{-2}/H_2O_2$ solution was prepared as follows. A molybdate solution comprising 1 mM sodium molybdate, 10 mM potassium carbonate, and 0.2% Tween-20 detergent in $D_2O$ was prepared. A 3% hydrogen peroxide in $D_2O$ was prepared. The molybdate solution (450 µL) is combined with the hydrogen peroxide solution (50 µL) immediately prior to use. Such a solution will continue to produce singlet oxygen for several hours.

The portions of the different fibers—the test fiber, first control fiber, and second control fiber—were immersed in the $MoO_4^{-2}/H_2O_2$ solution. Without being bound to a particular theory, when the test fiber (doped with C28 thioxene and europium chelate) is immersed in the $MoO_4^{-2}/H_2O_2$ solution, the steady state singlet oxygen ($^1O_2$) produced by the $MoO_4^{-2}/H_2O_2$ solution reacts with the chemiluminescent singlet oxygen acceptor (e.g. the C28 thioxene) with which the test fiber was doped. The reaction of the C28 thioxene with singlet oxygen produces UV emission, which excites the europium chelate, which, in turn, emits fluorescent light. Accordingly, when placed in the $MoO_4^{-2}/H_2O_2$ solution, a high signal (more than 1000-fold over background) was detected from the test fiber doped with both the europium chelate and C-28 thioxene.

When the undoped first control fiber was immersed in the $MoO_4^{-2}/H_2O_2$ solution, the undoped first control fiber a signal comparable to a background signal was detected. Similarly, when the second control fiber (doped only with europium chelate and not thioxene) was immersed in the $MoO_4^{-2}/H_2O_2$ solution, a signal comparable to a background signal was detected.

Figure 18B:
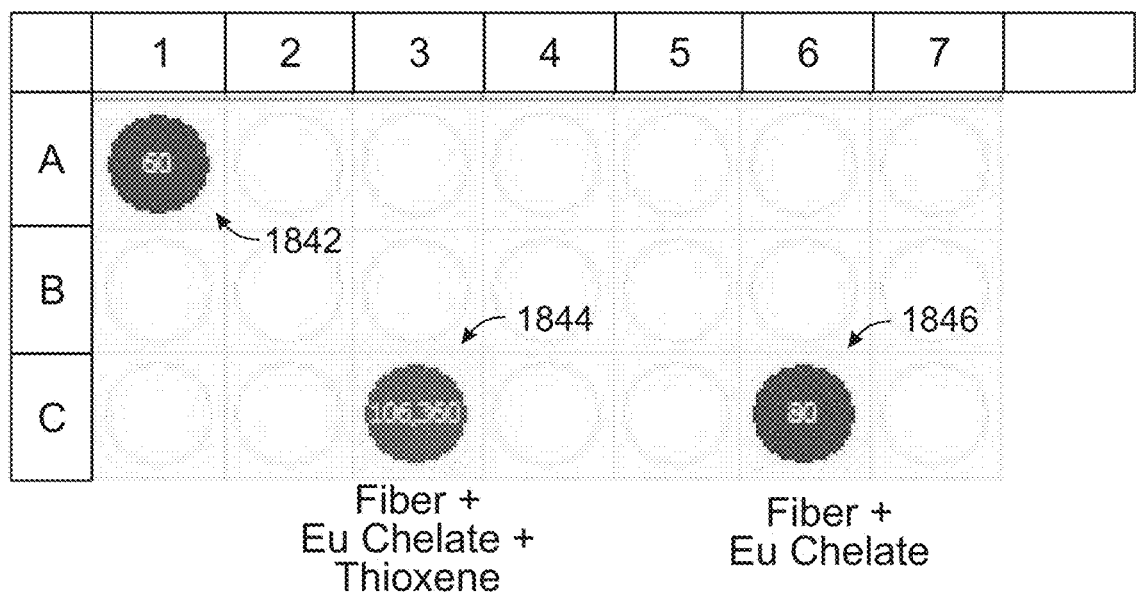
FIG. 18B is a screenshot showing luminescence data from sections of an undoped fiber, a fiber doped with a europium chelate, and a fiber doped with a europium chelate and thioxene, according to an illustrative embodiment.

FIG. 18B shows a screenshot 1840 comprising data corresponding to detected signal from the test fiber, first control fiber, and second control fiber, recorded via the EnVision Multilabel Reader (PerkinElmer, Waltham, Mass.). The screenshot shows the first control fiber position 1842, test fiber position 1844, and second control fiber position 1846 in the multi-well plate. The numbers in the figure at each fiber position correspond to the amplitude of the signal (measured in counts) detected from each fiber position in the plate. In particular, a signal of 106,360 was detected from the test fiber, while much smaller signals, 60 and 80, were detected from the first and second control fibers, respectively.

Figure 18C:
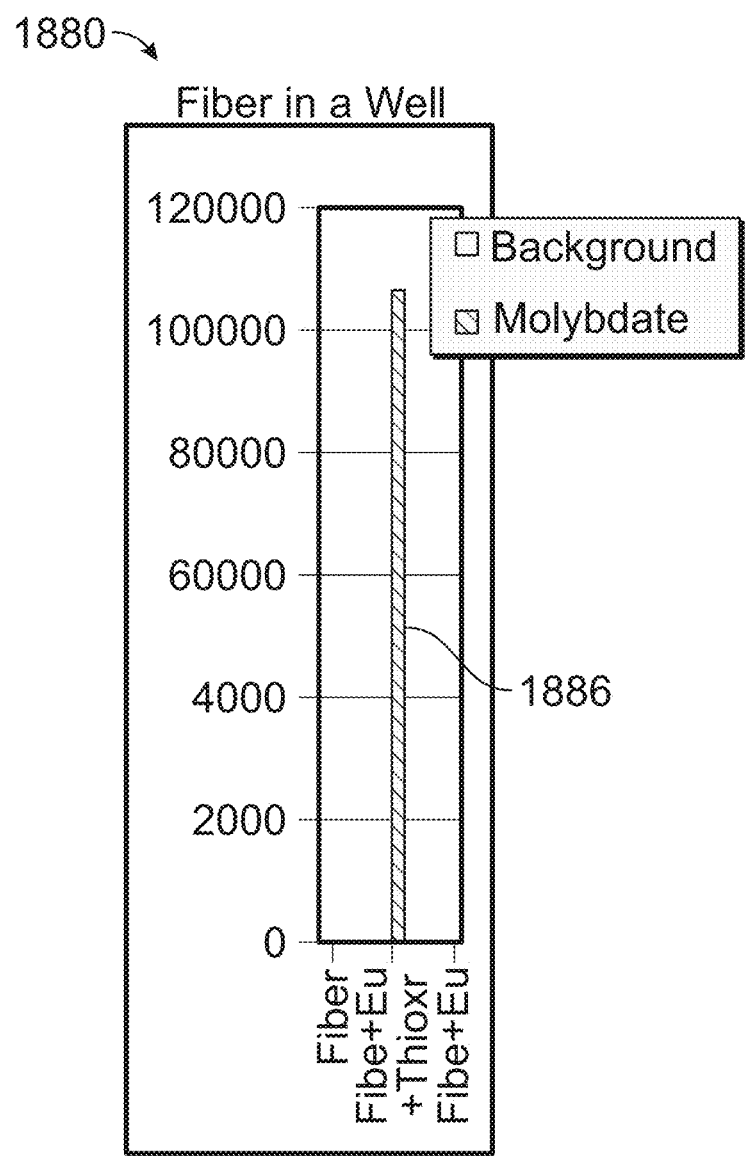
FIG. 18C is a graph of signal from detected emission from differently doped fiber sections, according to an illustrative embodiment.

FIG. 18C shows a graph 1880 depicting the detected signal from each of the three fibers under $MoO_4/H_2O_2$ stimulation. The graph of FIG. 18 also shows the background signal (e.g. signal detected without any $MoO_4/H_2O_2$ stimulation). The signals from the control fibers produced under $MoO_4/H_2O_2$ stimulation are comparable to the background signal, while the signal 1886 from the test fiber doped with the europium chelate and thioxene compound produced under $MoO_4/H_2O_2$ stimulation was significantly (e.g. a factor of 1,000) higher than the background signal.

Accordingly, Example 7 demonstrates emission from a fiber doped with an acceptor compound produced via singlet oxygen channeling.

Example 8—Streptavidin Coating of Chemiluminescent Polymer Optical Fibers

Example 8 is an example of a process for coating the interior surfaces of a polymer optical fiber doped with an acceptor dye composition with streptavidin. Streptavidin may be used as a fiber binding partner, (e.g. to bind to a biotinylated analyte) or as a coating to which a fiber binding partner can be attached (e.g. a biotinylated antibody can be bound to a streptavidin coating). In the example process of Example 8, streptavidin, obtained as a lyophilized solid, is dissolved in a coating buffer comprising 100 mM $Na_2HPO_4$/ 50 mM citric acid, pH 5.0 for a final concentration of from 5 to 25 μg/mL. The streptavidin solution is drawn into a syringe and pumped through the capillaries of a 15 to 50 cm section of doped (e.g. with an acceptor composition) polymer optical fiber. The fiber ends are then sealed with Parafilm. The fibers are incubated at 37° C. for 24 hours in a humidified incubator. The fibers are then flushed with DELFIA Platewash (PerkinElmer, Waltham Mass.) comprising 0.05% Tween-20. The fibers are then filled (e.g. via a syringe as described in Example 4 above) with a solution of 0.2% bovine serum albumin (B S A) and 6% D-sorbitol in 50 mM Tris-HCl, pH 7.0, 150 mM NaCl. The ends of the fibers are sealed with Parafilm and stored in an incubator at 23° C. overnight. The BSA solution is flushed out of the fibers by passing air through the fibers. The fibers are then dried by passing dry nitrogen through the fibers for 10 minutes.

Example 9—Embedding the Interior of a Length of Hollow Polymer Optical Fiber with a Sensitizer Dye Example 9 is an example of a process for embedding the interior of a hollow polymer optical fiber with a donor dye (e.g. a photosensitizer). For example, a hollow polymer fiber can be doped with a donor dye composition comprising napthalocyanine. In the example, silicon 2,3-naphthalocyanine bis(trihexylsilyloxide) (20 mg, 15 μmol, SigmaAldrich 389935) is placed in a glass vial and dissolved in 4 mL 2-ethoxyethanol by heating to approximately 100° C. and applying ultra-sonication. A portion of this solution (600 μL) is placed in a test tube and heated to 80° C. in an oil bath. A hollow polymer optical fiber, 15 cm in length, is attached to a syringe as described in Example 4. The syringe was filled with 200 proof ethanol and the ethanol is pushed through the attached hollow polymer optical fiber to wet the interior surfaces of the capillaries of the fiber. Then the fiber was then flushed with air using a dry syringe. The warm sensitizer dye solution is then drawn quickly and completely into the polymer optic fiber.

The fiber filled with dye solution is placed an oven at 80° C. for about 5 minutes, then removed and allowed to cool to room temperature. The fiber is kept at room temperature for 20 minutes. The fibers is re-attached to the syringe and cleared of dye solution by forcing air through, then rinsed with 200 proof ethanol followed by air, then water, then air to dry the interior of the fiber capillaries. The resulting sensitizer polymer optical fiber is stored in the dark.

Example 10—Streptavidin Coating of Donor Polymer Optical Fibers

Figure 19:
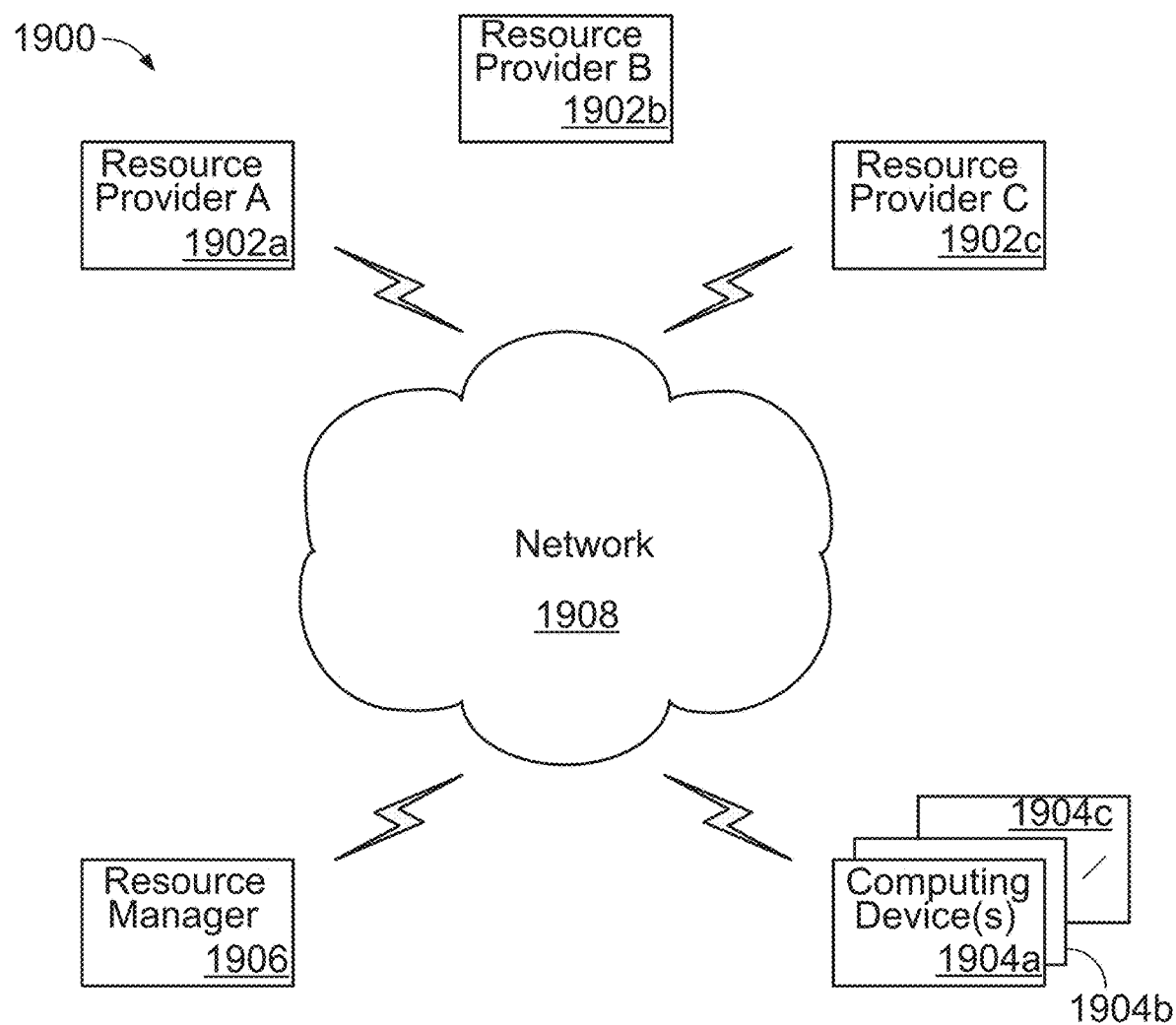
FIG. 19 is a block diagram of an exemplary cloud computing environment, used in certain embodiments.

Example 10 is an example of a process for coating the interior of a donor dye (e.g. a photosensitizer) doped polymer optical fiber with streptavidin. Streptavidin, obtained as a lyophilized solid, is dissolved in a coating buffer comprising 100 mM $Na_2HPO_4$/50 mM citric acid, pH 5.0) for a final concentration of 5 to 25 μg/mL. The streptavidin solution is drawn into a syringe and pumped through the capillaries of a 15 to 50 cm section of donor dye doped polymer optical fiber under subdued lighting conditions (e.g. under low levels of ambient light). The fiber ends are then sealed with Parafilm and the fibers are incubated at 37° C. for 24 hours in a humidified incubator in the dark. The fibers are then flushed with DELFIA Platewash (PerkinElmer, Waltham Mass.) comprising 0.05% Tween-20. The fibers are then filled (e.g. by syringe) with a solution of 0.2% bovine serum albumin (BSA) and 6% D-sorbitol in 50 mM Tris-HCl, pH 7.0, 150 mM NaCl. The ends of the fibers are sealed with Parafilm, and the fibers are stored in an incubator at 23° C. overnight in the dark. Following incubation, the BSA solution is flushed out of the fibers by passing air through the fibers. The fibers are then dried by passage of dry nitrogen through the fiber for 10 minutes and stored in the dark VI. Network Environment and Computing Systems As shown in FIG. 19, an implementation of a network environment 1900 for use in providing systems, methods, and architectures for retrieving, managing, and analyzing data produced via the hollow polymer fiber optic systems (e.g. via the custom diagnostic software) described herein is shown and described. In brief overview, referring now to FIG. 19, a block diagram of an exemplary cloud computing environment 1900 is shown and described. The cloud computing environment 1900 may include one or more resource providers 1902*a*, 1902*b*, 1902*c* (collectively, 1902). Each resource provider 1902 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1902 may be connected to any other resource provider 1902 in the cloud computing environment 1900. In some implementations, the resource providers 1902 may be connected over a computer network 1908. Each resource provider 1902 may be connected to one or more computing device 1904a, 1904b, 1904c (collectively, 1904), over the computer network 1908.

The cloud computing environment 1900 may include a resource manager 1906. The resource manager 1906 may be connected to the resource providers 1902 and the computing devices 1904 over the computer network 1908. In some implementations, the resource manager 1906 may facilitate the provision of computing resources by one or more resource providers 1902 to one or more computing devices 1904. The resource manager 1906 may receive a request for a computing resource from a particular computing device 1904. The resource manager 1906 may identify one or more resource providers 1902 capable of providing the computing resource requested by the computing device 1904. The resource manager 1906 may select a resource provider 1902 to provide the computing resource. The resource manager 1906 may facilitate a connection between the resource provider 1902 and a particular computing device 1904. In some implementations, the resource manager 1906 may establish a connection between a particular resource provider 1902 and a particular computing device 1904. In some implementations, the resource manager 1906 may redirect a particular computing device 1904 to a particular resource provider 1902 with the requested computing resource.

Figure 20:
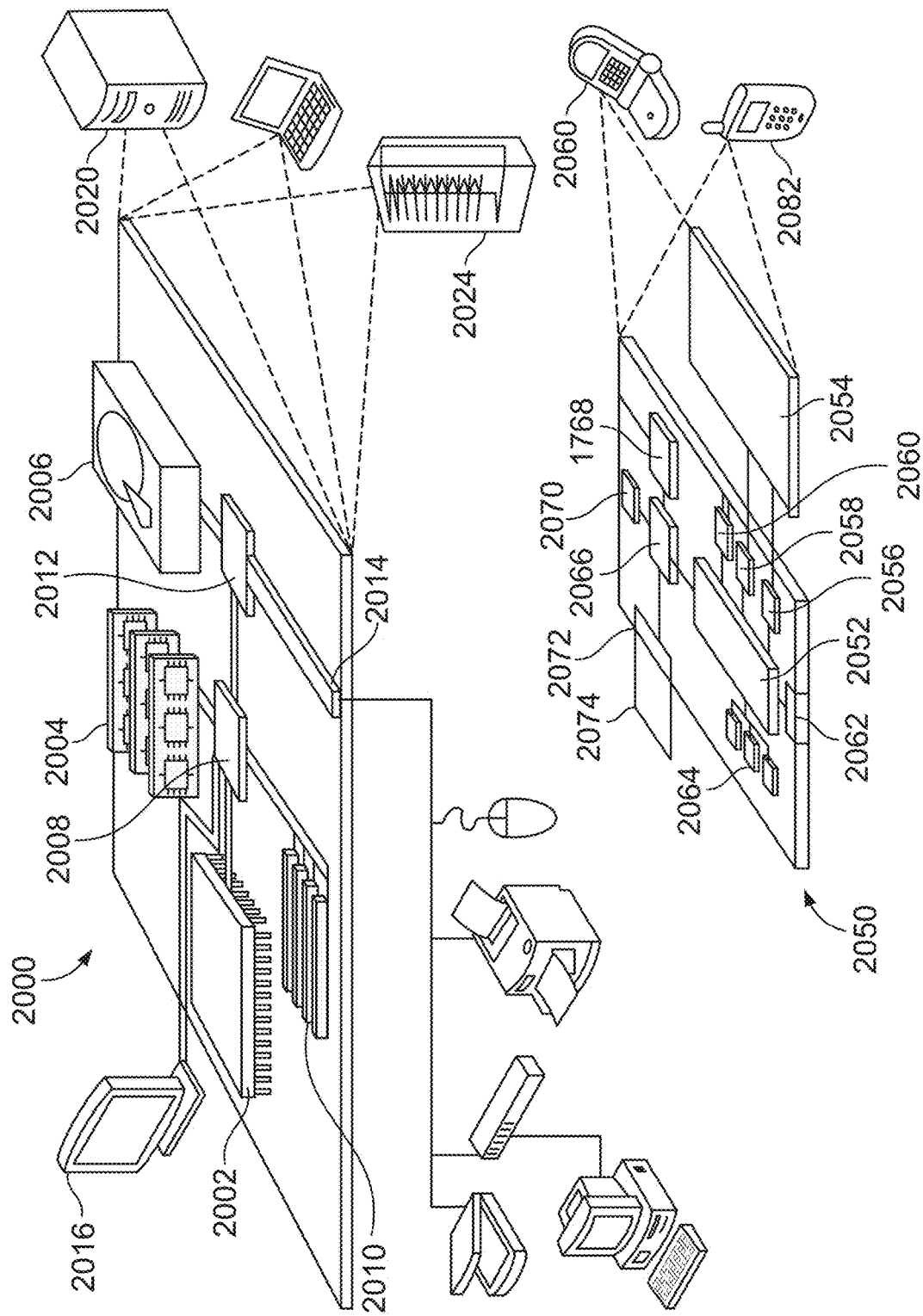
FIG. 20 is a block diagram of an example computing device and an example mobile computing device used in certain embodiments.

FIG. 20 shows an example of a computing device 2000 and a mobile computing device 2050 that can be used to implement the techniques described in this disclosure. The computing device 2000 is intended to represent various forms of digital computers, such as laptops, desktops, workstations, personal digital assistants, servers, blade servers, mainframes, and other appropriate computers. The mobile computing device 2050 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 2000 includes a processor 2002, a memory 2004, a storage device 2006, a high-speed interface 2008 connecting to the memory 2004 and multiple high-speed expansion ports 2010, and a low-speed interface 2012 connecting to a low-speed expansion port 2014 and the storage device 2006. Each of the processor 2002, the memory 2004, the storage device 2006, the high-speed interface 2008, the high-speed expansion ports 2010, and the low-speed interface 2012, are interconnected using various busses, and may be mounted on a common motherboard or in other manners as appropriate. The processor 2002 can process instructions for execution within the computing device 2000, including instructions stored in the memory 2004 or on the storage device 2006 to display graphical information for a GUI on an external input/output device, such as a display 2016 coupled to the high-speed interface 2008. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 2004 stores information within the computing device 2000. In some implementations, the memory 2004 is a volatile memory unit or units. In some implementations, the memory 2004 is a non-volatile memory unit or units. The memory 2004 may also be another form of computer-readable medium, such as a magnetic or optical disk.

The storage device 2006 is capable of providing mass storage for the computing device 2000. In some implementations, the storage device 2006 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 2002), perform one or more methods, such as those described above. The instructions can also be stored by one or more storage devices such as computer- or machine-readable mediums (for example, the memory 2004, the storage device 2006, or memory on the processor 2002).

The high-speed interface 2008 manages bandwidth-intensive operations for the computing device 2000, while the low-speed interface 2012 manages lower bandwidth-intensive operations. Such allocation of functions is an example only. In some implementations, the high-speed interface 2008 is coupled to the memory 2004, the display 2016 (e.g., through a graphics processor or accelerator), and to the high-speed expansion ports 2010, which may accept various expansion cards (not shown). In the implementation, the low-speed interface 2012 is coupled to the storage device 2006 and the low-speed expansion port 2014. The low-speed expansion port 2014, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 2000 may be implemented in a number of different forms, as shown in the figure. For example, it may be implemented as a standard server 2020, or multiple times in a group of such servers. In addition, it may be implemented in a personal computer such as a laptop computer 2022. It may also be implemented as part of a rack server system 2024. Alternatively, components from the computing device 2000 may be combined with other components in a mobile device (not shown), such as a mobile computing device 2050. Each of such devices may contain one or more of the computing device 2000 and the mobile computing device 2050, and an entire system may be made up of multiple computing devices communicating with each other.

The mobile computing device 2050 includes a processor 2052, a memory 2064, an input/output device such as a display 2054, a communication interface 2066, and a transceiver 2068, among other components. The mobile computing device 2050 may also be provided with a storage device, such as a micro-drive or other device, to provide additional storage. Each of the processor 2052, the memory 2064, the display 2054, the communication interface 2066, and the transceiver 2068, are interconnected using various buses, and several of the components may be mounted on a common motherboard or in other manners as appropriate.

The processor 2052 can execute instructions within the mobile computing device 2050, including instructions stored in the memory 2064. The processor 2052 may be implemented as a chipset of chips that include separate and multiple analog and digital processors. The processor 2052 may provide, for example, for coordination of the other components of the mobile computing device 2050, such as control of user interfaces, applications run by the mobile computing device 2050, and wireless communication by the mobile computing device 2050.

The processor 2052 may communicate with a user through a control interface 2058 and a display interface 2056 coupled to the display 2054. The display 2054 may be, for example, a TFT (Thin-Film-Transistor Liquid Crystal Display) display or an OLED (Organic Light Emitting Diode) display, or other appropriate display technology. The display interface 2056 may comprise appropriate circuitry for driving the display 2054 to present graphical and other information to a user. The control interface 2058 may receive commands from a user and convert them for submission to the processor 2052. In addition, an external interface 2062 may provide communication with the processor 2052, so as to enable near area communication of the mobile computing device 2050 with other devices. The external interface 2062 may provide, for example, for wired communication in some implementations, or for wireless communication in other implementations, and multiple interfaces may also be used.

The memory 2064 stores information within the mobile computing device 2050. The memory 2064 can be implemented as one or more of a computer-readable medium or media, a volatile memory unit or units, or a non-volatile memory unit or units. An expansion memory 2074 may also be provided and connected to the mobile computing device 2050 through an expansion interface 2072, which may include, for example, a SIMM (Single In Line Memory Module) card interface. The expansion memory 2074 may provide extra storage space for the mobile computing device 2050, or may also store applications or other information for the mobile computing device 2050. Specifically, the expansion memory 2074 may include instructions to carry out or supplement the processes described above, and may include secure information also. Thus, for example, the expansion memory 2074 may be provide as a security module for the mobile computing device 2050, and may be programmed with instructions that permit secure use of the mobile computing device 2050. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 2052), perform one or more methods, such as those described above. The instructions can also be stored by one or more storage devices, such as one or more computer- or machine-readable mediums (for example, the memory 2064, the expansion memory 2074, or memory on the processor 2052). In some implementations, the instructions can be received in a propagated signal, for example, over the transceiver 2068 or the external interface 2062.

The mobile computing device 2050 may communicate wirelessly through the communication interface 2066, which may include digital signal processing circuitry where necessary. The communication interface 2066 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 2068 using a radio-frequency. In addition, short-range communication may occur, such as using a Bluetooth®, Wi-Fi™, or other such transceiver (not shown). In addition, a GPS (Global Positioning System) receiver module 2070 may provide additional navigation- and location-related wireless data to the mobile computing device 2050, which may be used as appropriate by applications running on the mobile computing device 2050.

The mobile computing device 2050 may also communicate audibly using an audio codec 2060, which may receive spoken information from a user and convert it to usable digital information. The audio codec 2060 may likewise generate audible sound for a user, such as through a speaker, e.g., in a handset of the mobile computing device 2050. Such sound may include sound from voice telephone calls, may include recorded sound (e.g., voice messages, music files, etc.) and may also include sound generated by applications operating on the mobile computing device 2050.

The mobile computing device 2050 may be implemented in a number of different forms, as shown in the figure. For example, it may be implemented as a cellular telephone 2080. It may also be implemented as part of a smart-phone 2082, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. In view of the structure, functions and apparatus of the systems and methods described here, in some implementations.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While apparatus, systems, and methods have been particularly shown and described with reference to specific preferred embodiments, it should be understood by those skilled in the art that various changes in form and detail may be made therein without departing from the spirit and scope of the invention as defined by the appended claims.

What is claimed is:

1. A method for detecting and/or quantifying one or more analytes of interest in a sample, the method comprising:
    introducing a sample solution into the interior of a hollow polymer optic fiber, the solution comprising the one or more analytes of interest and donor particles, the donor particles comprising (i) a donor dye composition that releases singlet oxygen when illuminated with excitation light, and (ii) a particle binding partner that binds to at least one particular analyte of the one or more analytes of interest, wherein the hollow polymer optic fiber comprises (i) an acceptor dye composition that accepts singlet oxygen and as a consequence emits light and (ii) a fiber binding partner that binds to the at least one particular analyte;
    conducting excitation light through the hollow polymer optic fiber; and
    detecting emission light traveling through the hollow polymer optic fiber, the emission light produced via singlet oxygen channeling, thereby detecting and/or quantifying the at least one particular analyte of interest in the sample.

2. The method of claim 1, comprising introducing a sample solution into the interiors of a plurality of hollow polymer optic fibers of a bundle of hollow polymer optic fibers, wherein each hollow polymer optic fiber is doped with a corresponding acceptor dye composition and comprises a corresponding fiber binding partner.

3. The method of claim 2, wherein each of a plurality of hollow polymer optic fibers of the bundle has a different fiber binding partner conjugated to its interior surface.

4. The method of claim 3, wherein:
    a first hollow polymer optic fiber of the bundle is doped with a first acceptor dye composition having a first emission wavelength,
    a second hollow polymer optic fiber of the bundle is doped with a second acceptor dye composition having a second emission wavelength that is different from the first emission wavelength,
    the first hollow polymer optic fiber of the bundle has a first fiber binding partner conjugated to its interior surface, and
    the second hollow polymer optic fiber of the bundle has a second fiber binding partner conjugated to its interior surface, the second fiber binding partner different from the first fiber binding partner.

5. The method of claim 4, comprising distinguishably detecting light having a wavelength corresponding to the first emission wavelength and light having a wavelength corresponding the second emission wavelength.

6. The method of claim 4, comprising:
    introducing into the sample solution a first donor particle comprising a donor dye composition and a first particle binding partner, wherein the first particle binding partner binds to a first analyte to which the first fiber binding partner also binds;
    introducing into the sample solution a second donor particle comprising a donor dye composition and a second particle binding partner, wherein the second particle binding partner binds to a second analyte to which the second fiber binding partner also binds;
    introducing the sample solution comprising the first donor particle and second donor particle into interiors of the hollow polymer optic fibers of the bundle of hollow polymer optic fibers.

7. The method of claim 2, comprising:
    (a) introducing into the sample solution a first donor particle comprising a first donor dye composition and a first particle binding partner, wherein the first particle binding partner binds to a first analyte;
    (b) introducing into the sample solution a second donor particle comprising a second donor dye composition and a second particle binding partner, wherein the second particle binding partner binds to a second analyte;

(c) introducing the sample solution comprising the first donor particle and second donor particle into interiors of the hollow polymer optic fibers of the bundle, wherein:
- a first hollow polymer optic fiber of the bundle has a first fiber binding partner conjugated to its interior surface,
- a second hollow polymer optic fiber of the bundle has a second fiber binding partner conjugated to its interior surface, the second binding partner different from the first binding partner,
- the first fiber binding partner binds to the first analyte, and
- the second fiber binding partner binds to the second analyte;

(d) illuminating the fiber bundle with excitation light having a first wavelength corresponding to an excitation wavelength of the first donor dye composition and detecting resultant emission light; and (e) illuminating the fiber bundle with excitation light having a second wavelength corresponding to an excitation wavelength of the second donor dye composition and detecting resultant emission light.

8. The method of claim 1, wherein introducing the sample solution into the interior of the hollow polymer optic fiber comprises immersing the hollow polymer optic fiber into the sample solution such that the sample solution is drawn into the interior of the hollow polymer optic fiber via capillary action.

9. The method of claim 1, wherein the particle binding partner binds to at least a first analyte of the one or more analytes of interest and the fiber binding partner also binds to the first analyte.

10. The method of claim 1, wherein the hollow polymer optic fiber comprises multiple discrete portions along its length, each of which portions has a different concentration of the fiber binding partner conjugated to its interior surface for achieving a variety of levels of sensitivity of measurement of the at least one particular analyte of interest.

11. The method of claim 1, wherein the hollow polymer optic fiber comprises multiple discrete portions along its length, each of which portions has a different fiber binding partner conjugated to its interior surface.

12. A method for detecting and/or quantifying one or more analytes of interest in a sample, the method comprising:
introducing a sample solution into the interior of a hollow polymer optic fiber, the solution comprising one or more analytes of interest and acceptor particles, the acceptor particles comprising (i) an acceptor dye composition that accepts singlet oxygen and as a consequence emits light and (ii) a particle binding partner that binds to at least one particular analyte of the one or more analytes of interest, wherein the hollow polymer optic fiber comprises (i) a donor dye composition that releases singlet oxygen when illuminated with excitation light and (ii) a fiber binding partner that binds to the at least one particular analyte;
conducting excitation light through the hollow polymer optic fiber; and
detecting emission light traveling through the hollow polymer optic fiber, the emission light produced via singlet oxygen channeling, thereby detecting and/or quantifying the at least one particular analyte of interest in the sample.

13. The method of claim 12, comprising introducing a sample solution into the interiors of a plurality of hollow polymer optic fibers of a bundle of hollow polymer optic fibers, wherein each hollow polymer optic fiber is doped with a corresponding donor dye composition and comprises a corresponding fiber binding partner.

14. The method of claim 13, wherein each of a plurality of hollow polymer optic fibers of the bundle of hollow polymer optic fibers has a different fiber binding partner conjugated to its interior surface.

15. The method of claim 13, comprising:
introducing into the sample solution a first acceptor particle comprising a first acceptor dye composition and a first particle binding partner, wherein the first acceptor dye composition has a first emission wavelength;
introducing into the sample solution a second acceptor particle comprising a second acceptor dye composition and a second particle binding partner, wherein the second acceptor dye composition has a second emission wavelength that is different from the first emission wavelength, and the second particle binding partner is different from the first particle binding;
introducing the sample solution comprising the first acceptor particle and second acceptor particle into interiors of the hollow polymer optic fibers of the bundle, wherein:
- one or more hollow polymer optic fibers of the bundle have a first fiber binding partner conjugated to an interior surface, wherein the first fiber binding partner binds to a first analyte to which the first particle binding partner also binds, and
- one or more hollow polymer optic fibers of the bundle have a second fiber binding partner conjugated to an interior surface, wherein the second fiber binding partner binds to a second analyte to which the second particle binding partner also binds.

16. The method of claim 15, comprising distinguishably detecting light having a wavelength corresponding to the first emission wavelength and light having a wavelength corresponding to the second emission wavelength.

17. The method of claim 13, comprising:
(a) introducing into the sample solution a first acceptor particle comprising a first particle binding partner, wherein the first particle binding partner binds to a first analyte;
(b) introducing into the sample solution a second acceptor particle comprising a second particle binding partner, wherein the second particle binding partner binds to a second analyte;
(c) introducing the sample solution comprising the first acceptor particle and second acceptor particle into interiors of the hollow polymer optic fibers of the bundle, wherein:
- a first hollow polymer optic fiber of the bundle is doped with a first donor dye composition and has a first fiber binding partner conjugated to its interior surface,
- a second hollow polymer optic fiber of the bundle is doped with a second donor dye composition and has a second fiber binding partner conjugated to its interior surface, the second binding partner different from the first binding partner,
- the first fiber binding partner binds to the first analyte,
- the second fiber binding partner binds to the second analyte,
(d) illuminating the fiber bundle with excitation light having a first wavelength corresponding to an excitation wavelength of the first donor dye composition and detecting resultant emission light; and (e) illuminating the fiber bundle with excitation light having a second wavelength corresponding to an excitation wavelength of the second donor dye composition and detecting resultant emission light.

18. The method of claim 12, wherein introducing the sample solution into the interior of the hollow polymer optic fiber comprises immersing the hollow polymer optic fiber into the sample solution such that the sample solution is drawn into the interior of the hollow polymer optic fiber via capillary action.

19. The method of claim 12, wherein the particle binding partner binds to at least a first analyte of the one or more analytes of interest and the fiber binding partner also binds to the first analyte.

20. The method of claim 12, wherein the hollow polymer optic fiber comprises multiple discrete portions along its length, each of which portions has a different concentration of the fiber binding partner conjugated to its interior surface for achieving a variety of levels of sensitivity of measurement of the at least one particular analyte of interest.

21. The method of claim 12, wherein the hollow polymer optic fiber comprises multiple discrete portions along its length, each of which portions has a different fiber binding partner conjugated to its interior surface.

* * * * *